US006686179B2

(12) United States Patent
Fleer et al.

(10) Patent No.: US 6,686,179 B2
(45) Date of Patent: Feb. 3, 2004

(54) FUSION POLYPEPTIDES OF HUMAN SERUM ALBUMIN AND A THERAPEUTICALLY ACTIVE POLYPEPTIDE

(75) Inventors: Reinhard Fleer, Bures-sur-Yvette (FR); Alain Fournier, Châtenay-Malabry (FR); Jean-Dominique Guitton, Paris (FR); Gérard Jung, Montlhery (FR); Patrice Yeh, Paris (FR)

(73) Assignee: Aventis Behring L.L.C., King of Prussia, PA (US)

( * ) Notice: Subject to any disclaimer, the term of this patent is extended or adjusted under 35 U.S.C. 154(b) by 0 days.

(21) Appl. No.: 09/984,186

(22) Filed: Oct. 29, 2001

(65) Prior Publication Data

US 2002/0151011 A1 Oct. 17, 2002

Related U.S. Application Data

(63) Continuation of application No. 09/258,532, filed on Feb. 26, 1999, now abandoned, which is a division of application No. 08/797,689, filed on Jan. 31, 1997, now Pat. No. 5,876,969, which is a continuation of application No. 08/256,927, filed on Jul. 28, 1994, now abandoned.

(30) Foreign Application Priority Data

Jan. 31, 1992 (FR) .............................. 92 01064

(51) Int. Cl.⁷ ................................................ C12P 21/02
(52) U.S. Cl. .................. 435/69.7; 435/320.1; 435/325; 435/252.3; 536/23.4; 530/350; 530/362
(58) Field of Search ............................. 530/362, 350; 435/69.7, 320.1, 325, 252.3; 536/23.4

(56) References Cited

U.S. PATENT DOCUMENTS

| 4,336,248 A | 6/1982 | Bonhard et al. ............. 424/101 |
| 4,670,393 A | 6/1987 | Seeburg et al. ............. 435/240 |
| 4,703,008 A | 10/1987 | Lin .......................... 435/240.2 |
| 4,732,889 A | 3/1988 | Cynshi et al. ................. 514/8 |
| 4,745,099 A | 5/1988 | Akamatsu et al. ............. 514/8 |
| 4,751,180 A | 6/1988 | Cousens et al. .............. 435/68 |
| 4,765,980 A | 8/1988 | DePrince et al. ........... 424/108 |
| 4,801,575 A | 1/1989 | Pardridge et al. .............. 514/4 |
| 4,806,524 A | 2/1989 | Kawaguchi et al. ............ 514/8 |
| 4,879,272 A | 11/1989 | Shimoda et al. ............... 514/8 |
| 4,914,027 A | 4/1990 | Knapp et al. .............. 435/69.6 |
| 4,954,437 A | 9/1990 | Beck et al. ................ 435/69.4 |
| 4,959,314 A | 9/1990 | Mark et al. ................ 435/69.1 |
| 4,970,300 A | 11/1990 | Fulton et al. ............... 530/383 |
| 5,045,312 A | 9/1991 | Aston et al. ............... 424/85.8 |
| 5,073,627 A | 12/1991 | Curtis et al. ............... 530/351 |
| 5,100,784 A | 3/1992 | Latta et al. ................ 435/69.7 |
| 5,116,944 A | 5/1992 | Sivam et al. ............... 530/362 |
| 5,116,964 A | 5/1992 | Capon et al. ............... 536/23.5 |
| 5,187,261 A | 2/1993 | Latta et al. ................ 530/363 |
| 5,223,408 A | 6/1993 | Goeddel et al. ............ 435/69.3 |
| 5,272,070 A | 12/1993 | Lehrman et al. .......... 435/172.1 |
| 5,302,697 A | 4/1994 | Goodey et al. .............. 530/325 |
| 5,330,971 A | 7/1994 | Wells et al. ................... 514/2 |
| 5,336,603 A | 8/1994 | Capon et al. ............... 435/69.7 |
| 5,380,712 A | 1/1995 | Ballance et al. .............. 514/12 |
| 5,441,868 A | 8/1995 | Lin .......................... 435/69.4 |
| 5,457,089 A | 10/1995 | Fibi et al. ..................... 514/8 |
| 5,541,158 A | 7/1996 | Vance et al. .................. 514/8 |
| 5,547,933 A | 8/1996 | Lin ............................... 514/8 |
| 5,612,196 A | 3/1997 | Becquart et al. ........... 435/69.6 |
| 5,618,698 A | 4/1997 | Lin .......................... 435/69.4 |
| 5,621,080 A | 4/1997 | Lin ........................... 530/350 |
| 5,641,663 A | 6/1997 | Garvin et al. ............. 435/172.1 |
| 5,646,012 A | 7/1997 | Fleer et al. ................. 435/69.1 |
| 5,665,863 A | 9/1997 | Yeh et al. ................... 530/351 |
| 5,679,777 A | 10/1997 | Anderson et al. ........... 530/385 |
| 5,705,363 A | 1/1998 | Imakawa et al. ......... 435/69.51 |
| 5,714,377 A | 2/1998 | Tanner et al. .......... 435/254.11 |
| 5,756,349 A | 5/1998 | Lin ........................... 435/325 |
| 5,766,883 A | 6/1998 | Ballance et al. ............ 435/69.7 |
| 5,844,095 A | 12/1998 | Linsley et al. ............ 530/387.3 |
| 5,856,298 A | 1/1999 | Strickland ..................... 514/8 |
| 5,876,969 A * | 3/1999 | Fleer et al. ................ 435/69.7 |
| 5,889,144 A | 3/1999 | Alila et al. ................. 530/300 |
| 5,948,428 A | 9/1999 | Lee et al. ................... 424/426 |
| 5,955,422 A | 9/1999 | Lin ............................... 514/8 |
| 5,968,510 A | 10/1999 | Linsley et al. ............. 424/141.1 |
| 5,977,318 A | 11/1999 | Linsley et al. .............. 530/388 |
| 5,981,474 A | 11/1999 | Manning et al. ............... 514/2 |
| 6,114,146 A | 9/2000 | Herlitschka et al. ........ 435/69.7 |
| 6,149,911 A | 11/2000 | Binz et al. ................ 424/192.1 |
| 6,165,470 A | 12/2000 | Becquart et al. .......... 424/185.1 |

FOREIGN PATENT DOCUMENTS

| AU | 704594 | 5/1995 |
| CA | 2022539 | 2/1991 |
| CN | 1235981 A | 11/1999 |
| CN | 1239103 A | 12/1999 |
| DE | 37 23 781 A1 | 1/1988 |
| EP | 0 073 646 A2 | 3/1983 |
| EP | 0 079 739 A2 | 5/1983 |
| EP | 0 088 632 A2 | 9/1983 |
| EP | 0 091 527 A2 | 10/1983 |
| EP | 0 116 201 A1 | 8/1984 |

(List continued on next page.)

OTHER PUBLICATIONS

Voet et al. Biochemistry. 1990. John Wiley & Sons, Inc. pp. 126–128 and 228–234.*

(List continued on next page.)

Primary Examiner—Yvonne Eyler
Assistant Examiner—Joseph F. Murphy
(74) Attorney, Agent, or Firm—Finnegan, Henderson, Farabow, Garrett & Dunner L.L.P.

(57) ABSTRACT

Biologically active polypeptides comprising a therapeutically active polypeptide fused to human serum albumin or a variant thereof, methods for the preparation thereof, nucleotide sequences encoding such fusion polypeptides, expression cassettes comprising such nucleotide sequences, self-replicating plasmids containing such expression cassettes, and pharmaceutical compositions containing said fusion polypeptides.

25 Claims, 25 Drawing Sheets

FOREIGN PATENT DOCUMENTS

| | | |
|---|---|---|
| EP | 0 123 294 A1 | 10/1984 |
| EP | 0 123 544 A2 | 10/1984 |
| EP | 0 138 437 A2 | 4/1985 |
| EP | 0 147 198 A3 | 7/1985 |
| EP | 0 163 406 A1 | 12/1985 |
| EP | 0 196 056 B1 | 10/1986 |
| EP | 0 201 239 A1 | 11/1986 |
| EP | 0 206 733 A1 | 12/1986 |
| EP | 0 236 210 A1 | 9/1987 |
| EP | 0 241 435 A2 | 10/1987 |
| EP | 0 244 221 A1 | 11/1987 |
| EP | 0 267 678 A1 | 5/1988 |
| EP | 0 301 670 A1 | 2/1989 |
| EP | 0 308 381 A1 | 3/1989 |
| EP | 0 314 317 A1 | 5/1989 |
| EP | 0 319 641 A1 | 6/1989 |
| EP | 0 322 094 A1 | 6/1989 |
| EP | 0 325 262 A2 | 7/1989 |
| EP | 0 330 451 A2 | 8/1989 |
| EP | 0 344 459 A2 | 12/1989 |
| EP | 0 361 991 A2 | 4/1990 |
| EP | 0 366 400 A2 | 5/1990 |
| EP | 0 395 918 A2 | 11/1990 |
| EP | 0 399 666 B1 | 11/1990 |
| EP | 0 411 678 B2 | 2/1991 |
| EP | 0 413 622 B1 | 2/1991 |
| EP | 0 416 673 A1 | 3/1991 |
| EP | 0 427 189 A1 | 5/1991 |
| EP | 0 286 439 B1 | 1/1992 |
| EP | 0 503 583 A1 | 9/1992 |
| EP | 0 509 841 A2 | 10/1992 |
| EP | 0 510 678 A2 | 10/1992 |
| EP | 0 510 693 A2 | 10/1992 |
| EP | 0 511 912 A1 | 11/1992 |
| EP | 0 364 980 B1 | 4/1993 |
| EP | 0 300 466 B1 | 9/1995 |
| EP | 0 401 384 B1 | 3/1996 |
| EP | 0 711 835 A1 | 5/1996 |
| EP | 0 409 113 B1 | 6/1996 |
| EP | 0 428 267 B1 | 12/1996 |
| EP | 0 771 871 A2 | 7/1997 |
| EP | 0 148 605 B2 | 12/1998 |
| EP | 0 668 351 B1 | 9/1999 |
| FR | 2 635 115 | 9/1990 |
| FR | 2 719 593 | 11/1995 |
| GB | 2 193 631 A | 2/1988 |
| GB | 2 350 362 A | 11/2000 |
| JP | 1 117790 | 5/1989 |
| JP | 2 117384 | 5/1990 |
| JP | 2 227079 | 9/1990 |
| JP | 3 27320 | 2/1991 |
| JP | 3 201987 | 9/1991 |
| JP | 4 211375 | 8/1992 |
| JP | 5 292972 | 11/1993 |
| JP | 6-22784 | 2/1994 |
| JP | 6 38771 | 2/1994 |
| JP | 8-51982 | 2/1996 |
| JP | 8 53500 | 2/1996 |
| JP | 8 59509 | 3/1996 |
| WO | 85/02610 | 6/1985 |
| WO | WO 8503079 * | 7/1985 |
| WO | 86/03520 | 6/1986 |
| WO | WO 87/03887 | 7/1987 |
| WO | WO 89/02922 | 4/1989 |
| WO | WO 90/04788 | 5/1990 |
| WO | WO 90/13653 | 11/1990 |
| WO | WO 91/02754 | 3/1991 |
| WO | 91/05867 | 5/1991 |
| WO | WO 91/08220 | 6/1991 |
| WO | WO 93/00109 | 1/1993 |
| WO | WO 93/00437 | 1/1993 |
| WO | WO 93/03164 | 2/1993 |
| WO | WO 93/15199 | 8/1993 |
| WO | WO 93/15200 | 8/1993 |
| WO | WO 93/15211 | 8/1993 |
| WO | WO 94/25489 | 11/1994 |
| WO | WO 95/23857 | 9/1995 |
| WO | WO 95/27059 | 10/1995 |
| WO | WO 95/30759 | 11/1995 |
| WO | WO 96/03144 A1 | 2/1996 |
| WO | WO 96/08512 | 3/1996 |
| WO | WO 96/14409 | 5/1996 |
| WO | WO 96/14416 | 5/1996 |
| WO | WO 96/18412 | 6/1996 |
| WO | WO 97/24445 | 7/1997 |
| WO | WO 97/34997 | 9/1997 |
| WO | WO 97/39132 | 10/1997 |
| WO | WO 98/04718 | 2/1998 |
| WO | WO 98/36085 | 8/1998 |
| WO | WO 99/00504 | 1/1999 |
| WO | WO 99/13914 | 3/1999 |
| WO | WO 99/15193 | 4/1999 |
| WO | WO 99/66054 | 12/1999 |
| WO | WO 00/04171 | 1/2000 |
| WO | WO 00/23459 | 4/2000 |
| WO | WO 00/44772 | 8/2000 |

OTHER PUBLICATIONS

Weitkamp LR et al., Ann Hum Genet. 37:219–226 (1973).

Minchiotti L et al., Biochimica et Biophysica Acta 1119:232–238 (1992).

Galliano M. et al., FEBS Letters 208:364–368 (1986).

Galliano M. et al., FEBS Letters 233:100–104 (1988).

Galliano M. et al., Proc. Natl. Acad. Sci. USA 87:8721–8725 (1990).

Galliano M. et al., J. Biol. Chem. 261:4283–4287 (1986).

Weitkamp LR et al., Ann. Hum. Genet. 36:381–392 (1973).

Peters T. Clin. Chem. 23:5–12 (1977).

Hershfield MS et al., Proc. Natl. Acad. Sci. USA 88:7185–7189 (1991).

Reed, R.G., et al., "Non–Resolving Jaundice: Bilirubin Covalently Attached to Serum Albumin Circulates With the Same Metabolic Half–Life as Albumin," Clin. Chem. 34:1992–1994 (1988).

Abastado, J–P., et al., "A Soluble, Single Chain $K^d$ Molecule Produced by Yeast Selects a Peptide Repertoire Indistinguishable from that of Cell–surface–associated $K^d$," Eur. J. Immunol., 23:1776–1783 (1993).

Ahluwalia, M., et al., "Isolation and Characterization of an Anticryptococcal Protein in Human Cerebrospinal Fluid," J. Med. Microbiol. 50:83–89 (2001).

Akiyama, Y., et al., "Characterization of a Human Blood Monocyte Subset with Low Peroxidase Activity," The Journal of Clinical Investigation 72:1093–1105 (1983).

Anonymous, "Use of Recombinant Human Albumin in the Formulation of Proteins," Research Disclosure, 516 Aug. 1995.

Anspach, F.B., et al., "High–Performance Liquid Chromatography of Amino Acids, Peptides and Proteins," Journal of Chromatography 476:205–225 (1989).

Armstrong, J.D., et al., "Active Immunization of Pigs Against Growth Hormone–Releasing Factor: Effect on Concentrations of Growth Hormone and Insulin–Like Growth Factor," J. Anim. Sci. 68:427–434 (1990).

Armstrong, J.D., et al., "Concentrations of Hormones and Metabolites, Estimates of Metabolism, Performance, and Reproductive Performance of Sows Actively Immunized Against Growth Hormone–Releasing Factor," *J. Anim. Sci.* 72:1570–1577 (1994).

Armstrong, J.D., et al., "Effect of Feed Restriction on Serum Somatotropin, Insulin–Like Growth Factor–I–(IGF–I) and IGF Binding Proteins in Cyclic Heifers Actively Immunized Against Growth Hormone Releasing Factor," *Domestic Animal Endocrinology* 10:315–324 (1993).

Armstrong, J.D., et al., "Endocrine Events Prior to Puberty in Heifers: Role of Somatotropin, Insulin–Like Growth Factor–1 and Insulin–Like Growth Factor Binding Proteins," *Journal of Physiology and Pharmacology* 43:179–183 (1992).

Armstrong, J.D., et al., "Opiod Control of Growth Hormone in the Suckled Sow is Primarily Mediated Through Growth Hormone Releasing Factor," *Domestic Animal Endocrinology* 7:191–198 (1990).

Asenjo, J.A., et al., "Design of Enzyme Systems for Selective Product Release from Microbial Cells; Isolation of a Recombinant Protein from Yeast," *Annals of the New York Academy of Sciences* 542:140–152 (1988).

Avery, R.A., et al., "Structural Integrity of the Human Albumin Gene in Congenital Analbuminemia," *Biochemical and Biophysical Research Communications* 116:817–821 (1983).

Azar, D.T. et al., "Corneal Topographic Evaluation of Decentration in Photorefractive Keratectomy: Treatment Displacement vs Intraoperative Drift," *American Journal of Opthalmology* 124:312–320 (1997).

Ballance, D.J., "Sequence Important for Gene Expression in Filamentous Fungi," *Yeast* 2:229–236 (1986).

Ballance, D.J., "Yeast–Derived Recombinant Human Albumin (Recombumin™)," *Anasthesiol. Intensivmed. Notfallmed. Schmerzther* 34:775–777 (1999).

Ballance, D.J., et al., "A Hybrid Protein of Urokinase Growth–Factor Domain and Plasminogen–Activator Inhibitor Type 2 Inhibits Urokinase Activity and Binds to the Urokinase Receptor," *Eur. J. Biochem,* 207:177–183 (1992).

Ballance, D.J., et al., "Development of a High–frequency Transforming Vector for *Aspergillus Nidulans,*" *Gene* 36:321–331 (1985).

Ballance, D.J., et al., "Gene Cloning in *Aspergillus Nidulans*: Isolation of the Isocitrate Lyase Gene (acuD)," *Mol. Gen. Genet.* 202:271–275 (1986).

Ballance, D.J., et al., "Transformation of *Aspergillus Nidulans* by the Orotidine–5'Phosphate Decarboxylase Gene of Neurospora Crassa," *Biochemical and Biophysical Research Communications* 112:284–289 (1983).

Ballay, A., et al., "In vitro and in vivo Synthesis of the Hepatitis B Virus Surface Antigen and of the Receptor for Polymerized Human Serum Albumin from Recombinant Human Adenoviruses," *The Embo Journal* 4:3861–3865 (1985).

Barash I., et al., "Elements with the β–Lactoglobulin Gene Inhibit Expression of Human Serum Albumin cDNA and Minigenes in Transfected Cells but Rescue their Expression in the Mammary Gland of Transgenic Mice," *Nucleic Acids Research* 24:602–610 (1996).

Barash, I., et al., "Co–integration of β–Lactoglobulin/Human Serum Albumin Hybrid Genes with the Entire β–Lactoglobulin Gene or the Matrix Attachment Region Element: Repression of Human Serum Albumin and β–Lactoglobulin Expression in the Mammary Gland and Dual Regulation of the Transgenes," *Molecular Reproduction and Development* 45:421–430 (1996).

Barash, I., et al., "Ectopic Expression of β–Lactoglobulin/Human Serum Albumin Fusion Genes in Transgenic Mice: Hormonal Regulation and in situ Localization," *Transgenic Research* 3:141–151 (1994).

Barash, I., et al., "In Vivo and In Vitro Expression of Human Serum Albumin Genomic Sequences in Mammary Epithelial Cells With β–Lactoglobulin and Whey Acidic Protein Promoters", *Molecular Reproduction and Development* 52:241–252 (1999).

Barash, I., et al., "Synthesis and Secretion of Human Serum Albumin by Mammary Gland Explants of Virgin and Lactating Transgenic Mice," *Transgenic Research* 2:266–276 (1993).

Barb, C.R., et al., "Aspartate and Glutamate Modulation of Growth Hormone Secretion in the Pig: Possible Site of Action," *Domestic Animal Endocrinology* 13:81–90 (1996).

Barker, W.C., et al., "Continuous Intraoperative External Monitoring of Perfusate Leak Using Iodine–131 Human Serum Albumin During Isolated Perfusion of the Liver and Limbs," *European Journal of Nuclear Medicine* 22:1242–1248 (1995).

Baruch, A., et al., "Insulin and Prolactin Synergize to Induce Translation of Human Serum Albumin in the Mammary Gland of Transgenic Mice," *Transgenic Research* 7:15–27 (1998).

Beattie, W.G., et al., "Structure and Evolution of Human α–fetoprotein Deduced from Partial Sequence of Cloned cDNA," *Gene* 20:415–422 (1982).

Becquart, J., "Les Syncopes ou Malaises D'Origine Vasulaire," *Soins,* 504:4–8 (1987), with English translation.

Becquart, J., et al., "Pronostic du Syndrome de Wolff–Parkinson–White chez le Nourrisson," *Arch. Mal. Coeur* 81:695–700 (1988), with English translation.

Becquart, J., et al., "Insuffisance Aortique Argue Rhumatoide Traitee Par un Remplacement Valvulaire," *Arch. Mal. Coeur* 84:987–989 (1991), with English translation.

Becquart, J., et al., "Les Pheochromocytomes Malins," *Annales De Cardiologie Et D'Andeliologie,* 36:191–196 (1987), with English translation.

Beitins I.Z., et al., "Conversion of Radiolabeled Human Growth Hormone into Higher Molecular Weight Moieties in Human Plasma in Vivo and in Vitro," *Endocrinology* 101:350–359 (1977).

Benda, V., et al., "Assessment of Lymphocyte and Phagocytic Functions in Goats Treated with Glucan," *J. Vet. Med.* 38:681–684 (1991).

Benihoud, K., "Efficient, Repeated Adenovirus–Mediated Gene Transfer in Mice Lacking both Tumor Necrosis Factor Alpha and Lymphotoxin α," *Jour. of Virology* 72:9514–9525 (1988).

Benihoud, K., et al., "Adenovirus Vectors for Gene Delivery," *Current Opinion in Biotechnology* 10:440–447 (1999).

Bera T.K., et al., "Comparison of Recombinant Immunotoxins Against Le$^y$ Antigen Expressing Tumor Cells: Influence of Affinity, Size, and Stability," *Bioconjugate Chem.* 9:736–743 (1998).

Berger, E.A., et al., "A Soluble Recombinant Polypeptide Comprising the Amino–Terminal Half of the Extracellular Region of the CD4 Molecule Contains as Active Binding Site for Human Immunodeficiency Virus," *Proc. Natl. Acad. Sci. USA* 85:2357–2361 (1988).

Bettany, A.J.E., et al., "5'–Secondary Structure Formation, in Contrast to a Short String of Non–Preferred Codons, Inhibits the Translation of the Pyruvate Kinase mRNA in Yeast," *Yeast* 5:187–198 (1989).

Beydon, M–H., et al., "Microbiological High Throughput Screening: An Opportunity for the Lead Discovery Process," *Jour. of Biomolecular Screening* 5:13–21 (2000).

Bian, Z., et al., "Glycated human serum albumin induces IL–8 and MCP–1 gene expression in human corneal keratocytes," *Current Eye Research* 2117:65–72 (1998).

Bian, Z., et al., "Synergy between Glycated Human Serum Albumin and Tumor Necrosis Factor–α for Interleukin–8 Gene Expression and Protein Secretion in Human Retinal Pigment Epithelial Cells," *Laboratory Investigation* 78:355–344 (1998).

Bian, Z–M., et al., "GlycatedSerum Albumin Induces Chemokine Gene Expression in Human Retinal Pigment Epithelial Cells," *Jour. of Leukocytes Biology* 60:405–414 (1996).

Bietlot, H.P., et al., "Analysis of Recombinant Human Erythropoietin in Drug Formulations by High–Performance Capillary Electrophoresis," *Journal of Chromatography A* 759:177–184 (1997).

Billard, P., et al., "Isolation and Characterization of the Gene Encoding Xylose Reductase from *Kluyveromyces lactis*," *Gene* 162:93–97 (1995).

Blondeau, K., et al., "Physiological Approach to Heterologous Human Serum Albumin Production by *Kluyveromyces lactis* in Chemostat Culture," *Yeast* 10:1297–1303 (1994).

Boado, R.J., et al., "Complete Inactivation of Target mRNA by Biotinylated Antisense Oligodeoxynucleotide—Avidin Conjugates," *Bioconjugate Chem.* 5:406–410 (1994).

Bobak, D.A., et al., "C1q Enhances the Phagocytosis of *Cryptococcus neoformans* Blastospores by Human Monocytes," *The Journal of Immunology* 141:592–597 (1988).

Boddy, L.M., et al., "Purification and Characterization of an *Aspergillus niger* invertase and its DNA sequence," *Current Genetics* 24:60–66 (1993).

Boland, A., et al., "Adenoviruses–Mediated Transfer of the Thyroid Sodium/Iodide Symporter Gene into Tumors for a Targeted Radiotherapy," *Cancer Research* 60:3484–3492 (2000).

Bolognesi, D.P., et al., "Progress in Vaccines Against AIDS," *Science* 1233–1234 (1989).

Boyle, M.D.P., et al., "Characterization of a Gene Coding for a Type llo Bacterial IgG–Binding Protein," *Molecular Immunology* 32:669–678 (1995).

Bramanti, T.E., et al., "Effect of Porphyrins and Host Iron Transport Proteins on Outer Membrane Protein Expression in *Porphyromonas* (Bacteroides) *Gingivalis*: Identification of a Novel 26 kDa Hemin–Repressible Surface Protein," *Microbial Pathogenesis* 13:61–73 (1992).

Braun, A., et al., "Protein Aggregates Seem to Play a Key Role Among the Parameters Influencing the Antigenicity of Interfero Alpha (IFN–α) in Normal and Transgenic Mice," *Pharmaceutical Research* 14:1472–1478 (1997).

Brennan S.O., et al., "Albumin Redhil (−1 Arg, 320 Ala→Thr): A Glycoprotein Variant of Human Serum Albumin Whose Precursor has an Aberrant Signal Peptidase Cleavage Site," *Proc. Natl. Acad. Sci. USA* 87:26–30 (1990).

Breton, J., et al., "Prolonged Half–Line in the Circulation of a Chemical Conjugate Between a Pro–Urokinase Derivative and Human Serum Albumin," *Eur. J. Biochem.* 231:563–569 (1995).

Brito, B. E., et al., "Murine endotoxin–induced uveitis, but not immune complex–induced uveitis, is dependent on the IL–8 receptor homolog," *Current Eye Research* 19:76–85 (1999).

Broide, R.S., et al., "Manipulations of ACHE Gene Expression Suggest Non–Catalytic Involvement of Acetylcholinesterase in the Functioning of Mammalian Photoreceptors but not in Retinal Degeneration," *Molecular Brain Research*, 71:137–148 (1999).

Brown, J.R., et al., "Serum Albumin: Structure and Characterization of Its Ligand Binding Sites," in *Lipid–Protein Interactions* vol. 1, ed. P.C. Jost,2:25–68 (1982).

Brown, N.P., et al., "Identification and Analysis of Multigene Families by Comparison of Exon Fingerprints," *J. Mol. Biol.* 249:342–359 (1995).

Budkowska, A., et al., "Hepatitis B Virus Pre–S Gene–Encoded Antigenic Specificity and Anti–Pre–S Antibody: Relationship between Anti–Pre–S Response and Recovery," *Hepatology* 6:360–368 (1986).

Budkowska, A., et al., "Monoclonal Antibody Recognizing Pre–S(2) Epitope of Hepatitis B Virus: Charachterization of PreS(2) Antibody," *Jour. of Medical Virology* 20:111–125 (1986).

Cai, M. et al., "Development and Application of Hybridoma Secreting Monoclonal Antibody Against Poly–Human Serum Albumin" *J. WCUMS* 20(2):134–136 (1989), with English translation.

Capon, D.J. et al., "Designing CD4 Immunoadhesins for AIDS Therapy," *Nature* 337:525–531 (1989).

Caron, M. et al., "Ultraviolet Difference Spectroscopy Study of Peanut Lectin Binding to Mono–and Disaccharides," *Biochimica et Biophysica Acta*, 717:432–438 (1982).

Carter, A.P., et al., "Preparation and Properties of Monoclonal Antibodies to the Anabolic Agent Zeranol," *J. Vet. Pharmacol. Therap.* 7:17–21 (1984).

Carter, B.L.A., et al., "Secretion of Mammalian Polypeptides from Yeast," *Microbiological Sciences* 3:23–27 (1986).

Cassidy, J., et al., "The Importance of Added Albumin During Continuous Intravenous Infusion of Interleukin–2 with Alpha–interferon," *Eur. J. Cancer* 27:1633–1634 (1991).

Chang, S–P., et al., "Hormonal Profiles in the Luteal Phase and First Trimester of Pregnancies Arising From in Vitro Fertilization," *Chin. Med. J.* 39:255–262 (1987).

Chang, T–T., et al., "Clinical Significance of Serum Type–III Procollagen Aminopropeptide in Hepatitis B Virus–Related Liver Diseases," *Scandinavian Jour. of Gastroenterology* 24:533–538 (1989).

Charbit, A., et al., "Presentation of Two Epitopes of the preS2 Region of Hepatitis B virus on Live Recombinant Bacteria," *The Jour. of Immunology* 139:1658–1664 (1987).

Charlton, B., et al., "Th1 Unresponsiveness can be Infectious for Unrelated Antigens," *Immunology and Cell Biology* 76:173–178 (1998).

Chen, M–F., et al., "Effects of Dietary Supplementation with Fish Oil on Prostanoid Metabolism During Acute Coronary Occlusion with our without Reperfusion in diet–Induced Hypercholesterolemic Rabbits," *International Jour. of Cardiology* 36:297–301 (1992).

Chen, M–F., et al., "Effects of Dietary Supplementation with Fish Oil on Atherosclerosis and Myocardial Injury During Acute Coronary Occlusion–reperfusion in Diet–Induced Hypercholesterolemic Rabbits," *International Jour. of Cardiology* 35:323–331 (1992).

Chen, Y–M., "Pulmonary Nocardiosis with Cerebral Abscess Successfully Treated by Medication Alone—A Case Report," *Chin. Med. J. (Taipei)* 47:294–298 (1991), with English translation.

Chen, Y–M., et al., "Neurofibromatosis with Interstitial Pulmonary Fibrosis—Gene Report and Literature Review," *Chin. Med. J. (Taipei)* 42:213–218 (1988), with English translation.

Chen, Z., et al., "Enhancing the Immunogenicity of the preS Antigen of Hepatitis B Virus by Genetically Fusing it with Interleukin–2," *Natl. Med. J. China* 76(1):34–37 (1996), with English translation.

Clark, R., et al., "Long–Acting Growth Hormone Produced by Conjugation with Polyethylene Glycol," *Jour. of Biolog. Chem.*, 271(36):21969–21977 (1996).

Clement, J–M., et al., "Proprietes Neutralisantes pour les virus HIV d'une Proteine Hydride Ma11–CD4 Exprimee chez *E. coli* et Purifiable en une Etape," *C.R. Acad.Sci. Paris* 308:401–406 (1989).

Clerc, F.F., et al., "Primary Structure Control of Recombinant Proteins Using High–Performance Liquid Chromatography, Mass Spectrometry and Microsequencing," *Jour. of Chromatography B: Biomedical Applications* 662:245–259 (1994).

Cobb, R.R., et al., "Interleukin–1β Expression is Induced by Adherence and is Enhanced by Fc–receptor Binding to immune Complex in THP–1 Cells," *FEBS Letters* 394:241–246 (1996).

Cohick, W.S., et al., "Ovarian Expression of Insulin–Like Growth Factor–I (IGF–I), IGF Binding Proteins, and Growth Hormone (GH) Receptor in Heifers Actively Immunized Against GH–Releasing Factor*", *Endocrinology* 137:1670–1677 (1996).

Coles, G.A., et al., "Estimation of Erythropoietin Secretion Rate in Normal and Uremic Subjects," *American Journal of Physiology* 263:F939–F944 (1992).

Contreras, R., et al., "Efficient KEX–2 Like Processing of a Glucoamylase–Interleukin–6 Fusion Protein by *Aspergillus Nidulans* and Secretion of Mature Interleukin–6," *Bio/Technology* 9:378–381 (1991).

Cornford, E.M., et al., "High Expression of the Glut1 Glucose Transporter in Human Brain Hemangioblastoma Endothelium," *Jour. of Neuropathology and Experimental Neurology* 54:842–851 (1995).

Costa, S.K.P., et al., "Involvement of Vanilloid Receptors and Purinoceptors in the *Phoneutria nigriventer* Spider Venom–induced Plasma Extravasation in Rat Skin," *Eur. Jour. of Pharmacology* 391:305–315 (2000).

Cox, H., et al., "Constitutive Expression of Recombinant Proteins in the Methylotropic Yeast Hansenula Polymorpha Using the PMAI Promoter," *Yeast* 16:1191–1203 (2000).

Crouzet, J., et al., "Recombinational Construction in *Escherichia coli* of Infectious Adenoviral Genomes," *Proc. Natl. Acad. Sci. USA* 94:1414–1419 (1997).

Cullen, D., et al., "Sequence and Centromere Proximal location of a Transformation enhancing fragment ans1 from *Aspergillus nidulans*," *Nucleic Acids Research* 15:9163–9175 (1987).

Cunningham, B.C. et al., "Dimerization of the Extracellular Domain of the Human Growth Hormone Receptor by a Single Hormone Molecule," *Science* 254:821–825 (1991).

Dang, C.V., et al., "Identification of the Human c–myc Protein Nuclear Translocation Signal," *Molecular and Cellular Biology* 8:4048–4054 (1988).

Darlington, G.J., et al., "Human Serum Albumin Phenotype Activation in Mouse Hepatoma–Human Leukocyte Cell Hybrids," *Science* 185:859–862 (1974).

de Chateau, M., et al., "Protein PAB, A Mosaic Albumin–binding Bacterial Protein Representing the First Contemporary Example of Module Shuffling," *The Jour. of Biological Chemistry* 269:12147–12151 (1994).

de Chateau, M., et al., "Protein PAB, an Albumin–binding Bacterial Surface Protein Promoting Growth and Virulence*", *The Jour. of Biological Chemistry* 271:26609–26615 (1996).

De Vos, A.M. et al., "Human Growth Hormone and Extracellular Domain of its Receptor: Crystal Structure of the Complex," *Science* 255:306–312 (1992).

Dedieu, J–F., et al., "Long–Term Gene Delivery into the Livers of Immunocompetent Mice with E1/E4–Defective Adenoviruses," *Journal of Virogy* 71:4626–4637 (1997).

Dehoux, P., et al., "Expression of the Hepatitis B Virus Large Envelope Protein in *Saccharomyces cerevisiae*," *Gene* 48:155–163 (1986).

DeMeyer, S., et al., "Organ and species specificity of hepatitis B virus (HBV) infection: a review of literature with a special reference to preferential attachment of HBV to human hepatocytes," *Journal of Viral Hepatitis* 4:145–153 (1997).

Dmitrenko, V.V., et al., "Heterogeneity of the Polyadenylation Site of mRNA Coding for Human Serum Albumin," *Genetika* 26(4):765–769 (1990), with English translation.

Dockal, M., et al., "The Three Recombinant Domains of Human Serum Albumin," *The Jour. of Biological Chemistry* 274:29303–29310 (1999).

Dodsworth, N., et al., "Comparative Studies of Recombinant Human Albumin and Human Serum Albumin Derived by Blood Fractionation," *Biotechnol. Appl. Biochem.* 24:171–176 (1996).

Doyen, N., et al., "Immunochemical Cross–Reactivity Between Cyanogen Bromide Fragments of Human Serum Albumin," *The Journal of Biological Chemistry* 257:2770–2774 (1982).

Earl, R.T., et al., "Evaluation of Reconstituted Sendai Virus Envelopes as Intra–articular Drug Vectors: Effects on Normal and Experimentally Arthritic Rabbit Knee Joints," *Jour. Pharm. Pharmacol.* 40:166–170 (1988).

Eliasson, M., et al., "Structural and Functional Analysis of the Human IgG–Fab Receptor Activity of Streptococcal Protein G*", *Molecular Immunology* 28:1055–1061 (1991).

Embleton, M.J. et al., "Unsuitability of Monoclonal Antibodies to Oncogene Proteins for Anti–Tumor Drug–Targeting," *Int. J. Cancer* 38:821–827 (1986).

Erhard, M.H., et al., "Adjuvant Effects of Various Lipopeptides and Interferon–γ on the Humoral Immune Response of Chickens," *Poultry Science* 79:1264–1270 (2000).

Etcheverry, T., et al., "Regulation of the Chelatin Promoter During the Expression of Human Serum Albumin or Yeast Phosphoglycerate Kinase in Yeast," Bio/Technology 4:726–730 (1986).

Faerman, A., et al., "Dramatic Heterogeneity of Transgene Expression in the Mammary Gland of Lactating Mice: A Model System to Study the Synthetic Activity of Mammary Epithelial Cells," The Jour. of Histochemistry and Cytochemistry 43:461–470 (1995).

Falkenberg, C., et al., "Purification of Streptococcal Protein G Expressed by Escherichia coli by High Performance Liquid Affinity Chromatography Using Immobilized Immunoglobulin G and Albumin," Biomedical Chromatography 2:221–225 (1987).

Farese, A.M., et al., "Therapeutic Efficacy of Recombinant Human Leukemia Inhibitory Factor in a Primate Model of Radiation–Induced Marrow Aplasia," Blood 84:2675–3678 (1994).

Fedorchenko, S.V., et al., "Is it Possible to Overcome Resistance of Patients with Chronic Hepatitis B to Antiviral Therapy Because of Production of Antibodies to Recombinant $\alpha-_2$–Interferon?" Voporsy Virusologii 5:218–220 (1994), with English translation.

Felten, D. L. et al., "Sympathetic Innervation of Lymph Nodes in Mice," Brain Research Bullentin 13:693–699 (1984).

Finnis, C., et al., "Expression of Recombinant Platelet–Derived Endothelial Cell Growth Factor in the Yeast Saccharomyces cerevisiae," Yeast, 8:57–60 (1992).

Fitos, I., et al., "Binding Studies with Recombinant Human Serum Albumin Obtained by Expression of a Synthetic Gene in Yeast," Biochemical Pharmacology 46:1159–1163 (1993).

Fleer, R. E., "Speed of Movement Under Two Conditions of Response–Initiation in Retardates," Perceptual and Motor Skills 35:140–142 (1972).

Fleer, R., "Engineering Yeast for High Level Expression," Current Opinion in Biotechnogy 3:486–496 (1992).

Fleer, R., et al., "Formation and Fate of Cross–links induced by Polyfunctional Anticancer Drugs in Yeast," Molec.Gen. Genet. 176:41–52 (1979).

Fleer, R., et al., "High–Level Secretion of Correctly Processed Recombinant Human Interleukin–1β in Kluyveromyces Lactis," Gene 107:285–295 (1991).

Fleer, R., et al., "RAD4 Gene of Saccharomyces cerevisiae: Molecular Cloning and Partial Characterization of a Gene That Is Inactivated in Escherichia coli," Molecular and Cellular Biology 7:1180–1192 (1987).

Fleer, R., et al., "Stable Multicopy Vectors for High–ILvel Secretion of Recombinant Human Serum Albumin by Kluyveromyces Yeasts," Bio/Technology 9:968–975 (1991).

Fleer, R., et al., "The Cytotoxic Action of Activated and Non–Activated Cyclophosphamide in Yeast Comparison of Induced DNA Damage," Chem.–Biol. Interactions 42:67–78 (1982).

Fleer, R., et al., "Toxicity, Interstrand Cross–Links and DNA Fragmentation Induced by 'Activated' Cyclophosphamide in Yeast," Chem.–Biol. Interactions 37:123–140 (1981).

Fleer, R., et al., "Toxicity, Interstand Cross–Links and DNA Fragmentation Induced by 'Activated' Cyclophosphamide in Yeast: Comparative Studies on 4–Hydroperoxy–Cyclophosphamide, its Monofunctional Analogon, Acrolein, Phosphoramide Mustard, and Nor–Nitrogen Mustard," Chem.–Biol. Interations 39:1–15 (1982).

Fleer, R., et al., "Mutational Inactivation of the Saccharomyces cerevisiae RAD4 Gene in Escherichia coli," Jour. of Bacterilogy 169:4884–4892 (1987).

Fournier, A., et al., "The Primary Structure of the 3–Phosphoglycerate Kinase (PGK) Gene from Kluyveromyces Lactis," Nucleic Acids Research 18:365 (1989).

Franco, A.A., et al., "Cloning and Characterization of dnaE, Encoding the Catalytic Subunit of Replicative DNA Polymerase III, from Vibrio Cholerae Strain C6706," Gene 175:281–283 (1996).

Friedberg, E.C., et al., "Molecular Approaches to the Study of Nucleotide Excision Repair in Eukaryotes," in Mechanisms of DNA Damage and Repair, Plenum Press New York and London (1986).

Friedberg, E.C., et al., "Nucleotide Excision Repair Genes From the Yeast Saccharomyces Cerevisiae," in Antimutagenesis and Anticarincogenesis Mechanisms, Plenum Press, New York and London (1986).

Fujisawa, Y., et al., "Expression of Hepatitis B Virus Surface Antigen P31 Gene in Escherichia coli," Gene 40:23–29 (1985).

Fujiwara, K., et al., "Monoclonal Antibody Against the Glutaraldehyde–Conjugated Polyamine, Spermine," Hisochem. Cell Biol. 104:309–316 (1995).

Fukuda, M., et al., "Interaction Between Human Albumin Polymers and the Envelope Polypeptide of Hepatitis B Virus (P31) Containing the Translation Product of the Pre–S2 Region," J. of Exp. Med (Japan) 57:125–129 (1987).

Gainey, L.D.S., et al., "Characterization of the glyoxysomal isocitrate Lyase Genes of Aspergillus nidulans (acuD) and Neurospora crassa (acu–3)," Current Genetics 21:43–47 (1992).

Galliano, M., et al., "Genetic Variants Showing Apparent Hot–Spots in the Human Serum Albumin Gene," Clinica Chimica Acta 289:45–55 (1999).

Galliano, M., et al., "Mutations in Genetic Variants of Human Serum Albumin Found in Italy," Proc. Natl. Acad. Sci. USA 87:8721–8725 (1990).

Galliano, M., et al., "Protein and DNA Sequence Analysis of a 'Private' Genetic Variant: Albumin Ortonovo (Glu–505→Lys)," Biochimica et Biophysica Acta 1225:27–32 (1993).

Galliano, M., et al., "Structural Characterization of a Chain Termination Mutant of Human Serum Albumin," The Journal of Biological Chemistry 261:4283–4287 (1986).

Galliano, M., et al., "The Amino Acid Substitution in Albumin Roma: 321 Glu→Lys," FEB 233:100–104 (1988).

Galliano, M., et al., "The Molecular Defect of Albumin Tagliacozzo: 313→Asn," FEBS 208:364–368 (1986).

Gao, J–X., et al., "The Effect of Ebselen of Polymorphonuclear Leukocyte and Lymphocyte Migration to Inflammatory Reactions in Rats," Immunopharmacology 25:239–251 (1993).

Geigert, J., et al., "Potency Stability of Recombinant (Serine–17) Human Interferon–β," Journal of Interferon Research 7:203–211 (1987).

Geisow, M.J., et al., "Large Fragments of Human Serum Albumin," Biochem. J. 161:619–625 (1977).

Geisow, M.J., et al., "Physical and Binding Properties of Large Fragments of Human Serum Albumin," Biochem., J.163:477–484 (1977).

Gerken, G., et al., "Pre–S Encoded Surface Proteins in Relation to the Major Viral Surface Antigen to the Major Viral Surface Antigen in Acute Hepatitis B Virus Infection," Gastroenterology 92:1864–1868 (1987).

Gerken, G., et al., "Virus–Associated Receptors for Polymerized Human Serum albumin (RpHSA) in Patients with Chronic Active Hepatitis b Treated with Recombinant Leukocyte A Interferon," *Digestion* 37:96–102 (1987).

Geyer, A., et al., "M Protein of a *Streptococcus Dysgalactiae* Human Wound Isolate Shows Multiple Binding to Different Plasma Proteins and Shares Epitopes with Keratin and Human Cartilage," *FEMS Immunology and Medical Microbiology* 26:11–24 (1999).

Ghandehari, H., et al., "Size–Dependent Permeability of Hydrophilic Probes Across Rabbit Colonic Epithelium," *The Jour. of Pharmacology and Experimental Therapeutics* 280:747–753 (1997).

Gijsens, M., et al., "Characterization of Human Serum Albumin Heterogeneity by Capillary Zone Electrophoresis and Electrospray Ionization Mass Spectrometry," *Journal of Chromatography A* 772:235–242 (1997).

Goodey, A.R., "The Production of Heterologous Plasma Proteins," *Trends in Biotechnology*, Reference Edition, 11:430–433 (1993).

Gordon, R.D., et al., "Purification and Characterization of Endogenous Peptides Extracted from HLA–DR isolated from the Spleen of a Patient with Rheumatoid Arthritis," *Eur. J. Immunol.* 25:1473–1476 (1995).

Gould, J. E., et al., "What functions of the sperm cell are measured by in vitro fertilization of zona–free hamster eggs?", *Fertility and Sterility* 40:344–352 (1983).

Graslund, T., et al., "Charge Engineering of a Protein Domain to Allow Efficient Ion–exchange Recovery," *Protein Engineering* 13:703–709 (2000).

Grebenyuk, V.N., et al., "Investigation of Safety, Reactivity and Therapeutic Efficacy of Ointment Containing Porcine Leukocytic Interferon," *Antibiotiki* 3:145–149 (1981), with English translation.

Griscelli, F., et al., "Angiostatin Gene Transfer: Inhibition of Tumor Growth In Vivo by Blockage of Endothelial Cell Proliferation Associated with a Mitosis Arrest," *Proc. Natl. Acad. Sci, USA* 95: 6367–6372 (1998).

Griscelli, F., et al., "Combined Effects of Radiotherapy and Angiostatin Gene Therapy in Glioma Tumor Model," *PNAS* 97:6698–6703 (2000).

Guilloteau, J.P., et al., "Purification, Stabilization, and Crystallization of a Modular Protein: Grb2," *Proteins: Structure, Function, and Genetics* 25:112–119 (1996).

Guo–Fen, T., et al., "Isolation and Characterization of Genes for Blood Proteins," *Develop. Biol. Standard* 67:177–183 (1987).

Haffner, D., et al., "Metabolic Clearance of Recombinant Human Growth Hormone in Health and Chronic Renal Failure," *The Journal of Clinical Investigation* 93:1163–1171 (1994).

Hammerberg, B., et al., "Dual Affinity Fusion Approach and its Use to Express Recombinant Human Insulin–Like Growth Factor II," *Proc. Natl. Acad. Sci. USA*, 86:4367–4371 (1989).

Hannebicque, G., et al., "Manifestations Cardiaques De La Maladie De Lyme," *Ann. Cardiol. Angelol.* 38:87–90 (1989), with English translation.

Harris, G.J., "High Speed Memory Scanning in Mental Retardates: Evidence for a Central Processing Deficit," *Jour. Exp. Child Psychology*, 17:452–459 (1974).

Harris, G.J., et al., "Recognition Memory for Faces by Retardates and Normals," *Perceptual and Motor Skills* 34:755–758 (1972).

Harris, G.J., et al., "Serial Recognition Memory by Retardates of Half or Whole Faces in Two Orientations," *Perceptual and Motor Skills* 36:476–478 (1973).

Harvey, R.W., et al., "Feedlot Performance, Carcass Characteristics, Hormones, and Metabolites in Steers Activity Immunized Against Growth Hormone–Releasing Factor," *J. Anim. Sci.* 71:2853–2589 (1993).

Hattori, Y., et al., "Glycated Serum Albumin–Induced Nitric Oxide Production in Vascular Smooth Muscle Cells by Nuclear Factor κB–Dependent Transcriptional Activatio of Inducible Nitric Oxide Synthase," *Biomedical and Biophysical Research Communications* 259:128–132 (1999).

Hawkins, J.W., et al., "The Human Serum Albumin Gene: Structure of a Unique Locus," *Gene* 19:55–58 (1982).

Hedgpeth, J., et al., "DNA Sequence Encoding the $NH_2$–Terminal Peptide Involved in Transport of λ Receptor, and *Escherichia coli* Secretory Protein," *Proc. Natl. Acad. USA* 77:2621–2625 (1980).

Hellstrom, U.B., et al., "Regulation of the Immune Responses to Hepatitis B Virus and Human Serum Albumin. III. Induction of Anti–Albumin Antibody Secretion In Vitro by C–Gene–Derived Proteins in Peripheral B Cells from Chronic Carriers of HBsAg," *Scand. J. Immunol.* 35:53–62 (1992).

Hess, G., et al., "The Effect of Recombinant α–Interferon Treatment on Serum Levels of Hepatitis B Virus–Encoded Proteins in Man," *Hepatology* 7:704–708 (1987).

Hiramatsu, R., et al., "Isolation and Characterization of Human Pro–Urokinase and its Mutants Accumulated within the Yeast Secretory Pathway," *Gene* 99:235–241 (1991).

Hiramatsu, R., et al., "The Prepro–Peptide of Mucro Rennin Directs the Secretion of Human Growth Hormone by *Saccharomyces cerevisiae*," *Applied and Environmental Microbiology* 56:2125–2132 (1990).

Hiramatsu, R., et al., "The Secretion of *Mucro pusillus* Rennin Which Possesses an Artificial Lys–Arg Sequence Directs the Secretion of Mature Human Growth Hormone by *Saccharomyces cerevisiae*," *Applied and Environmental Microbiology* 57:2052–2056 (1991).

Hishinuma, T., et al., "Separation and Concentration of $\Delta^{17}$–6–Keto–PGG $_{1\alpha}$ Using Monoclonal Antibody to ω–Olefin Structure of Trienoic Prostanoids," *Prostaglandins* 44:329–338 (1992).

Hitzeman, R.A., et al., "Use of Heterologous and Homologous Signal Sequences for Secretion of Heterologous Proteins from Yeast," *Methods in Enzymology* 185:421–441 (1990).

Hochuli E., "Interferon Immunogenicity: Technical Evaluation of Interferon–α2a," *Journal of Interferon and Cytokine Research* 17:S15–S21 (1997).

Hodgkins, M., et al., "Expression of the Glucose Oxidase Gene from *Aspergillus Niger* in *Hansenula Polymorpha* and its Use as a Reporter Gene to Isolate Regulatory Mutations," *Yeast*, 9:625–635 (1993).

Hong, K., et al., "Purification and Characterization of M3 Protein Expressed on the Surface of Group A Streptococcal Type 3 Strain C203," *FEMS Immunology and Medical Microbiology* 12:73–82 (1995).

Hong, T–H., et al., The Production of Polyclonal and Monoclonal Antibodies in Mice Using Novel Immunization Methods, *Jour. of Immunological Methods* 120:151–157 (1989).

Hornof, W.J., et al., "A Client Server Model to Facilitate Creation of a Medical Image Teaching Library," *Jour. of Digital Imaging* 12:132–137 (1999).

Hornoff, W.J., et al., "Development of an Automated 12–8 Bit Conversion Algorithm for Displaying and Archiving Scanned Radiographs," *Veterinary Radiology & Ultrasound* 40:179–182 (1999).

Hsu, Y–H., et al., "Spontaneous and Induced Sister Chromatid Exchanges and Delayed Cell Proliferation in Peripheral Lymphocytes of Bowen's Disease Patients and Matched Controls of Arseniasis–Hyperendemic Villages in Taiwan," *Mutation Research* 386:241–251 (1997).

Hu, S–L., et al., "Protection of Macaques Against SIV Infection by Subunit Vaccines of SIV Envelope Glyprotein gp160," *Science* 255:456–459 (1992).

Huang S–Z., et al., "A Study of Transgenic IFV Cattle with the Human Serum Albumin Gene Integrated," *ACTA Genetic Sinica* 27(7):573–579 (2000), with English translation.

Huang, T. H–M., et al., "Genetic Alternations of Microsatellites on Chromosome 18 in Human Breast Carcinoma," *Diagnostic Molecular Pathology* 4:66–72 (1995).

Huland, E., et al., "In Vivo System to Detect Long–Term Continuous Release of Bioactive Interleukin–2 by Immunopharmacological Depot Preparations in Nude Mice with Human Tumors," *J. Cancer Res. Clin. Oncol.* 121:285–290 (1995).

Hunger, H.–D., et al., "Ultrasensitive Enzymatic Radioimmunoassay Using a Fusion Protein of Protein A and Neomycin Phosphotransferase II in Two–chamber–Well Microtiter Plates," *Analytical Biochemistry* 187:89–93 (1990).

Hurter, T., "Experimental Brain Tumors and Edema in Rats," *Exp. Path.* 26:41–48 (1984).

Hurwitz, D.R., et al., "Specific Combinations of Human Serum Albumin Introns Direct High Level Expression of Albumin in Transfected COS Cells and in the Milk of Transgenic Mice," *Transgenic Research* 3:365–375 (1994).

Hwang, G–S., et al., "Small Bowel Perforation Secondary to Metastatic Pulmonary Carcinoma," *Chin. Med. J. (Taipei)* 41(2):159–164 (1988), with English translation.

Ikeda, H., et al., "Changes in Serum Levels of Hepatitis B virus Markers After Interferon Treatment," *Gastroenterologia Japonica* 24:646–654 (1989).

Ikegaya, K., et al., "Complete Determination of Disulfide Forms of Purified Recombinant Human Serum Albumin, Secreted by the Yeast *Pibia pastoris*," *Anal. Chem.* 69:1986–1991 (1997).

Ilan, N., et al., "Dual Regulation of β–Lactoglobulin/Human Serum Albumin Gene Expression by the Extracellular Matrix in Mammary Cells from Transgenic Mice," *Experimental Cell Research* 224:28–38 (1996).

Ilan, N., et al., "β–Lactoglobulin/Human Serum Albumin Fusion Genes Do Not Response Accurately to Signals from the Extracellular Matrix in Mammary Epithelial Cells from Transgenic Mice," *Experimental Cell Research* 228:146–159 (1996).

Imamura, T., et al., "Expression of Hepatitis B Virus Middle and Large Surface Antigen Genes in *Saccharomyces cerevisiae*," *Journal of Virology* 61:3543–3549 (1987).

Inazu, K., et al., "Freeze–Drying and Quality Evaluation of Protein Drugs," *Develop. Biol. Standard* 74:307–322 (1991).

Itoh, Y., et al., "Expression of Hepatitis B Virus Antigen P31 Gene in Yeast," *Biochemical and Biophysical Research Communications* 138:268–274 (1986).

Jameson, B.A., et al., "Location and Chemical Synthesis of a Binding Site for HIV–1 on the CD4 Protein," *Science* 240:1335–1339 (1988).

Jansen, R.W., et al., "Novel, Negatively Charged, Human Serum Albumins Display Potent and Selective in Vitro Anti–Human Immunodeficiency Virus Type 1 Activity," *Molecular Pharmacology* 44:1003–1007 (1993).

Jansen, R.W., et al., "Potent In Vitro Anti–Human Immundeficiency Virus–1 Activity of Modified Human Serum Albumins," *Molecular Pharmacology* 39:818–823 (1991).

Jarstrand, C., et al., "Fibronectin Increases the Motility, Phagocytosis and NBT (Nitroblue Tetrazolium)–Reduction of Granulocytes," *J. Clin. Lab. Immunol.* 8:59–63 (1982).

Jeong, J–H., et al., "Synthesis, Characterization and Protein Adsorption Behaviors of PLGA/PEG di–block co–polymer Blend Films," *Colloids and Surfaces* 18:371–379 (2000).

Jones, S., et al., "Expression of rat Neuronal Nitric Oxide Synthase in *Saccharomyces cerevisiae*," *Jour of Biotechnology* 48:37–41 (1996).

Jonsson, H., et al., "The Type–III Fc Receptor from *Streptococcus Dysgalactiae* is also an $\alpha_2$–Macroglobulin Receptor," *FEBS* 220:819–826 (1994).

Jung, G., et al., "High–Cell Density Fermentation Studies of Recombinant *Escherichia Coli* Strains Expressing Human Interleukin–1β," *Ann. Inst. Pasteur/Microbiol.* 139:129–146 (1988).

Kagaya, K., et al., "Antigen–Specific Suppression of Antibody Responses by T Lymphocytes Cytotoxic for Antigen-Presenting Cells," *APMIS* 102:439–445 (1994).

Kage, R., et al., "Neurokinin B in a Human Pheochromocytoma Measured with a Specific Radioimmunoassay," *Peptides* 10:713–716 (1989).

Kalman, M., et al., "Synthesis of a Gene for Human Serum Albumin an Its Expression in *Saccharomyces cerevisiae*," *Nucleic Acids Research* 18:6075–6081 (1990).

Kang, H.A., et al., "Proteolytic Stability of Recombinant Human Serum Albumin Secreted in the Yeast *Saccharomyces cerevisiae*," *Appl. Microbiol. Biotechnol.* 53:575–582 (2000).

Katsuragi, S., et al., "Late onset X–linked hydrocephalus with normal cerebrospinal fluid pressure," *Psychiatry and Clinical Neuroscience* 54:487–492 (2000).

Kearns, G.L., et al., "Single and Multiple Dose Pharmacokinetics of Methionyl Growth Hormone in Children with Idiopathic Growth Hormone Deficiency," *Journal of Clinical Endocrinology and Metabolism* 72:1148–1152 (1991).

Keel, B.A., et al., "Purified Human α–fetoprotein Inhibits Follicle–stimulating Hormone–stimulated Estradiol Production by Porcine Granulosa Cells in Culture," *Molecular and Cellular Endocrinology* 94:21–25 (1993).

Kerry–Williams, S.M., et al., "Disruption of the *Saccharomyces cerevisiae* YAP3 Gene Reduces the Proteolytic Degradation of Secreted Recombinant Human Albumin," *Yeast* 14:161–169 (1998).

Kimura, S., et al., "New Enzymatic Assay for Calcium in Serum," *Clinical Chemistry* 42:1202–1205 (1996).

King, TP, et al., "Structural Studies and Organic Ligand-Binding Properties of Bovine Plasma Albumin," *The Journal of Biological Chemistry* 245:6134–6148 (1970).

King, T.P., "Limited Pepsin Digestion of Bovine Plasma Albumin," *Archives of Biochemistry and Biophysics* 156:509–520 (1973).

Kira, T., et al., "Correlation of $^{99m}$Tc–GSA Hepatic Scintigraphy with Liver Biopsies in Patients with Chronic Active Hepatitis Type C," *Radiation Medicine* 17:125–130 (1999).

Kirby, C.J., et al., "Changes in Serum Somatotropin, Somatotropin mRNA, and Serum and Follicular Insulin–Like Growth Factor–I in Response to Feed Restriction in Cows Actively Immunized Against Growth Hormone–Releasing Factor," *J. Anim. Sci.* 71:3033–3042 (1993).

Kircher, M., et al., "Biological and Chemical Effects of Mustard Gas in Yeast," *Mutation Research* 63:273–289 (1979).

Kjeldsen, T., et al., "Secretory Expression of Human Albumin Domains in *Saccharomyces cerevisiae* and Their Binding of Myristic Acid and an Acylated Insulin Analogue," *Protein Expression and Purification* 13:163–169 (1998).

Klonjkowski, B., et al., "A Recombinant E1–Deleted Canine Adenoviral Vector Capable of Transduction and Expression of a Transgene in Human–Derived Cells and In Vivo," *Human Gene Therapy* 8:2103–2115 (1997).

Kobayashi, K., et al., "The Development of Recombinant Human Serum Albumin," *Therapeutic Apheresis* 2:257–262 (1998).

Kobayashi, M., et al., "Characterization of Two Differently Glycosylated Molecular Species of Yeast–derived Hepatitis B Vaccine Carrying the pre–S2 region," *Journal of Biotechnology* 26:155–162 (1992).

Konig, T., et al., "Use of Albumin–binding Domain for the Selective Immobilisation of Recombinant Capture Antibody Fragments on ELISA plates," *Jour. of Immunological Methods* 218:73–83 (1998).

Kuipers, M.E., et al., "Anti–HIV–1 Activity of Combinations and Covalent Conjugates of Negatively Charged Human Serum Albumins (NCAs) and AZT," *Jour. of Drug Targeting* 6:323–335 (1999).

Kurnit, D.M., et al., "Confirmation of the Mapping Assignment of Human Serum Albumin to Chromsome 4 Using a Cloned Human Albumin Gene," *Cytogenet. Cell Genet.* 34:282–288 (1982).

Kuroda, S., et al., "*Saccharomyces Cerevisiae* can Release Hepatitis B Virus Surface Antigen (HBsAg) Particles into the Medium by its Secretory Apparatus," *Appl. Microbiol. Biotechnol.* 40:33–340 (1993).

Lablanche, J.M., et al., "Percutaneous Aspriation of a Coronary Thrombus," *Catheterization and Cardiovascular Diagnosis* 17:97–98 (1989).

Larsson, M., et al., "Role of Anexins in Endocytosis of Antigens in Immature Human Dendritic Cells," *Immunology* 92:501–511 (1997).

Latta, M. et al., "Synthesis and Purification of Mature Human Serum Albumin From *E. Col,*" *Bio/Technology* 5:1309–1314 (1987).

Latta, M., et al., "Tryptophan Promoter Derivatives on Multicopy Plasmids: A Comparative Analysis of Expression Potentials in *Escherichia coli,*" *DNA and Cell Biology* 9:129–137 (1990).

Lawn, R.M., et al., "The Sequence of Human Serum Albumin cDNA and its Expression in *E. coli,*" *Nucleic Acids Research* 9:6103–6113 (1981).

Le Bras, M., et al., "Epidemiologie et Clinique des Maladies Tropicales D'importation," *La Revue de Medicine Interne* 13:205–210 (1992), with English translation.

Leblois, H., et al., "Stable Transduction of Actively Dividing Cells via a Novel Adenoviral/Episomal Vector," *Molecular Therapy* 1:314–322 (2000).

Lee, C–H., et al., "Sodium Pertechnetate Tc99m Antral Scan in the Diagnosis of Retained Gastric Antrum," *Arch. Surg.* 119:309–311 (1984).

Lee, C–L., et al., "Preparation and Characterization of Polyethylene–Glycol–Modified Salmon Calcitonins," *Pharmaceutical Development and Technology*, 4(2):269–275 (1999).

Lee, W–C., et al., "Identification and Characterization of a Nuclear Localization Sequence–Binding Protein in Yeast," *Proc. Natl. Acad. Sci. USA* 86:8808–8812 (1989).

Lee, Y–H., et al., "Comparison of Effective Renal Plasma Flow (ERPF) and Endogenous Creatinine Clearance (Ccr) in Evaluation of the Differential Kidney Function: An in Vivo Study," *Chin. Med. J. (Taipei)* 49:147–152 (1992).

Lei, H–Y., et al., "An Antigen–specific Hypersensitivity Which Does Not Fit Into Traditional Classification of Hypersensitivity," *The Journal of Immunology* 143:432–438 (1989).

Levitt, D., et al., "Toxicity in Perfluorinated Fatty–Acids for Human and Murine B Cell Lines," *Toxicology and Applied Pharmacology* 86:1–11 (1986).

Lew D.B., et al., "Mitogenic Effect of Lysosomal Hydrolases on Bovine Tracheal Myocytes in Culture," *The Journal of Clinical Investigation* 88:1969–1975 (1991).

Lewis, C., et al., "Is Sexual Dysfunction in Hypertensive Women Uncommon or Understudies?" *American Jour of Hypertension*, 11:733–735 (1998).

Li, C.H., "Human Growth Hormone: 1974–1981," *Molecular and Cellular Biochemistry* 46:31–41 (1982).

Li, H., et al., "Adenovirus–Mediated Delivery of a uPA/uPAR Antagonist Suppresses Angiogenesis–Dependent Tumor Growth and Dissemination in Mice," *Gene Therapy* 5:1105–1113 (1998).

Li, H., et al., "Systemic Delivery of Antiangiogenic Adenovirus AdmATF Induces Liver Resistance to Metastasis and Prolongs Survival of Mice," *Human Gene Therapy* 10:3045–3053 (1999).

Li, Y., et al., "Sheep Monoclonal Antibody Fragments Generated Using a Phage Display System," *Jour. of Immunological Methods* 236:133–146 (2000).

Li, Y–Y., et al., "Functional Mutation in the Promoter Region of Thrombomodulin Gene in Relation to Carotid Atherosclerosis," *Atherosclerosis* 154:713–719 (2001).

Lie, O., et al., "Possible Association of Antibody Responses to Human Serum Albumin and (T,G)–A—L with the Bovine Major Histocompatibility Complex (BoLA)," *Veterinary Immunology and Immunopathology* 11:330–350 (1986).

Liljeqvist S., et al., "Fusions to the Cholera Toxin B Subunit: Influence on Pentamerization and GM1 Binding," *Jour. of Immunological Methods* 210:125–135 (1997).

Lin, L., "Betaseron," in *Characterization of Biotechnology Pharmaceutical Products. Dev Biol. Stand.* vol. 96, eds. F. Brown et al.: 97–104 (1998).

Lionetti, F.J., et al., "Temperature Effects on Shape and Function of Human Granulocytes," *Exp. Hemat.* 8:304–317 (1980).

Lo, K–J., et al., "Combined Passive and Active Immunization for Interruption of Perinatal Transmission of Hepatitis B Virus in Taiwan," *Hepato–gastroenterol.* 32:65–68 (1985).

Lu, H., et al., "Blockage of the Urokinase Receptor on the Cell Surface: Construction and Characterization of a Hybrid Protein Consisting of the N–Terminal Fragment of Human Urokinase and Human Albumin," *FEBS Letters* 356:56–59 (1994).

Lu, H., et al., "Blockage of Urokinase Receptor Reduces In Vitro the Mobility and the Deformability of Endothelial Cells," *FEBS Letters* 380:21–24 (1996).

Mack, S., et al., "Acrosomal Enzymes of Human Spermatozoa Before and After in Vitro Capacitation," *Biology of Reproduction* 28:1032–1042 (1983).

Macovski, A., et al., "Isolated Iodine Images Using Spatial-frequency Encoding," *Med. Phys.* 6:53–58 (1979).

Madison, J., et al., "Genetic Variants of Human Serum Albumin in Italy: Point Mutants and a Carboxyl–Terminal Variant," *Proc. Natl. Acad. Sci. USA* 91:6476–6480 (1994).

Maignan, S., et al., "Crystal Structure of the Mammalian Grb2 Adaptor," *Science* 268:291–293 (1995).

Makrides, S.C., et al., "Extended in Vivo Half–Life of Human Soluble Complement Receptor Type 1 Fused to a Serum Albumin–Binding Receptor," *J. of Pharm. and Exp. Therapeutics* 277:534–542 (1996).

Martial, J.A. et al., "Human Growth Hormone: Complementary DNA Cloning and Expression in Bacteria," *Science* 205:602–607 (1979).

Martin, C., et al., "Pseudomonas Aeruginosa Diaminopimelate Decarboxylase: Evolutionary Relationship with Other Amino Acid Decarbosylases," *Mol. Biol. Evol.* 5:549–559 (1988).

Masih, D.T., et al., "Immunosuppression in Experimental Cryptococcosis in Rats," *Mycopathologia* 114:179–186 (1991).

Matsuda, Y., et al., "Human Serum Albumin Variants," *Tanpakushitu Kakusan Koso* 33(5):930–935 (1988), with English translation.

Mattiasson, B., et al., "Binding Assays in Heterogeneous Media Using a Flow Injection System with an Expanded Micro–bed Adsorption Column," *Bioseparation* 8:237–245 (1999).

Mayaux, J–F., et al., "Purification, Cloning, and Primary Structure of a New Enantiomer–Selective Amidase from a Rhodococcus Strain: Structural Evidence for a Conserved Genetic Coupling with Nitrile Hydratase," *Jour. of Bacteriology* 173:6694–6704 (1991).

Mazure, N.M., et al., "Oncogenic Transformation and Hypoxia Synergistically Act to Modulate Vascular Endothelial Growth Factor Expression," *Cancer Research* 56:3436–3440 (1996).

Meisel, H., et al., "Fine Mapping and Functional characterization of Two Immuno–Dominant Regions from the preS2 Sequence of Hepatitis B Virus," *Intervirology* 37:330–339 (1994).

Melnick, L.M., et al., "Characterization of a Nonglycosylated Single Chain Urinary Plasminogen Activator Secreted from Yeast," *The Journal of Biological Chemistry* 265:801–807 (1990).

Michel, M–L., et al., "Synthesis in Animal Cells of Hepatitis B Surface Antigen Particles Carrying a Receptor for Polymerized Human Serum Albumin," *Proc. Natl. Acad. Sci. USA* 81:7708–7712 (1984).

Mimran, A., et al., "GCN4–Based Expression System (pGES): Tranlationally Regulated Yeast Expression Vectors," *Bio Techniques* 28:552–560 (2000).

Minchiotti, L., et al., "Structural Characterization, Stability and Fatty Acid–Binding Properties of Two French Genetic Variants of Human Serum Albumin," *Biochimica et Biophysical Acta* 1431:223–231 (1999).

Minchiotti, L., et al., "The Molecular Defect of Albumin Castel di Sangro: 536 Lys→Glu," *Biochimica et Biophysica Acta* 1039:204–208 (1990).

Minchiotti, L., et al., "The Structural Characterization and Bilirubin–Binding Properties of Albumin Herborn, a[Lys240→Glu] Albumin Mutant," *Eur. J. Biochem.* 214:437–444 (1993).

Minchiotti, L., et al., "Two Alloalbumins with Identical Electrophoretic Mobility are Produced by Differently Charged Amino Acid Substitutions," *Biochimica et Biophysica Acta* 1119:232–238 (1992).

Mohammad, J., et al., "Dye–Ligand Affinity Chromatograhy on Continuous Beds," *Biomedical Chromatography* 9:80–84 (1995).

Moore, K.L., et al., "Effect of Active Immunization Growth Hormone Releasing Factor on Concentrations of Somatotropin and Insulin–Like Growth Factor I in Lactating Beef Cows," *Domestic Animal Endocrinology* 9:125–139 (1992).

Mora, I., et al., "Changes of Hepatitis B Virus (HBV) Markers During Prolonged Recombinant Interferon Alpha–2A Treatment of Chronic HBV Infection," *Journal of Hepatology* 4:29–36 (1987).

Morlino, G.B., et al., "Inducible Amplication of Gene Copy Number and Heterologous Protein Production in the Yeast *Kluyveromyces lactis,*" *Applied and Environmental Microbiology* 65:4808–4813 (1999).

Mroczka, D.L., et al., "Characterization of Rat Ribosomal DNA," *J. Mol. Biol.* 174:141–162 (1984).

Mullick, A., et al., "Expanded Bed Adsorption of Human Serum Albumin from Very Dense *Saccharomyces cerevisiae* Suspensions on Fluoride–Modified Zirconia," *Biotechnology and Bioengineering* 65:282–290 (1999).

Murray, J.C., et al., "Molecular Genetics of Human Serum Albumin: Restriction Enzyme Fragment Length Polymorphisms and Analbuminemia," *Proc. Natl. Acad. Sci. USA* 80:5951–5955 (1983).

Nabiev, R.F., et al., "Dynamics of the Spontaneous Emission of an Atom into the Photon–destiny–of–states gap: Solvable Quantum–electrodynamical Model," *Physical Review A* 47:3380–3384 (1993).

Newbold, P., et al., "The Modulation of Inflammatory Oedema by Calcitonin Gene–Related Peptide," *Br. J. Pharmacol.* 108:705–710 (1993).

Nieken, J., et al., "Recombinant Human Interleukin–6 Induces a Rapid and Reversible Anemia in Cancer Patients," *Blood* 86:900–905 (1995).

Nilsson, J., et al., "Competitive Elution of Protein A Fusion Proteins Allows Specific Recovery Under Mild Conditions," *Eur. J. Biochem* 224:103–108 (1994).

Nilsson, J., et al., "Heat–Mediated Activation of Affinity-Immobilized Taq DNA Polymerase," *BioTechniques* 22:744–751 (1997).

Nishio, H., et al., "Tandem Arrangement of the Human Serum Albumin Multigene Family in the Sub–centromeric Region of 4q: Evolution and Chromosomal Direction of Transcription," *J. Mol. Biol.* 259:113–119 (1996).

Nomura, N., et al., "Secretion by *Saccharomyces cerevisiae* of Human Apolipoprotein E as a Fusion to Serum Albumin," *Biosci. Biotech. Biochem.*, 59:532–534 (1995).

Nord, K., et al., "A Combinatorial Library of an α–helical Bacterial Receptor Domain," *Protein Engineering* 8:601–608 (1995).

Nygren, P–A., et al., "Analysis and Use of the Serum Albumin Binding Domains of Streptococcal Protein G," *Jour. of Molecular Recognition* 1:69–74 (1988).

Nygren, P-A., et al., "Species–Dependent Binding of Serum Albumins to the Streptococcal Receptor Protein G," *FEBS* 193:143–148 (1990).

Obayashi, H., et al., "Inhibition of Posthemorrhagic Transfusion–Induced Gastric Injury by a Long–Acting Superoxidee Dismutase Derivative," *Proc. Soc. Exp. Biol. and Med.* 196:164–169 (1991).

Ogino, T., et al., "Chemical Modification of Superoxide Dismutase–Extension of Plasma Half Life of the Enzyme Through its Reversible Binding to the Circulating Albumin," *Int. J. Peptide Protein–Res.* 32:153–159 (1988).

Ogino, T., et al., "Chemical Modification of Superoxide Dismutase. Extension of Plasma Half Life of the Enzyme Through its Reversible Binding to the Circulating Albumin," Abstract. *Chem. Abstracts* 109, No. 163477u (1988).

Ogorek, B., et al., "Comparative Study on the Effects of Cyclophosphamide on Yeast In Vitro and in the Host–Mediated Assay: DNA Damage and Biological Response," *Chem.–Biol. Interactions* 37:141–154 (1981).

Ohi, H., et al., "Chromosomal DNA Patterns and Gene Stability of *Pichia pastoris*," *Yeast* 14:895–903 (1998).

Ohi, H., et al., "The Positive and Negative cis–Acting Elements for Methanol Regulation in the *Pichia Pastoris* AOX2Gene," *Mol. Gen. Genet.* 243:489–499 (1994).

Ohnuma, H., et al., "Large Hepatitis B Surface Antigen Polypeptides of Dane Particles With the Receptor for Polymerized Human Serum Albumin," *Gastroenterology* 90:695–701 (1986).

Ohtani, W., et al., "Analysis of *Pichia pastoris* Components in Recombinant Human Serum Albumin by Immunological Assays and by HPLC with Pulsed Amperometric Detection," *Anal. Chem.* 70:425–429 (1998).

Ohtani, W., et al., "Physiochemical and Immunological Properties of Recombinant Human Serum Albumin from *Pichia pastoris*," *Human Biochemistry* 256:56–62 (1998).

Ohtani, W., et al., "Structure of Tecombinant Human Serum Albumin from *Pichia pastoris*," *J. Pharm. Soc. Japan* 117(4):220–232 (1997), with English translation.

Okabayashi, K., et al., "Secretory of the Human Serum Albumin Gene in the Yeast, *Saccharomyces cerevisiae*," *J. Biochem.* 110:103–110 (1991).

Paige, A., et al., "Prolonged Circulation of Recombinant Human Granulocyte–Colony Stimulating Factor by Covalent Linkage to Albumin Through a Heterobifunctional Polyethylene Glycol," *Pharmaceutical Research* 12:1883–1888 (1995).

Palframan, R.T., et al., "The Effect of a Tachykinin, $NK_1$ Receptor Antagonist, SR140333, on Oedema Formation induced in rat skin by venom from the *Phoneutria nigriventer* Spider," *British Jour. of Pharmacology* 118:295–298 (1996).

Pannain, S., "Familial Dysalbuminemic Hyperthyroxinemia in a Swiss Family Caused by a Mutant Albumin (R218P) Shows an Apparent Discrepancy between Serum Concentration and Affinity for Thyroxine," *The Journal of Clinical Endocrinology & Metabolism* 85:2786–2792 (2000).

Parhami–Seren, D.S., et al., "Expression of a Human Serum Albumin Fragment (Consisting of Subdomains IA, IB, and IIA) and a Study of Its Properties," *IUBMB Life* 48:169–174 (1999).

Pasquinelli, A. E., et al., "Inhibition of mRNA Export in Vertebrate Cells by Nuclear Export Signal Conjugates," *Proc. Natl. Acad. Sci. USA* 94:14394–14399 (1997).

Pereira F.B., et al., "Membrane Fusion Induced by the HIV Type 1 Fusion Peptide: Modulation by Factors Affecting Glycoprotein 41 Activity and Potential Anti–HIV Compounds," *AIDS Research and Human Retroviruses* 13:1203–1211 (1997).

Pessina, G.P., et al., "Enhanced Induction of Plasma Interferon After Subcutaneous Administration in Rabbits of Poly ICLC with Albumin," *Journal of Biological Regulators and Homeostatic Agents* 3:118–121 (1989).

Petersen, C.E., et al., "A Dynamic Model for Bilirubin Binding to Human Serum Albumin," *The Journal of Biological Chemistry* 275:20985–20995 (2000).

Petersen, C.E., et al., "A Point Mutation in the Human Serum Albumin Gene Results in Familial Dysalbuminaemic Hyperthyroxinaemia," *J. Med. Genet.* 31:355–359 (1994).

Petersen, C.E., et al., "Expression of a Human Serum Albumin Variant with High Affinity for Thyroxine," *Biochemical and Biophysical Research Communications* 214:1121–1129 (1995).

Petersen, C.E., et al., "Mutagenesis Studies of Thyroxine Binding to Human Serum Albumin Define an Important Structural Characteristic of Subdomain 2A," *Biochemistry* 36:7012–7017 (1997).

Petersen, C.E., et al., "Mutations in a Specific Human Serum Albumin Thyroxine Binding Site Define the Structural Basis of Familial Dysalbuminemic Hyperthyroxinemia," *The Journal of Biological Chemistry* 271:19110–19117 (1996).

Petersen, C.E., et al., "Structural Investigations of a New Familial Dysalbuminemic Hyperthyroxinemia Genotype," *Clinical Chemistry* 45:1248–1254 (1999).

Pevzner, I.Y., et al., "B–Complex Genetic Control of Immune Response to HSA, (T,G)–A—L, GT and Other Substances in Chickens," *Jour. of Immunogenetics* 6:453–460 (1979).

Phipps, R.P., et al., "Efficient Generation of Functional Transgenes by Homologous Recombinant in Murine Zygotes," *Nucleic Acids Research* 20:1259–1264 (1992).

Piggott, J.R., et al., "The Secretion and Post Translational Modification of Interferons from *Saccharomyces Cerevisiae*," *Curr. Genet* 12:561–567 (1987).

Pinkert, C.A., et al., "An Albumin Enhancer Located 10 kb Upstream Functions Along with its Promoter to Direct Efficient, Liver–Specific Expression in Transgenic Mice," *Genes and Development* 1:268–278 (1987).

Poch, O., et al., "Sequence of the *Kluyveromyces lactis* β–galactosidase: comparison with Prokaryotic Enzymes Secondary Structure Analysis," *Gene* 118:5–63 (1992).

Pollock, D.P., et al., "Transgenic Milk as a Method for the Production of Recombinant antibodies," *Jour. of Immunological Methods* 231:147–157 (1999).

Pontisso, P., et al., "Antibody to the Hepatitis B Virus Receptor for Polymerized Albumin in Acute Infection and in Hepatitis B Vaccine Recipients," *Journal of Hepatology* 3:393–398 (1986).

Poznansky, T., et al., "Growth Hormone–Albumin Conjugates Reduced Renal Toxicity and Altered Plasma Clearance," *FEBS Letters* 239:18–22 (1988).

Price, T., et al., "One Hundred Years of Natural Selection in the Wild," *Endeavour* 23:145–147 (1999).

Quirk, A.V., et al., "Production of Recombinant Human Serum Albumin from *Saccharomyces cerevisiae*," *Biotechnology and Applied Biochemistry* 11:273–287 (1989).

Ragni, M.V., "New–Generation Recombinant Factor Concentrates: Bridge to Gene Therapy," *Haemophilia*, 7:28–35 (2001).

Randem, I., et al., "Human Monoclonal Rheumatoid Factors Derived from the Polyclonal Repertoire of Rheumatoid Synovial Tissue: Production and Characterization," *Clin. Exp. Immunol.* 78:13–18 (1989).

Reed, R.G., et al., "Non–Resolving Jaundice: Bilirubin Covalently Attached to Serum Albumin Circulates with the Same Metabolic Half–Line as Albumin," Abstract, *Chem. Abstract* 109, No. 227803g (1988).

Reichardt, W., et al., "Mapping of Binding Sites for Human Serum Albumin and Fibrinogen on the M3–Protein," in *Streptocci and the Host*, ed. Horaud et al., Plenum Press, 577–579 (1997).

Reininger, L., et al., "On the Molecular Basis of T–Helper-Cell Function," *Cellular Immunology* 92:85–104 (1985).

Ridger, V., et al., Effect of the Inducible Nitric Oxide Synthase Inhibitors Aminoguanidine and L–$N^6$–(1–Iminoethyl) lysine on Zymosan–Induced Plasma Extravasation in Rat Skin, *The Journal of Immunology* 159:383–390 (1997).

Rogovin, D., et al., "Harmonic Phase Conjugatin in Liquid Suspensions of Microparticles via Higher–Order Gratings," *Physical Review Letters* 55:2864–2867 (1985).

Romano, A., et al., "Use of Human Fibroblast–Derived (Beta) Interferon in the Treatment of Epidemic Adenovirus Keratoconjunctivitis," *Journal of Interferon Research* 1:95–100 (1980).

Rostenberg, I., "The Origin of Serum Protein, A, B and H Blood Group, and Gm an Inv Antigens in House Dust," *Acta Allergologica* 31:265–274 (1976).

Rubinstein, H.R., et al., "Immunosuppression in Experimental Cryptococcosis in Rats: Modification of Macrophage Functions by T Suppressor Cells," *Mycopathologia* 108:11–19 (1989).

Ruhland, A., et al., "Genetic Activity of Chemicals in Yeast: DNA Alterations and Mutations Induced by Alkylating Anti–Cancer Agents," *Mutation Research* 58:241–250 (1978).

Rushbrook, J.I., et al., "Identification of a Human Serum Albumin Species Associated with Familial Dysalbuminemic Hyperthyroxinemia*," *Jour. of Clinical Endocrinology and Metabolism* 80:461–467 (1995).

Ruzgas, T.A., et al., "Ellipsometric Immunosensors for th Determination of γ–Interferon and Human Serum Albumin," *Biosensors & Bioelectronics* 7:305–308 (1992).

Ruzgas, T.A., et al., "Ellipsometric Study of Antigen–Antibody Interaction at the Interface Solid/Solution," *Biofizika*, 37 (1):56–61 (1992), with English translation.

Ryff, J–C., "Clinical Investigation of the Immunogenicity of Interferon–αa," *Journal of Interferon and Cytokine Research* 17:S29–S33 (1997).

Sakuragawa, N., et al., "Human Amniotic Epithelial Cells are Promising Transgene Carriers for Allogeneic Cell Transplantation into Liver," *J. Human Genet* 45:171–176 (2000).

Saliola, M., et al., "Use of the KIADH4 Promoter for Ethanol–Dependent Production of Recombinant Human Serum Albumin in *Kluyveromyces lactis*," *Applied and Environmental Microbiology* 65:53–60 (1999).

Satoh, K., et al., "Hemodynamic Changes by Recombinant Erythropoietin Therapy in Hemodialyzed Patients," *Hypertension* 15:262–266 (1990).

Saunders, C.W., et al., "Secretion of Human Serum Albumin from *Bacillus subtilis*," *Jour. of Bacteriology* 169:2917–2925 (1987).

Savolainen, J., et al., "Stability of *Candida albicans* Allergens During Storage," *Clinical and Experimental Allergy* 22:991–995 (1992).

Sawaguchi, S., et al., "Effects of Intracameral Injection of Chondroitinase ABC In Vivo," *Arch. Opthalmol*, 110:110–117 (1992).

Scanes, C., et al., "Growth Hormone: Chemistry," Chapter 1 in *Growth Hormone*, eds. S. Harvey et al., 1–24 (1995).

Schafer–Korting, M., et al., "Influence of Albumin on Itraconazole and Ketoconazole Antifungal Activity: Results of a Dynamic In Vitro Study," *Antimicrobial Agents and Chemotherapy* 35:2053–2056 (1991).

Schenkman, S., et al., "Effects of Temperature and Lipid Composition on the Serum Albumin–Induced Aggregation and Fusion of Small Unilamellar Vesicles," *Biochimica et Biophysica Acta* 649:633–641 (1981).

Schmidt, K–H., et al., "Protein A–Streptokinase Fusion Protein for Immunodetection of Specific IgG Antibodies," *Jour. of Immunological Methods* 143:111–117 (1991).

Schoen, P., et al., "Inhibition of Influenza Virus Fusion by Polyanionic Proteins," *Biochemical Pharmacology* 53:995–1003 (1997).

Schoppee, P.D., et al., "Endocrine and Ovarian Responses to Exogenous Estradiol–17β in 6–Month–Old Heifers Previously Immunized Against Growth Hormone–Releasing Factor," *J. Anim. Sci.* 73:2071–2078 (1995).

Schuster, M., et al., "Short Cut of Protein Purification by Integration of cell–disrupture and Affinity Extraction," *Bioseparation* 9:59–67 (2000).

Semba, K., et al., "A v–erbB–related Protooncogene, c–erbB–2, is Distinct From the c–erbB–1/Epidermal Growth Factor–Receptor Gene and is Amplified in a Human Salivary Gland Adenocarcinoma," *Proc. Natl. Acad. Sci. USA* 82:6497–6501 (1985).

Shamoon, B., et al., "Woodchuck Hepatitis Virus Surface Antigen Produced in vitro Fails to Bind Polymerized Woodchuck Serum Albumin," *Journal of General Virology* 75:2081–2084 (1994).

Shani, M., et al., "Expression of Human Serum Albumin in the Milk of Transgenic Mice," *Transgenic Research* 1:195–208 (1992).

Shepherd, N.S., et al., "Preparation and Screening of an Arrayed Human Genomic Library Generated with the P1 Cloning System," *Proc. Natl. Acad. Sci. USA* 91:2629–2633 (1994).

Shin S–U., et al., "Functional and Pharmacokinetic Properties of Antibody–Avidin Fusion Proteins," *The Jour. of Immunology* 158:4797–4804 (1997).

Shinya, E., et al., "In–Vivo Delivery of Therapeutic Proteins by Genetically–Modified Cells: Comparison of Organoids and Human Serum Albumin Alginate–Coated Beads," *Biomed & Pharmacother* 53:471–83 (1999).

Sijmons, P.C., et al., "Production of Correctly Processed Human Serum Albumin in Transgenic Plants," *Biotechnology* 8:217–221 (1990).

Simmons, D. et al., "The Fcγ Receptor of Natural Killer Cells is a Phospholipid–Linked Membrane Protein," *Nature* 333:568–570 (1988).

Simoes, S., et al., "Human Serum Albumin Enhances DNA Transfections by Lipoplexes and Confers Resistance to Inhibition by Serum," *Biochimica et Biophysica Acta* 1463:459–469 (2000).

Simpson, R.B., et al., "Effect of Active Immunization Against Growth Hormone–Releasing Factor on Growth and Onset of Puberty in Beef Heifers," *J. Anim. Sci.* 69:4914–4924 (1991).

Sjobring, U., "Isolation and Molecular Characterization of a Novel Albumin–Binding Protein from Group G Streptococci," *Infection and Immunity* 60:3601–3608 (1992).

Sjobring, U., et al., "Protein G Genes: Structure and Distribution of IgG–binding and Albumin–binding Domains," *Molecular Microbiology* 3:319–327 (1989).

Sjobring, U., et al., "Streptococcal Protein G," *The Journal of Biological Chemistry* 266:399–405 (1991).

Sjolander, A., et al., "Immunogenicity and Antigenicity in Rabbits of a Repeated Sequence of *Plasmodium Falciparum* Antigen Pf155/RESA Fused to Two Immunoglobulin G–Binding Domains of Staphylococcal Protein A," *Infection and Immunity* 58:854–859 (1990).

Skerra A., "Engineered Protein Scaffolds for Molecular Recognition," *Jour. of Mol. Recognit.* 13: 167–187 (2000).

Sleep, D., et al., "Cloning and Characterization of the *Saccharomyces cerevisiae* Glycerol–3–Phosphate Dehydrogenase (GUT2) Promoter," *Gene*, 101:89–96 (1991).

Sleep, D., et al., "*Saccharomyces Cerevisiae* Strains That Overexpresses Heterologous Proteins," *Bio/Technology* 9:183–187 (1991).

Sleep, D., et al., "The Secretion of Human Serum Albumin From the Yeast *Saccharomyces Cerevisiae* Using Five Different Leader Sequences," *Bio/Technology* 8:42–46 (1990).

Smedsrud, T., et al., "Endocytosis of a Mannose–Terminated Glycoprotein and Formaladehyde–Treated Human Serum Albumin in Liver and Kidney Cells from Fish (*Salmon Alpinus* L.)," *Developmental and Comparative Immunology* 8:579–588 (1984).

Somersalo, K., et al., "Stimulated Natural Killer Cells Secrete Factors with Chemotactic Activity, Including NAP–1/IL–8, which Supports VLA–4–and VLA–5–mediated Migration of T Lymphocytes," *Eur. J. Immunol.* 24:2957–2965 (1994).

Sotomayer, C.E., et al., "Immunsuppression in Experimental Cryptococcosis: Variation of Splenic and Thymic Populations and Expression of Class II Major Histocompatibility Complex Gene Products," *Clinical Immunology and Immunopathology* 77:19–16 (1995).

Sotomayer, C.E., et al., "Immunosuppression in Experimental Cryptococcosis in Rats. Induction of Afferent T Suppressor Cells to a non–related Antigen," *Journal of Medical and Veterinary Mycology* 25:67–75 (1987).

Srinivasan, S.K., et al., "Characterization of Binding Sites, Extent of Binding, and Drug Interactions of Oligonucleotides with Albumin," *Antisense Research and Development* 5:131–139 (1995).

Stahl, S., et al., "A Dual Expression System for the Generation, Analysis and Purification of Antibodies to a Repeated Sequence of the *Plasmodium Falciparum* Antigen PF155/RESA," *Jour. of Immunological Methods* 124:43–52 (1989).

Stanko, R.L., et al., "Effect of Somatotropin and/or Equine Chorionic Gonadotropin on Serum and Follicular Insulin––Like Growth Factor I and Insulin–Like Growth Factor Binding Proteins in Cattle," *Biology of Reproduction* 50:290–300 (1994).

Steinman, C., et al., "Fibrinogen Milano V: A Congenital Dysfibrinogenaemia with a gamma 275 ARG→Cys Substitution," *Blood Coagulation and Fibrinolysis* 5:463–471 (1994).

Steven, J., et al., "Purification and Characterization of Plasminogen Activator Inhibitor 2 Produced in *Saccharomyces cerevisiae*," *Eur. J. Biochem.*, 196:431–438 (1991).

Stinson, R.A. et al., "Comparative Studies of Pure Alkaline Phosphatases from Five Human Tissues," *Clinica Chimica Acta* 110:261–272 (1981).

Strobl, J.S., et al., "Human Growth Hormone," *Pharmacological Reviews* 46:1–34 (1994).

Subbery, P.E., et al., "Genes Which Control Cell Proliferation in Yeast *Saccharomyces cerevisiae*," *Nature* 288:401–404 (1980).

Sugio, S., et al., "Crystal Structure of Human Serum Albumin at 2.5 Å Resolution," *Protein Engineering* 12:439–446 (1999).

Swanchara, K.W., et al., "Effects of Active Immunization Against Growth–Hormone Releasing Factor on Puberty and Reproductive Development in Gilts," *J. Anim. Sci.* 77:1807–1814 (1999).

Swinkels, B.W., et al., "The Yeast *Kluyveromyces Lactis* as an Efficient Host for Heterologous Gene Expression," *Antonie van Leeuwenhoek* 64:187–201 (1993).

Takahashi, K., et al., "Polypeptides Coded for by the Region Pre–S and Gene S of Hepatitis B Virus DNA with the Receptor for Polymerized Human Serum Albumin: Expression of Hepatitis B Particles Produced in the HBeAg or Anti–HBe Phase of Hepatitis B Virus Infection." *The Journal of Immunology* 136:3467–3472 (1986).

Takahashi, K–I, et al., "Production of Bioactive Salmon Calcitonin From the Nonendocrine Cell Lines COS–7 and CHO," *Peptides* 18(3):439–444 (1997).

Takahashi, N., et al., "Amino Acid Substitutions in Genetic Variants of Human Serum Albumin and in Sequences Inferred from Molecular Cloning," *Proc. Natl. Acad. Sci. USA* 84:4413–4417 (1987).

Takami, M., et al., "Maleylated Human Serum Albumin Inhibits HIV–1 Infection in vitro," *Biochimica et Biophysica Acta* 1180:180–186 (1992).

Takeshima, K., et al., "Ligand Binding Properties and Esterase–like Activity of Recombinant Human Serum Albumin," *Regular Articles Yakugaku Zasshi* 116(8);622–629 (1996), with English translation.

Tang, K–T., et al., "Skin Microvascular Reflexes in Patients with Diabetic Autonomic Neuropathy," *Chin. Med. J. (Taipei)* 41:57–62 (1988).

Tarelli, E., et al., "Recombinant Human Albumin as a Stabilizer for Biological Materials and for the Preparation of International Reference Reagents," *Biologicals* 26:331–346 (1998).

Tawara, S., et al., "In Vitro Activities of a New Lipopeptide Antifungal Agent, FK463, Against a Variety of Clinically Important Fungi," *Antimicrobial Agents and Chemotherapy* 44:57–62 (2000).

Thery, C., et al., "Filter Cave Temporaire Permettant le Diagnostic et al Fibrinolyse Chez les Patients Suspects d'embolie Pulmonaire Massive," *Arch. Mal. Coeur* 84:525–530 (1991), with English translation.

Thery, C., et al., "Use of a Mew Removable Vene Cava Filter in Order to Prevent Pulmonary Embolism in Patients Submitted to Thrombolysis," *Eur. Heart Journal* 11:334–341 (1990).

Tribelli, C., et al., "New Concepts in Bilirubin and Jaundice: Report of the Third International Bilirubin Workshop, Apr. 6–8, 1995, Trieste, Italy," *Hepatology* 24:1296–1311 (1996).

Tokunaga, T., et al., "Expression of a Synthetic Human Growth Hormone Gene in Yeast," *Gene* 39:117–120 (1985).

Torrent, C., et al., "Transgene Amplification and Persistence after Delivery of Retroviral Vector and Packaging Functions with E1/E4–Deleted Adenoviruses," *Cancer Gene Therapy* 7:1135–1144 (2000).

Traunecker, A., et al., "Soluble CD4 Molecules Neutralize Human Immunodeficiency Virus Type 1," *Nature* 331:84–86 (1988).

Trout, W.E., et al., "Growth Hormone and Insulin–Like Growth Factor–I Responses in Steers Actively Immunized Against Somatostatin or Growth Hormone–Releasing Factor," *Journal of Endocrinology* 125:123–129 (1990).

Tsiomenko, A.B., et al., "Prosegment of Yeast α–Factor Directs a Heterologous Protein (Human Growth Hormone) to the Culture Medium of *Saccharomyces cerevisiae*," *Biochemistry* 59:1247–1256 (1994).

Tzanela, M., et al., "Recombinant Human Growth Hormone–Binding Protein Fails to Enhance the in Vivo Bioactivity of Human Growth Hormone in Normal Rats," *Endocrinology*, 108(12):5316–5324 (1997).

Uhlen, M., et al., "Gene Fusions for Purpose of Expression: An Introduction," *Gene Expression Technology* 185:129–143 (1990).

Vigne, E., et al., "RGD Inclusion in the Hexon Monomer Provides Adenovirus Type 5–Based Vectors with a Fiber Knob–Independent Pathway for Infection," *Jour. of Virology* 73:5156–5161 (1999).

Vincent, M.P., et al., "Surdosage a l'halofantrine," *La Presse Medicale* 3:131 (1992), with English translation.

Vorum, H., et al., "Expression of Recombinant Psoriasis–associated Fatty Acid Binding Protein in *Escherichia coli*: Gel Electrophoretic Characterization, Analysis of Binding Properties and Comparison with Human Serum Albumin," 19:1793–1802 (1998).

Wang, Y., et al., "Expression and Secretion of preS Containing Hepatitis B Surface Antigen in Vaccinia Virus System," *Science in China* 33:1070–1077 (1990).

Watanabe, H., et al., "Role of Arg–410 and Tyr–411 in Human Serum Albumin for Ligand Binding and Esteraselike Activity," *Biochem. J.* 349:813–819 (2000).

Waters, J., et al., "Virus–neutralizing Antibodies to Hepatitis B Virus: The Nature of an Immunogenic Epitope on the S Gene Peptide," *J. Gen. Virol.* 67:2467–2473 (1986).

Weitkamp, L.R., et al., "Albumin Maku: A New Variant of Human Serum Albumin," *Nature* 217:759–760 (1968).

Weitkamp, L.R., et al., "Human Serum Albumin: Twenty–Three Genetic Variants and Their Population Distribution," *Ann. Hum. Genet. Lond.* 36:381–392 (1973).

Welinder, B.S. et al., "Recovery of Polypeptides After Reversed–Phase High–Performance Liquid Chromatography," *Journal of Chromatography* 408:191–199 (1987).

Welinder, B.S., "Use of Polymeric Reversed–Phase Columns for the Characterization of Polypeptides Extracted from Human Pancreata," *Journal of Chromatography* 542:83–99 (1991).

Whittington, H., et al., "Expression of the *Asperigillus niger* glucose Oxidase gene in *A. niger, A. nidulans* and *Saccharomyces cerevisiae*," *Current Genetics* 8:531–536 (1990).

Williams, D.E., et al., "Enhanced Biological Activity of a Human GM–CSF/IL–3 Fusion Protein," *Experimental Hematology* 18:615 (1990).

Williams, D.E., et al., "Hybrid Cytokines as Hematopoietic Growth Factors," *International Journal of Cell Cloning* 9:542–547 (1991).

Wilson, G., et al., "Selective Hepatic Uptake of Synthetic Glycoproteins," *The Journal of General Physiology* 74:495–509 (1979).

Wooley, P.H., et al., "Influence of a Recombinant Human Soluble Tumor Necrosis Factor Receptor FC Fusion Protein on Type II Collagen–Induced Arthritis in Mice," *The Jour. of Immunology* 151:6602–6607 (1993).

Wu, G.Y., et al., "Receptor–Mediated Gene Delivery in vivo," *The Journal of Biological Chemistry* 266:14338–14342 (1991).

Wu, J–C., et al., "Isoniazid–Rifampin–Induced Hepatitis in Hepatitis B Carriers," *Gastroenterology* 98:502–504 (1990).

Xu, X., et al., "Regulation of the Release of Eosinophil Cationic Protein by Eosinophil Adhesion," *Clinical and Experimental Allergy* 30:794–806 (2000).

Yeh, P., et al., "A Shuttle Vector System for *Brevibacterium Lactofermentum*," *Gene* 47:301–306 (1986).

Yeh, P., et al., "Advances in Adenoviral Vectors: From Genetic Engineering to Their Biology," *The FASEB Journal* 11:615–623 (1997).

Yeh, P., et al., "Design of Yeast–Secreted Albumin Derivatives for Human Therapy: Biological and Antiviral Properties of a Serum Albumin–CD4 Genetic Conjugate," *Proc. Natl. Acad. Sci. USA* 89:1904–1908 (1992).

Yeh, P., et al., "Efficient Dual Transcomplementation of Adenovirus E1 and E4 Regions from a 293–Derived Cell Line Expressing a Minimal E4 Functional Unit," *Jour. of Virology* 70:559–565 (1996).

Yeh, P., et al., "General Organization of the Genes Specifically Involved in the Diaminopimelate–Lysine Biosynthetic Pathway of *Corynebacterium Glutamcium*," *Mol. Gen. Genet.* 212:105–111 (1988).

Yeh, P., et al., "Nucleotide Sequence of the IysA Gene of Corynebacterium Glutamincum and Possible Mechanims for Modulation of its Expression," *Mol. Gen. Genet.* 212:112–119 (1988).

Yeh, P., et al., "Radionuclide Diagnosis of Intrahepatic Lithiasis," *Annals Academy of Medicine* 15:572–580 (1986).

Yeh, P., et al., "Transfection of Corynebacterium Lilium Protoplasts," *Jour. of General Microbiology* 131:3179–3183 (1985).

Yeh, P–F., et al., "Haemophilus Infection in Chronic Obstructive Pulmonary Disease Patients," *Chin. Med. J. (Taipei)*, 44:57–60 (1989), with English translation.

Yeh, P–F., et al., "Tuberculosis Bacteremia," *China Med. J. (Taipei)* 47(4):290–293 (1991), with English translation.

Yeh, P–H., et al., "Determination of Unbound Cefamandole in Rat Blood by Microdialysis and Microbore Liquid Chromatography," *Biomedical Chromatography* 15:14–17 (2001).

Yeh, P–H., et al., "Effect of Medium–Chain Glycerides on Physiological Properties of Rabbit Intestinal Epithelium in Vitro," *Pharmaceutical Research* 11:1148–1154 (1994).

Yeh, P–H., et al., "Evaluation of Iliosoas Compartment Disorders by Computed Tomography," *Chin. Med. J (Taipei)* 55:172–179 (1995).

Yeh, P.J., et al., "Pituitary Tumors: Surgical and Medical Management," *Surgical Oncology* 6:67–92 (1997).

Yeh, P.S., et al., "Noise Analysis in Isolation of Iodine Using Three Energies," *Med. Phys.* 7:636–643 (1980).

Yeh, P–S., et al., "Chronic Focal Encephalitis (Rasmussen's Syndrome) in an Adult," *J. Formos. Med. Assoc.* 99:568–571 (2000).

Yeh, P–Y., et al., "Physiological Considerations in the Design of Particulate Dosage Forms for Oral Vaccine Delivery," *Advanced Drug Delivery Reviews* 34:123–133 (1998).

Yomo, T., et al., "Concordant Evolution of Coding and Noncoding Regions of DNA Made Possible by the Universal Rule of TA/CG Deficiency–TG/CT Excess," *Proc. Natl. Acad. Sci. USA* 86:8452–8456 (1989).

Yoneyama, T., et al., "Stable Expression of the Hepatitis B Virus Surface Antigen Containing Pre–S2 Protein in Mouse Cells Using a Bovine Papillomavirus Vector," *J. Gen. Virol.* 69:1931–1939 (1988).

Yoshida, M., et al., "Disposition Characteristics of Plasmid DNA in the Single–pass Rat Liver Perfusion System," *Pharmaceutical Research* 13:599–603 (1996).

Yoshida, N., et al., "Primary Structures of Fungal Fructosyl Amino Acid Oxidases and their Application to the Measurement of Glycated Proteins," *Eur. J. Biochem.* 242:499–505 (1996).

Zan, W–C., et al., "Protein and Gene Structure Analysis of an Albumin Genetic Variant: Proalbumin Wu Yan (−2 Arg→His)," *Int. J. Peptide Protein Res.* 41:441–446 (1993).

Zealey, G.R., et al., "Amplification of Plasmid Copy Number by Thymidine Kinase Expression in *Saccharomyces cerevisiae*," *Mol. Gen. Genet.* 211:155–159 (1988).

Zeisel, H.J., et al., "Pharmacokinetics and Short–Term Metabolic Effects of Mammalian Cell–Derived Biosynthetic Human Growth in Man," *Hormone Research* 37 (suppl 2):5–13 (1992).

Zeng, F–Y., et al., "Migration Inhibitory Factor–Binding Sarcolectin from Human Placenta is Indistingusishable from a Subfraction of Human Serum Albumin," *Biol. Chem.* 375:393–399 (1994).

Zhi, J., et al., "Influence of Human Serum Albumin Content in Formulations on the Bioequivalency of Interferon Alfa–2a Given by Subcutaneous Injection in Healthy Male Volunteers," *J. Clin. Pharmacol.* 35:281–284 (1995).

Zhong, S., et al., "Experimental Research on Inhibition of Hepatitis B Virus of Targeted Hepatocytes In Vitro by Antisense Oligonucleotides," *National Medical Journal of China* 75(7):392–395 (1995), with English translation.

Zhou, C.S., et al., "A Monoclonal Antibody Directed Against an Enediyne Antitumor Antibiotic and its Preliminary Application," *ACTA Pharmaceutica Sinica* 32(1):28–32 (1997), with English translation.

Zimmerman, T.M., et al., "Large–scale Selection of CD34+ Peripheral Blood Progenitors and expansion of Neutrophil Precursors for Clinical Applications," *Jour. of Hematotherapy* 5:247–253 (1996).

* cited by examiner

```
AAGCT TTACAACAAA TATAAAAACA ATG AAG TGG GTA ACC TTT ATT TCC CTT CTT TTT CTC TTT   -12
                                 Met Lys Trp Val Thr Phe Ile Ser Leu Leu Phe Leu Phe

AGC TCG GCT TAT TCC AGG GGT GTG TTT CGT CGA GAT GCA CAC AAG AGT GAG GTT GCT CAT    9
Ser Ser Ala Tyr Ser Arg Gly Val Phe Arg Arg Asp Ala His Lys Ser Glu Val Ala His

CGG TTT AAA GAT TTG GGA GAA GAA AAT TTC AAA GCC TTG GTG TTG ATT GCC TTT GCT CAG   29
Arg Phe Lys Asp Leu Gly Glu Glu Asn Phe Lys Ala Leu Val Leu Ile Ala Phe Ala Gln

TAT CTT CAG CAG TGT CCA TTT GAA GAT CAT CAT GAA TTA GTG AAT GAA GTA ACT GAA TTT   49
Tyr Leu Gln Gln Cys Pro Phe Glu Asp His His Glu Leu Val Lys Asn Glu Val Thr Glu Phe

GCA AAA ACA TGT GTT GCT GAT GAG TCA GCT AAA AAT TGT GAC AAA TCA CTT CAT ACC CTT   69
Ala Lys Thr Cys Val Ala Asp Glu Ser Ala Lys Asn Cys Asp Lys Ser Leu His Thr Leu

TTT GGA GAC AAA TTA TGC GCA GTT GCA ACT CTT CGT GAA ACC TAT GGT GAA ATG GCT GAC   89
Phe Gly Asp Lys Leu Cys Ala Val Ala Thr Leu Arg Glu Thr Tyr Gly Glu Met Ala Asp

TGC TGT GCA AAA CAA GAA CCT GAG AGA AAT TGC TTC TTG CAA CAC AAA GAT GAC AAC     109
Cys Cys Ala Lys Gln Glu Pro Glu Arg Asn Cys Phe Leu Gln His Lys Asp Asp Asn

CCA AAC CTC CCC CGA TTG GTG AGA CCA GAG GTT GAT GTG ATG TGC ACT GCT TTT CAT GAC   129
Pro Asn Leu Pro Arg Leu Val Arg Pro Glu Val Asp Val Met Cys Thr Ala Phe His Asp

AAT GAA GAG ACA TTT TTG AAA TAC TTA TAT GAA ATT GCC AGA AGA CAT CCT TAC TTT       149
Asn Glu Glu Thr Phe Leu Lys Tyr Leu Tyr Glu Ile Ala Arg Arg His Pro Tyr Phe

TAT GCC CCG GAA CTC CTT TTC TTT GCT AAA AGG TAT AAA GCT GCT TTT ACA GAA TGT TGC   169
Tyr Ala Pro Glu Leu Leu Phe Phe Ala Lys Arg Tyr Lys Ala Ala Phe Thr Glu Cys Cys

CAA GCT GCT GAT AAA GCT GCC TGC CTG TTG CCA AAG CTC GAT GAA CTT CGG GAT GAA GGG   189
Gln Ala Ala Asp Lys Ala Ala Cys Leu Leu Pro Lys Leu Asp Glu Leu Arg Asp Glu Gly
```

FIG. 2A

```
AAG GCT TCG TCT GCC AAA CAG AGA CTC AAG TGT GCC AGT CTC CAA AAA TTT GGA GAA AGA    209
Lys Ala Ser Ser Ala Lys Gln Arg Leu Lys Cys Ala Ser Leu Gln Lys Phe Gly Glu Arg

GCT TTC AAA GCA TGG GCA GTA GCT CGC CTG AGC CAG AGA TTT CCC AAA GCT GAG TTT GCA    229
Ala Phe Lys Ala Trp Ala Val Ala Arg Leu Ser Gln Arg Phe Pro Lys Ala Glu Phe Ala

GAA GTT TCC AAG TTA GTG ACA GAT CTT ACC AAA GTC CAC ACG GAA TGC TGC CAT GGA GAT    249
Glu Val Ser Lys Leu Val Thr Asp Leu Thr Lys Val His Thr Glu Cys Cys His Gly Asp

CTG CTT GAA TGT GCT GAT GAC AGG GCG GAC CTT GCC AAG TAT ATC TGT GAA AAT CAA GAT    269
Leu Leu Glu Cys Ala Asp Asp Arg Ala Asp Leu Ala Lys Tyr Ile Cys Glu Asn Gln Asp

TCG ATC TCC AGT AAA CTG AAG GAA TGC TGT GAA AAA CCT CTG TTG GAA AAA TCC CAC TGC    289
Ser Ile Ser Ser Lys Leu Lys Glu Cys Cys Glu Lys Pro Leu Leu Glu Lys Ser His Cys

ATT GCC GAA GTG GAA AAT GAT GAG ATG CCT GAC TTG CCT TCA TTA GCT GCT GAT TTT        309
Ile Ala Glu Val Glu Asn Asp Glu Met Pro Asp Leu Pro Ser Leu Ala Ala Asp Phe

GTT GAA AGT AAG GAT GTT TGC AAA AAC TAT GCT GAG GCA AAG GAT GTC TTC CTG GGC ATG    329
Val Glu Ser Lys Asp Val Cys Lys Asn Tyr Ala Glu Ala Lys Asp Val Phe Leu Gly Met

TTT TTG TAT GAA TAT GCA AGA AGG CAT CCT GAT TAC TCT GTA GTA CTG CTG CTG AGA CTT    349
Phe Leu Tyr Glu Tyr Ala Arg Arg His Pro Asp Tyr Ser Val Val Leu Leu Leu Arg Leu

GCC AAG ACA TAT GAA ACC ACT CTA GAG TGC TGT GCT CTT GAA GAG CCT CAT CAT GAA TGC    369
Ala Lys Thr Tyr Glu Thr Thr Leu Glu Cys Cys Ala Leu Glu Glu Pro His His Glu Cys

TAT GCC AAA GTG TTC GAT GAA TTT AAA CCT CTT GTG GAG GAG CCT CAG AAT TTA ATC AAA    389
Tyr Ala Lys Val Phe Asp Glu Phe Lys Pro Leu Val Glu Glu Pro Gln Asn Leu Ile Lys

CAA AAT TGT GAG CTT TTT GAG CAG CTT GGA GAG TAC AAA TTC CAG AAT GCG CTA TTA GTT    409
Gln Asn Cys Glu Leu Phe Glu Gln Leu Gly Glu Tyr Lys Phe Gln Asn Ala Leu Leu Val
```

FIG. 2B

```
CGT TAC ACC AAG AAA GTA CCC CAA GTG TCA ACT CTT GTA GAG GTC TCA AGA AAC   429
Arg Tyr Thr Lys Lys Val Pro Gln Val Ser Thr Leu Val Glu Val Ser Arg Asn

CTA GGA AAA GTG GGC AGC AAA TGT TGT CCT AAA CAT GCA GAA GCA AAA ATG CCC TGT GCA   449
Leu Gly Lys Val Gly Ser Lys Cys Cys Pro Lys His Ala Glu Ala Lys Met Pro Cys Ala

GAA GAC TAT CTA TCC GTG GTC CTG AAC CAG TTA TGT GTG TTG CAT GAG AAA ACG CCA GTA   469
Glu Asp Tyr Leu Ser Val Val Leu Asn Gln Leu Cys Val Leu His Glu Lys Thr Pro Val

AGT GAC AGA GTC ACC AAA TGC ACA GAA TCC TTG ACA GTG AAC AGG CGA CCA TGC TTT TCA   489
Ser Asp Arg Val Thr Lys Cys Thr Glu Ser Leu Thr Val Asn Arg Arg Pro Cys Phe Ser

GCT CTG GAA GTC GAT GAA ACA TAC GTT CCC AAA GAG TTT AAT GCT GAA ACA TTC ACC TTC   509
Ala Leu Glu Val Asp Glu Thr Tyr Val Pro Lys Glu Phe Asn Ala Glu Thr Phe Thr Phe

CAT GCA GAT ATA TGC ACA CTT TCT GAG AAG GAG AGA AAA CAA ATC AAG CAA ACT GCA CTT   529
His Ala Asp Ile Cys Thr Leu Ser Glu Lys Glu Arg Lys Gln Ile Lys Gln Thr Ala Leu

GTT GAG CTT GTG AAA CAC AAG CCC AAG GCA ACA GAG CAA CTG AAA GCT GTT ATG GAT   549
Val Glu Leu Val Lys His Lys Pro Lys Ala Thr Lys Glu Gln Leu Lys Ala Val Met Asp

GAT TTC GCA GCT TTT GTA GAG AAG TGC TGC AAG GCT GAC GAT AAG GAG ACC TGC TTT GCC   569
Asp Phe Ala Ala Phe Val Glu Lys Cys Cys Lys Ala Asp Asp Lys Glu Thr Cys Phe Ala

MstII
GAG GAG GGT AAA AAA CTT GTT GCT GCA AGT CAA GCT GCC TTA GGC TTA (NNN)p TAA GCTT
Glu Glu Gly Lys Lys Leu Val Ala Ala Ser Gln Ala Ala Leu Gly Leu  (X)p   ***
                                                                PEPTIDE
```

FIG. 2C

```
CC TTA GGC TTA        (NNN)244     TAA GCTT
  Leu Gly Leu  (Thr470->Val713)    ***
```

FIG. 4A

```
CC TTA GGC TTA        (NNN) 29     TAA GCTT
  Leu Gly Leu  (Thr470->Asp498)    ***
```

FIG. 4B

```
CC TTA GGC CTC        (NNN)14      TAA GCTT
  Leu Gly Leu  (Cys695->Pro708)    ***
              <------ D5 ------>
```

FIG. 4C

```
CC TTA GGC TTA               (NNN)90                    TAA GCTT
  Leu Gly Leu  (Thr470->Tyr508,Arg663->Val71 3)         ***
```

FIG. 4D

```
CC TTA GGC TTA ACC TGT GAA GCC TGC CAG GAG CCG GGA GGC CTG GTG GTG CCT CCC ACA    601
Leu Gly Leu Thr Cys Glu Ala Cys Gln Glu Pro Gly Gly Leu Val Val Pro Pro Thr
      SAH<--- I --->vWF470->713

GAT GCC CCG GTG AGC CCC ACC ACT CTG TAT GTG GAG GAC ATC TCG GAA CCG CCG TTG CAC    621
Asp Ala Pro Val Ser Pro Thr Thr Leu Tyr Val Glu Asp Ile Ser Glu Pro Pro Leu His

GAT TTC TAC TGC AGC AGG CTA CTG GAC CTG GTC TTC CTG GAT GGC TCC AGG CTG              641
Asp Phe Tyr Cys Ser Arg Leu Leu Asp Leu Val Phe Leu Asp Gly Ser Ser Arg Leu

TCC GAG GCT GAA TTT GAA GTG CTG AAG GCC TTT GTG GTG GAC ATG ATG GAG CGG CTG CGC    661
Ser Glu Ala Glu Phe Glu Val Leu Lys Ala Phe Val Val Asp Met Met Glu Arg Leu Arg

ATC TCC CAG AAG TGG GTC CGC GTG GCC GTG GTG GAG TAC CAC GAC GGC TCC CAC GCC TAC    681
Ile Ser Gln Lys Trp Val Arg Val Ala Val Val Glu Tyr His Asp Gly Ser His Ala Tyr

ATC GGG CTC AAG GAC CGG AAG CGA CCG TCA GAG CCG CGG CGC AAG CAG GTG AAG              701
Ile Gly Leu Lys Asp Arg Lys Arg Pro Ser Glu Pro Arg Arg Lys Gln Val Lys
```

FIG. 4E

```
TAT GCG GGC AGC CAG GTG GCC TCC ACC AGC GAG GTC TTG AAA TAC ACA CTG TTC CAA ATC
Tyr Ala Gly Ser Gln Val Ala Ser Thr Ser Glu Val Leu Lys Tyr Thr Leu Phe Gln Ile  721

TTC AGC AAG ATC GAC CGC CCT GAA GCC CTG TCC CGC ATC GCC CTG CTC CTG ATG AGC CAG
Phe Ser Lys Ile Asp Arg Pro Glu Ala Leu Ser Arg Ile Ala Leu Leu Leu Met Ser Gln  741

GAG CCC CAA CGG ATG TCC CGG AAC TTT GTC CGC TAC GTC CAG GGC CTG AAG AAG AAG AAG
Glu Pro Gln Arg Met Ser Arg Asn Phe Val Arg Tyr Val Gln Gly Leu Lys Lys Lys Lys  761

GTC ATT GTG ATC CCG GTG GGC ATT GGG CCC CAT GCC AAC CTC AAG CAG ATC CGC CTC ATC
Val Ile Val Ile Pro Val Gly Ile Gly Pro His Ala Asn Leu Lys Gln Ile Arg Leu Ile  781

GAG AAG CAG GCC CCT GAG AAC AAG GCC TTC GTG CTG AGC AGT GTG GAT GAG CTG GAG CAG
Glu Lys Gln Ala Pro Glu Asn Lys Ala Phe Val Leu Ser Ser Val Asp Glu Leu Glu Gln  801

CAA AGG GAC GAG ATC GTT AGC TAC CTC TGT GAC CTT GCC CCT GAA GCC CCT CCT CCT ACT
Gln Arg Asp Glu Ile Val Ser Tyr Leu Cys Asp Leu Ala Pro Glu Ala Pro Pro Pro Thr  821

CTG CCC CCC GAC ATG GCA CAA GTC TAA GCTT
Leu Pro Pro Asp Met Ala Gln Val ***               829
```

FIG. 4F

```
CC TTA GGC TTA AGC AAT GAA CTT CAT CAA GTT CCA TCG AAC TGT GAC TGT CTA AAT GGA   601
   Leu Gly Leu Ser Asn Glu Leu His Gln Val Pro Ser Asn Cys Asp Cys Leu Asn Gly
   SAH<--- I --->UK

GGA ACA TGT GTG TCC AAC AAG TAC TTC TCC AAC ATT CAC TGG TGC AAC TGC CCA AAG AAA   621
Gly Thr Cys Val Ser Asn Lys Tyr Phe Ser Asn Ile His Trp Cys Asn Cys Pro Lys Lys

TTC GGA GGG CAG CAC TGT GAA ATA GAT AAG TCA AAA ACC TGC TAT GAG TAT CGT GGT CAC   641
Phe Gly Gly Gln His Cys Glu Ile Asp Lys Ser Lys Thr Cys Tyr Glu Tyr Asn Gly His
                    EGF-LIKE<--- I --->KRINGLE

TTT TAC CGA GGA AAG GCC AGC ACT GAC ACC ATG GGC CGG CCC TGC CTG CCC TGG AAC TCT   661
Phe Tyr Arg Gly Lys Ala Ser Thr Asp Thr Met Gly Arg Pro Cys Leu Pro Trp Asn Ser

GCC ACT GTC CTT CAG CAA ACG TAC CAT GCC CAC AGA TCT GAT GCT CTT CAG CTG GGC CTG   681
Ala Thr Val Leu Gln Gln Thr Tyr His Ala His Arg Ser Asp Ala Leu Gln Leu Gly Leu

GGG AAA CAT AAT TAC TGC AGG AAC CCA GAC AAC CGA AGG AGG CCC TGG TGC TAT GTG CAG   701
Gly Lys His Asn Tyr Cys Arg Asn Pro Asp Asn Arg Arg Arg Pro Trp Cys Tyr Val Gln

GTG GGC CTA AAG CCG CTT GTC CAA GAG TGC ATG GTG CAT GAC TGC GCA GAT GGA AAA TAA   720
Val Gly Leu Lys Pro Leu Val Gln Glu Cys Met Val His Asp Cys Ala Asp Gly Lys ***

GCTT
```

FIG. 8

```
                           ApaI
CC TTA GGC TTA ACC CCC CTG GGC CCT GCC AGC TCC CTG CCC CAG AGC TTC CTG CTC AAG    601
   Leu Gly Leu Thr Pro Leu Gly Pro Ala Ser Ser Leu Pro Gln Ser Phe Leu Leu Lys
   SAH<--- I --->G-CSF

TGC TTA GAG GAG GTG AGG AAG ATC CAG GGC GAT GGC GCA GCG CTC CAG GAG AAG CTG TGT    621
Cys Leu Glu Glu Val Arg Lys Ile Gln Gly Asp Gly Ala Ala Leu Gln Glu Lys Leu Cys

GCC ACC TAC AAG CTG TGC CAC CCC GAG GAG CTG GTG CTG CTC GGA CAC TCT CTG GGC ATC    641
Ala Thr Tyr Lys Leu Cys His Pro Glu Glu Leu Val Leu Leu Gly His Ser Leu Gly Ile

SstI
CCC TGG GCT CCC CTG AGC TCC TGC CCC AGC CAG CAG GCC CTG CAG CTG GCA GGC TGC TTG AGC    661
Pro Trp Ala Pro Leu Ser Ser Cys Pro Ser Gln Gln Ala Leu Gln Leu Ala Gly Cys Leu Ser

CAA CTC CAT AGC GGC CTT TTC CTC TAC CAG GGG CTC CTG CAG GCC CTG GAA GGG AGA TCC    681
Gln Leu His Ser Gly Leu Phe Leu Tyr Gln Gly Leu Leu Gln Ala Leu Glu Gly Ile Ser

CCC GAG TTG GGT CCC ACC TTG GAC ACA CTG CAG CTG GAC GTC GCC GAC TTT GCC ACC ACC    701
Pro Glu Leu Gly Pro Thr Leu Asp Thr Leu Gln Leu Asp Val Ala Asp Phe Ala Thr Thr

ATC TGG CAG CAG ATG GAA GAA CTG GGA ATG GCC CCT GCC CTG CAG CCC ACC CAG GGT GCC    721
Ile Trp Gln Gln Met Glu Glu Leu Gly Met Ala Pro Ala Leu Gln Pro Thr Gln Gly Ala

ATG CCG GCC TTC GCC TCT GCT TTC CAG CGC CGG GCA GGA GGG GTC CTG GTT GCT AGC CAT    741
Met Pro Ala Phe Ala Ser Ala Phe Gln Arg Arg Ala Gly Gly Val Leu Val Ala Ser His

CTG CAG AGC TTC CTG GAG GTG TCG TAC CGC GTT CTA CGC CAC CTT GCG CAG CCC TGA AGCTT  759
Leu Gln Ser Phe Leu Glu Val Ser Tyr Arg Val Leu Arg His Leu Ala Gln Pro ***
```

FIG. 10

```
AAGCT TTACAACAAA TATAAAAACA ATG AAG TGG GTA ACC TTT ATT TCC CTT CTT TTT CTC TTT   -12
                            Met Lys Trp Val Thr Phe Ile Ser Leu Leu Phe Leu Phe
                                                              ApaI
AGC TCG GCT TAT TCC AGG GGT GTG TTT CGT CGA ACC CTG GGC CCT GCC AGC TCC CTG          9
Ser Ser Ala Tyr Ser Arg Gly Val Phe Arg Arg Thr Pro Leu Gly Pro Ala Ser Ser Leu
                                             [--->G-CSF

CCC CAG AGC TTC CTG CTC AAG TGC TTA GAG CAA GTG AGG AAG ATC CAG GGC GAT GGC GCA     29
Pro Gln Ser Phe Leu Leu Lys Cys Leu Glu Gln Val Arg Lys Ile Gln Gly Asp Gly Ala

GCG CTC CAG GAG AAG CTG TGT TGT GCC ACC TAC AAG CTG TGC CAC CCC GAG GAG CTG CTG     49
Ala Leu Gln Glu Lys Leu Cys Cys Ala Thr Tyr Lys Leu Cys His Pro Glu Glu Val Leu
                                             SstI
CTC GGA CAC TCT CTG GGC ATC CCC TGG GCT CCC CTG AGC TCC TGC CCC AGC CAG GCC CTG     69
Leu Gly His Ser Leu Gly Ile Pro Trp Ala Pro Leu Ser Ser Cys Pro Ser Gln Ala Leu

CAG CTG GCA GGC TGC TTG AGC CAA CTC CAT AGC GGC CTT TTC CTC TAC CAG GGG CTC CTG     89
Gln Leu Ala Gly Cys Leu Ser Gln Leu His Ser Gly Leu Phe Leu Tyr Gln Gly Leu Leu

CAG GCC CTG GAA GGG ATA TCC CCC GGT TTG GGT CCC ACC TTG GAC ACA CTG CAG CTG GAC    109
Gln Ala Leu Glu Gly Ile Ser Pro Gly Leu Gly Pro Thr Leu Asp Thr Leu Gln Leu Asp

GTG GCC GAC TTT GCC ACC ACC ATC TGG CAG CAG ATG GAA GAA CTG GGA ATG GCC CCT GCC    129
Val Ala Asp Phe Ala Thr Thr Ile Trp Gln Gln Met Glu Glu Leu Gly Met Ala Pro Ala

CTG CAG CCC ACC CAG GGT GCC ATG CCG GCC TTC GCT TCT GCT TTC CAG CGC CGG GCA GGA    149
Leu Gln Pro Thr Gln Gly Ala Met Pro Ala Phe Ala Ser Ala Phe Gln Arg Arg Ala Gly

GGG GTC CTG GTT GCT AGC CAT CTG CAG AGC TTC CTG GAG GTG TCG TAC CGC GTT CTA CGC    169
Gly Val Leu Val Ala Ser His Leu Gln Ser Phe Leu Glu Val Ser Tyr Arg Val Leu Arg
```

FIG. IIA

```
CAC CTT GCG CAG CCC GGT GGA GGC GGT GAT GCA CAC AAG AGT GAG GTT GCT CAT CGG TTT
His Leu Ala Gln Pro Gly Gly Gly Gly Asp Ala His Lys Ser Glu Val Ala His Arg Phe  189
      G-CSF<--- I    linker    I --->SAH AAA GAT TTG GGA GAA GAA AAT TTC AAA GCC TTG GTG TTG ATT GCC TTT GCT CAG TAT CTT
Lys Asp Leu Gly Glu Glu Asn Phe Lys Ala Leu Val Leu Ile Ala Phe Ala Gln Tyr Leu  209

CAG CAG TGT CCA TTT GAA GAT CAT GTA AAA TTA GTG AAT GAA GTA ACT GAA TTT GCA AAA
Gln Gln Cys Pro Phe Glu Asp His Val Lys Leu Val Asn Glu Val Thr Glu Phe Ala Lys  229

ACA TGT GTT GCT GAT GAG TCA GCT GAA AAT TGT GAC AAA TCA CTT CAT ACC CTT TTT GGA
Thr Cys Val Ala Asp Glu Ser Ala Glu Asn Cys Asp Lys Ser Leu His Thr Leu Phe Gly  249

GAC AAA TTA TGC ACA GTT GCA ACT CTT CGT GAA ACC TAT GGT GAA ATG GCT GAC TGC TGT
Asp Lys Leu Cys Thr Val Ala Thr Leu Arg Glu Thr Tyr Gly Glu Met Ala Asp Cys Cys  269

GCA AAA CAA GAA CCT GAG AGA AAT GAA TGC TTC TTG CAA CAC AAA GAT GAC AAC CCA AAC
Ala Lys Gln Glu Pro Glu Arg Asn Glu Cys Phe Leu Gln His Lys Asp Asp Asn Pro Asn  289

CTC CCC CGA TTG GTG AGA CCA GAG GTT GAT GTG ATG TGC ACT GCT TTT CAT GAC AAT GAA
Leu Pro Arg Leu Val Arg Pro Glu Val Asp Val Met Cys Thr Ala Phe His Asp Asn Glu  309

GAG ACA TTT TTG AAA AAA TAC TTA TAT GAA ATT GCC AGA AGA CAT CCT TAC TTT TAT GCC
Glu Thr Phe Leu Lys Lys Tyr Leu Tyr Glu Ile Ala Arg Arg His Pro Tyr Phe Tyr Ala  329

CCG GAA CTC CTT TTC TTT GCT AAA AGG TAT AAA GCT GCT TTT ACA GAA TGT TGC CAA GCT
Pro Glu Leu Leu Phe Phe Ala Lys Arg Tyr Lys Ala Ala Phe Thr Glu Cys Cys Gln Ala  349

GCT GAT AAA GCT GCC TGC CTG TTG CCA AAG CTC GAT GAA CTT CGG GAT GAA GGG AAG GCT
Ala Asp Lys Ala Ala Cys Leu Leu Pro Lys Leu ASP Glu Leu Arg Asp Glu Gly Lys Ala  369

TCG TCT GCC AAA CAG AGA CTC AAG TGT GCC AGT CTC CAA AAA TTT GGA GAA AGA GCT TTC
Ser Ser Ala Lys Gln Arg Leu Lys Cys Ala Ser Leu Gln Lys Phe Gly Glu Arg Ala Phe  389
```

FIG. 11B

```
AAA GCA TGG GCA GTA GCT CGC CTG AGC CAG AGA TTT CCC AAA GCT GAG TTT GCA GAA GTT    409
Lys Ala Trp Ala Val Ala Arg Leu Ser Gln Arg Phe Pro Lys Ala Glu Phe Ala Glu Val

TCC AAG TTA GTG ACA GAT CTT ACC AAA GTC CAC ACG GAA TGC CAT GGA GAT CTG CTT        429
Ser Lys Leu Val Thr Asp Leu Thr Lys Val His Thr Glu Cys His Gly Asp Leu Leu

GAA TGT GCT GAT GAC AGG GCG GAC CTT GCC AAG TAT ATC TGT GAA AAT CAA GAT TCG ATC    449
Glu Cys Ala Asp Asp Arg Ala Asp Leu Ala Lys Tyr Ile Cys Glu Asn Gln Asp Ser Ile

TCC AGT AAG CTG GAA TGC TGT GAA AAA CCT CTG GAA TTG AAA TCC CAC TGC ATT GCC        469
Ser Ser Lys Leu Glu Cys Cys Glu Lys Pro Leu Glu Leu Lys Ser His Cys Ile Ala

GAA GTG GAA AAT GAT GAG ATG CCT GCT GAC TTG CCT TCA GCT GCT GAT TTT GTT GAA        489
Glu Val Glu Asn Asp Glu Met Pro Ala Asp Leu Pro Ser Leu Ala Ala Asp Phe Val Glu

AGT AAG GAT GTT TGC AAA AAC TAT GCT GAG GCA AAG GAT GTC TTC CTG GGC ATG TTT TTG    509
Ser Lys Asp Val Cys Lys Asn Tyr Ala Glu Ala Lys Asp Val Phe Leu Gly Met Phe Leu

TAT GAA TAT GCA AGA AGG CAT CCT GAT TAC TCT GTC CTG CTG CTG AGA CTT GCC AAG        529
Tyr Glu Tyr Ala Arg Arg His Pro Asp Tyr Ser Val Leu Leu Leu Arg Leu Ala Lys

ACA TAT GAA ACC ACT CTA GAG AAG TGC TGT GCA GCT GCA GAT CCT CAT GAA TGC TAT GCC    549
Thr Tyr Glu Thr Thr Leu Glu Lys Cys Cys Ala Ala Ala Asp Pro His Glu Cys Tyr Ala

AAA GTG TTC GAT GAA TTT AAA CCT CTT GTG GAA GAG CCT CAG AAT TTA ATC AAA CAA AAT    569
Lys Val Phe Asp Glu Phe Lys Pro Leu Val Glu Glu Pro Gln Asn Leu Ile Lys Gln Asn

TGT GAG CTT TTT GAG CAG CTT GGA GAG TAC AAA TTC CAG AAT GCG CTA TTA GTT CGT TAC    589
Cys Glu Leu Phe Glu Gln Leu Gly Glu Tyr Lys Phe Gln Asn Ala Leu Leu Val Arg Tyr

ACC AAG AAA GTA CCC CAA GTG TCA ACT CCA ACT CTT GTA GAG GTC TCA AGA AAC CTA GGA    609
Thr Lys Lys Val Pro Gln Val Ser Thr Pro Thr Leu Val Glu Val Ser Arg Asn Leu Gly
```

FIG. IIC

```
AAA GTG GGC AGC AAA TGT TGT AAA CAT CCT GAA GCA AAA AGA ATG CCC TGT GCA GAA GAC      629
Lys Val Gly Ser Lys Cys Cys Lys His Pro Glu Ala Lys Arg Met Pro Cys Ala Glu Asp

TAT CTA TCC GTG GTC CTG AAC CAG TTA TGT GTG TTG CAT GAG AAA ACG CCA GTA AGT GAC      649
Tyr Leu Ser Val Val Leu Asn Gln Leu Cys Val Leu His Glu Lys Thr Pro Val Ser Asp

AGA GTC ACC AAA TGC TGC ACA GAA TCC ACA GAA TTG GTG AAC AGG CGA CCA TGC TTT TCA GCT CTG   669
Arg Val Thr Lys Cys Cys Thr Glu Ser Thr Glu Leu Val Asn Arg Arg Pro Cys Phe Ser Ala Leu

GAA GTC GAT GAA ACA TAC GTT CCC AAA GAG TTT AAT GCT GAA ACA TTC ACC TTC CAT GCA       689
Glu Val Asp Glu Thr Tyr Val Pro Lys Glu Phe Asn Ala Glu Thr Phe Thr Phe His Ala

GAT ATA TGC ACA CTT TCT GAG AAG GAG CAA ATC AAG AAA CAA ACT GCA CTT GTT GAG           709
Asp Ile Cys Thr Leu Ser Glu Lys Glu Gln Ile Lys Lys Gln Thr Ala Leu Val Glu

CTT GTG AAA CAC AAG CCC AAG GCA ACA AAA GAG CAA CTG AAA GCT GTT ATG GAT GAT TTC       729
Leu Val Lys His Lys Pro Lys Ala Thr Lys Glu Gln Leu Lys Ala Val Met Asp Asp Phe

GCA GCT TTT GTA GAG AAG TGC TGC AAG GCT GAC GAT AAG GAG ACC TGC TTT GCC GAG GAG       749
Ala Ala Phe Val Glu Lys Cys Cys Lys Ala Asp Asp Lys Glu Thr Cys Phe Ala Glu Glu

MstII
GGT AAA AAA CTT GTT GCT GCA AGT CAA GCT GCC TTA GGC TTA TAA CATCACATT                 763
Gly Lys Lys Leu Val Ala Ala Ser Gln Ala Ala Leu Gly Leu ***

AAAAGCATCT CAGCCTACCA TGAGAATAAG AGAAAGAAAA TGAAGATCAA AAGCTT
```

FIG. 1 ID

```
                                                                              601
CC TTA GGC TTA CAG GTG CAG CTC GAG CAG TCT GGA CCT GAG CTG GTG AAG CCT GGG GCC
   Leu Gly Leu Gln Val Gln Leu Glu Gln Ser Gly Pro Glu Leu Val Lys Pro Gly Ala
   SAH< --- I--->VH

621
TCA GTG AAG ATT TCC TGC AAA GCT TCT GGC TAC GCA TTC AGT AGG TCT TGG ATG AAC TGG
Ser Val Lys Ile Ser Cys Lys Ala Ser Gly Tyr Ala Phe Ser Arg Ser Trp Met Asn Trp

641
GTG AAG CAG AGG CCT GGA CAG GGT CTT GAG TGG ATT GGA CGG ATT TAT CCT GGA GAT GGA
Val Lys Gln Arg Pro Gly Gln Gly Leu Glu Trp Ile Gly Arg Ile Tyr Pro Gly Asp Gly

661
GAT ACC AAA TAC AAT GGG AAG TTC AAG GGC AAG GCC ACA CTG ACT GCG GAC AGA TCA TCC
Asp Thr Lys Tyr Asn Gly Lys Phe Lys Gly Lys Ala Thr Leu Thr Ala Asp Arg Ser Ser

681
AGC ACA GCC TAC ATG CAG CTC AGC CTG ACC TCT GTG GGC TCT GCG GTC TAT TTC TGT
Ser Thr Ala Tyr Met Gln Leu Ser Leu Thr Ser Val Gly Ser Ala Val Tyr Phe Cys

701
GCA AAA GAG AAC AAT AGG TTC GAC GAG AGG GGT TAC TAT GCT ATG GAC TAC TGG GGC CAA
Ala Lys Glu Asn Asn Arg Phe Asp Glu Arg Gly Tyr Tyr Ala Met Asp Tyr Trp Gly Gln

721
GGG ACC ACG GTC ACC GTC TCC TCA GGT GGT GGT GGC TCG GGC GGT GGG TCG GGT GGC
Gly Thr Thr Val Thr Val Ser Ser Gly Gly Gly Gly Ser Gly Gly Gly Ser Gly Gly
    VH< ---               Synthetic linker
```

FIG. 14A

```
GGC GGA TCT AAC ATT CAG TTG ACC CAG TCT CCA AAT TCC ATG TCC ACA GTA GGA GAC     741
Gly Gly Ser Asn Ile Gln Leu Thr Gln Ser Pro Asn Ser Met Ser Thr Val Gly Asp
      I--->VL

AGG GTC AGC ATC ACC TGC AAG GCC AGT CAG GAT GTG GAT ACT TCT GTA GCC TGG TAT CAA  761
Arg Val Ser Ile Thr Cys Lys Ala Ser Gln Asp Val Asp Thr Ser Val Ala Trp Tyr Gln

CAG AAA CCA GGG CAA TCT CCT AAA CTA CTG ATT TAC TGG GCA TCC ACC CGG CAC ACT GGA  781
Gln Lys Pro Gly Gln Ser Pro Lys Leu Leu Ile Tyr Trp Ala Ser Thr Arg His Thr Gly

GTC CCT GAT CGC TTC ACA GGC AGT GGA TCT GGG ACA GAT TTC ACT CTC ACC ATT AGC AAT  801
Val Pro Asp Arg Phe Thr Gly Ser Gly Ser Gly Thr Asp Phe Thr Leu Thr Ile Ser Asn

GTG CAG TCT GAA GAC TCG GCA GAT TAT TTC TGT CAG CAA TAT AGC TAT CCG TGG ACG      821
Val Gln Ser Glu Asp Ser Ala Asp Tyr Phe Cys Gln Gln Tyr Ser Tyr Pro Trp Thr

TTC GGT GGA GGG ACC AAG CTG GAG ATC AAA TAA GCTT                                 831
Phe Gly Gly Gly Thr Lys Leu Glu Ile Lys ***
```

FIG. 14B

| PRODUCT | IC$_{50}$ (nM) |
|---|---|
| RG12986 | 50 |
| HSA-vWF 694-708 | 50000 |
| HSA-vWF 470-713 C471,474→G | 20 |
| HSA-vWF 470-704 C471,474→G | <10 |

FUSION POLYPEPTIDES OF HUMAN SERUM ALBUMIN AND A THERAPEUTICALLY ACTIVE POLYPEPTIDE

This is a continuation of application Ser. No. 09/258,532, filed Feb. 26, 1999, now abandoned, which is a divisional of Ser. No. 08/797,689, filed Jan. 31, 1997 and now U.S. Pat. No. 5,876,969, which is a continuation of Ser. No. 08/256,927 filed Jul. 28, 1994, now abandoned, which is based on PCT/FR93/00085, filed Jan. 28, 1993, which is a priority application based on French Application 92-01064, filed Jan. 31, 1992, which are incorporated herein by reference.

The present invention relates to new biologically active polypeptides, their preparation and pharmaceutical compositions containing them.

More particularly, the present invention relates to essentially recombinant polypeptides composed of an active part derived from a natural or artificial polypeptide having a therapeutic activity and coupled to an albumin or to a variant of albumin. It is understood that the therapeutic activity of the polypeptides of the invention can be either direct (treatment of diseases), or indirect (and for example capable of being used in the prevention of diseases, in the design of vaccines, in medical imaging techniques and the like).

It is understood in the following text that the albumin variants designate any protein with a high plasma half-life which is obtained by modification (mutation, deletion and/or addition), by genetic engineering techniques, of a gene encoding a given isomorph of human serum albumin, as well as any macromolecule with a high plasma half-life obtained by in vitro modification of the protein encoded by such genes. Albumin being highly polymorphic, numerous natural variants have been identified and classified [Weitkamp L. R. et al., Ann. Hum. Genet. 37 (1973) 219].

The aim of the present invention is to prepare artificial proteins which are biologically active and can be used pharmaceutically. Indeed, numerous polypeptides possessing one or more potential therapeutic activities cannot be exploited pharmaceutically. This may have various reasons, such as especially their low stability in vivo, their complex or fragile structure, the difficulty of producing them on an industrially acceptable scale and the like. Likewise, some polypeptides do not give the expected results in vivo because of problems of administration, of packaging, of pharmacokinetics and the like.

The present invention makes it possible to overcome these disadvantages. The present invention indeed provides new molecules which permit an optimal therapeutic exploitation of the biological properties of these polypeptides. The present invention results especially from the demonstration that it is possible to couple genetically any active structure derived from a biologically active polypeptide to another protein structure consisting of albumin, without impairing the said biological properties thereof. It also results from the demonstration by the Applicant that human serum albumin makes it possible efficiently to present the active structure to its sites for interaction, and that it provides a high plasma stability for the polypeptide of the invention. The polypeptides of the invention thus make it possible to maintain, in the body, a given biological activity for a prolonged period. They thus make it possible to reduce the administered doses and, in some cases, to potentiate the therapeutic effect, for example by reducing the side effects following a higher administration. The polypeptides of the invention make it possible, in addition, to generate and to use structures derived from biologically active polypeptides which are very small and therefore very specific for a desired effect. It is understood that the peptides having a biological activity, which are of therapeutic interest, may also correspond to non-natural peptide sequences isolated for example from random peptide libraries. The polypeptides of the invention possess, moreover, a particularly advantageous distribution in the body, which modifies their pharmacokinetic properties and favours the development of their biological activity and their use. In addition, they also have the advantage of being weakly or non-immunogenic for the organism in which they are used. Finally, the polypeptides of the invention can be expressed (and preferentially secreted) by recombinant organisms, at levels permitting their industrial exploitation.

One subject of the present invention therefore relates to polypeptides containing an active part derived from a polypeptide having a therapeutic activity, coupled to an albumin or a variant of albumin.

In a specific embodiment, the peptides possessing a therapeutic activity are not of human origin. For example, there may be mentioned peptides, or their derivatives, possessing properties which are potentially useful in the pathologies of the blood and interstitial compartments, such as hirudin, trigramine, antistatine, tick anticoagulant peptides (TAP), arietin, applagin and the like.

More particularly, in the molecules of the invention, the polypeptide having a therapeutic activity is a polypeptide of human origin or a molecular variant. For example, this may be all or part of an enzyme, an enzyme inhibitor, an antigen, an antibody, a hormone, a factor involved in the control of coagulation, an interferon, a cytokine [the interleukins, but also their variants which are natural antagonists of their binding to the receptor(s), the SIS (small induced secreted) type cytokines and for example the macrophage inflammatory proteins (MIPs), and the like], of a growth factor and/or of differentiation [and for example the transformant growth factors (TGFs), the blood cell differentiation factors (erythropoietin, M-CSF, G-CSF, GM-CSF and the like), insulin and the growth factors resembling it (IGFs), or alternatively cell permeability factors (VPF/VEGF), and the like], of a factor involved in the genesis/resorption of bone tissues (OIF and osteospontin for example), of a factor involved in cellular motility or migration [and for example autocrine motility factor (AMF), migration stimulating factor (MSF), or alternatively the scatter factor (scatter factor/hepatocyte growth factor)], of a bactericidal or antifungal factor, of a chemotactic factor [and for example platelet factor 4 (PF4), or alternatively the monocyte chemoattracting peptides (MCP/MCAF) or neutrophil chemoattracting peptides (NCAF), and the like], of a cytostatic factor (and for example the proteins which bind to galactosides), of a plasma (and for example von Willebrand factor, fibrinogen and the like) or interstitial (laminin, tenascin, vitronectin and the like) adhesive molecule or extracellular matrices, or alternatively any peptide sequence which is an antagonist or agonist of molecular and/or intercellular interactions involved in the pathologies of the circulatory and interstitial compartments and for example the formation of arterial and venous thrombi, cancerous metastases, tumour angiogenesis, inflammatory shock, autoimmune diseases, bone and osteoarticular pathologies and the like.

The active part of the polypeptides of the invention may consist for example of the polypeptide having a whole therapeutic activity, or of a structure derived therefrom, or alternatively of a non-natural polypeptide isolated from a peptide library. For the purposes of the present invention, a derived structure is understood to mean any polypeptide obtained by modification and preserving a therapeutic activity. Modification should be understood to mean any mutation, substitution, deletion, addition or modification of genetic and/or chemical nature. Such derivatives may be generated for various reasons, such as especially that of increasing the affinity of the molecule for its binding sites, that of improving its levels of production, that of increasing its resistance to proteases, that of increasing its therapeutic efficacy or alternatively of reducing its side effects, or that of conferring on it new biological properties. As an example, the chimeric polypeptides of the invention possess pharmacokinetic properties and a biological activity which can be used for the prevention or treatment of diseases.

Particularly advantageous polypeptides of the invention are those in which the active part has:
  (a) the whole peptide structure or,
  (b) a structure derived from (a) by structural modification (mutation, substitution addition and/or deletion of one or more residues) and possessing a therapeutic activity.

Among the structures of the (b) type, there may be mentioned more particularly the molecules in which certain N- or 0-glycosylation sites have been modified or suppressed, the molecules in which one or more residues have been substituted, or the molecules in which all the cystein residues have been substituted. There may also be mentioned molecules obtained from (a) by deletion of regions not involved or not highly involved in the interaction with the binding sites considered, or expressing an undesirable activity, and molecules containing, compared to (a), additional residues such as for example an N-terminal methionine and/or a signal for secretion and/or a Joining peptide.

The active part of the molecules of the invention can be coupled either directly or via an artificial peptide to albumin. Furthermore, it may constitute the N-terminal end as well as the C-terminal end of the molecule. Preferably, in the molecules of the invention, the active part constitutes the C-terminal part of the chimera. It is also understood that the biologically active part may be repetitive within the chimera. A schematic representation of the molecules of the invention is given in FIG. 1.

Another subject of the invention relates to a process for preparing the chimeric molecules described above. More specifically, this process consists in causing a eukaryotic or prokaryotic cellular host to express a nucleotide sequence encoding the desired polypeptide, and then in harvesting the polypeptide produced.

Among the eukaryotic hosts which can be used within the framework of the present invention, there may be mentioned animal cells, yeasts or fungi. In particular, as regards yeasts, there may be mentioned yeasts of the genus Saccharomyces, Kluyveromyces, Pichia, Schwanniomyces, or Hansenula. As regards animal cells, there may be mentioned COS, CHO and C127 cells and the like. Among the fungi capable of being used in the present invention, there may be mentioned more particularly Aspergillus ssp, or Trichoderma ssp. As prokaryotic hosts, the use of bacteria such as *Escherichia coli*, or belonging to the genera Corynebacterium, Bacillus, or Streptomyces is preferred.

The nucleotide sequences which can be used within the framework of the present invention can be prepared in various ways. Generally, they are obtained by assembling, in reading phase, the sequences encoding each of the functional parts of the polypeptide. The latter may be isolated by the techniques of persons skilled in the art, and for example directly from cellular messenger RNAs (mRNAs), or by recloning from a complementary DNA (cDNA) library, or alternatively they may be completely synthetic nucleotide sequences. It is understood, furthermore, that the nucleotide sequences may also be subsequently modified, for example by the techniques of genetic engineering, in order to obtain derivatives or variants of the said sequences.

More preferably, in the process of the invention, the nucleotide sequence is part of an expression cassette comprising a region for initiation of transcription (promoter region) permitting, in the host cells, the expression of the nucleotide sequence placed under its control and encoding the polypeptides of the invention. This region may come from promoter regions of genes which are highly expressed in the host cell used, the expression being constitutive or regulatable. As regards yeasts, it may be the promoter of the gene for phosphoglycerate kinase (PGK), glyceraldehyde-3-phosphate dehydrogenase (GPD), lactase (LAC4), enolases (ENO), alcohol dehydrogenases (ADH), and the like. As regards bacteria, it may be the promoter of the right-hand or left-hand genes from the lambda bacteriophage (PL, PR), or alternatively the promoters of the genes for the tryptophan (Ptrp) or lactose (Plac) operons. In addition, this control region can be modified, for example by in vitro mutagenesis, by the introduction of additional control elements or of synthetic sequences, or by deletions or substitutions of the original control elements. The expression cassette may also comprise a region for termination of transcription which is functional in the host envisaged, positioned immediately downstream of the nucleotide sequence encoding a polypeptide of the invention.

In a preferred mode, the polypeptides of the invention result from the expression, in a eukaryotic or prokaryotic host, of a nucleotide sequence and from the secretion of the product of expression of the said sequence into the culture medium. It is indeed particularly advantageous to be able to obtain, by the recombinant route, molecules directly in the culture medium. In this case, the nucleotide sequence encoding a polypeptide of the invention is preceded by a "leader" sequence (or signal sequence) directing the nascent polypeptide in the secretory pathways of the host used. This "leader" sequence may be the natural signal sequence of the biologically active polypeptide in the case where the latter is a naturally secreted protein, or that of the stabilizing structure, but it may also be any other functional "leader" sequence, or an artificial "leader" sequence. The choice of one or the other of these sequences is especially guided by the host used. Examples of functional signal sequences include those of the genes for the sexual pheromones or the "killer" toxins of yeasts.

In addition to the expression cassette, one or several markers which make it possible to select the recombinant host may be added, such as for example the URA3 gene from the yeast *S. cerevisiae*, or genes conferring the resistance to antibiotics such as geneticin (G418) or to any other toxic compound such as certain metal ions.

The unit formed by the expression cassette and by the selectable marker can be introduced directly into the considered host cells, or previously inserted in a functional self-replicating vector. In the first case, sequences homologous to regions present in the genome of the host cells are preferably added to this unit; the said sequences then being positioned on each side of the expression cassette and of the selectable gene so as to increase the frequency of integration of the unit into the genome of the host by targetting the integration of the sequences by homologous recombination. In the case where the expression cassette is inserted in a replicative system, a preferred replication system for yeasts of the genus Kluyveromyces is derived from the plasmid pKD1 originally isolated from *K drosophilarum*; a preferred replication system for yeasts of the genus Saccharomyces is derived from the 2μ plasmid from *S. cerevisiae*. Furthermore, this expression plasmid may contain all or part of the said replication systems, or may combine elements derived both from the plasmid pKD1 and the 2μ plasmid.

In addition, the expression plasmids may be shuttle vectors between a bacterial host such as *Escherichia coli* and the chosen host cell. In this case, a replication origin and a selectable marker functioning in the bacterial host are required. It is also possible to position restriction sites surrounding the bacterial and unique sequences on the expression vector: this makes it possible to suppress these sequences by cutting and religation in vitro of the truncated vector before transformation of the host cells, which may result in an increase in the number of copies and in an increased stability of the expression plasmids in the said hosts. For example, such restriction sites may correspond to sequences such as 5'-GGCCNNNNNGGCC-3' SEQ ID NO: 19 (SfiI) or 5'-GCGGCCGC-3' (NotI) in so far as these sites are extremely rare and generally absent from an expression vector.

After construction of such vectors or expression cassette, the latter are introduced into the host cells selected according to the conventional techniques described in the literature. In this respect, any method permitting the introduction of a foreign DNA into a cell can be used. This may be especially transformation, electroporation, conjugation, or any other technique known to persons skilled in the art. As an example of yeast-type hosts, the various strains of Kluyveromyces used were transformed by treating the whole cells in the presence of lithium acetate and polyethylene glycol, according to the technique described by Ito et al. [J. Bacteriol. 153 (1983) 163]. The transformation technique described by Durrens et al. [Curr. Genet. 18 (1990) 7] using ethylene glycol and dimethyl sulphoxide was also used. It is also possible to transform the yeasts by electroporation, according to the method described by Karube et al. [FEBS Letters 182 (1985) 90]. An alternative procedure is also described in detail in the examples below.

After selection of the transformed cells, the cells expressing the said polypeptides are inoculated and the recovery of the said polypeptides can be carried out, either during the cell growth for the "continuous" processes, or at the end of growth for the "batch" cultures. The polypeptides which are the subject of the present invention are then purified from the culture supernatant for their molecular, pharmacokinetic and biological characterization.

A preferred expression system for the polypeptides of the invention consists in using yeasts of the genus Kluyveromyces as host cell, transformed by certain vectors derived from the extrachromosomal replicon pKD1 originally isolated from *K. marxianus var. drosophilarum*. These yeasts, and in particular *K. lactis* and *K. fragilis* are generally capable of stably replicating the said vectors and possess, in addition, the advantage of being included in the list of G.R.A.S. ("Generally Recognized As Safe") organisms. Favoured yeasts are preferably industrial yeasts of the genus Kluyveromyces which are capable of stably replicating the said plasmids derived from the plasmid pKD1 and in which has been inserted a selectable marker as well as an expression cassette permitting the secretion, at high levels, of the polypeptides of the invention.

The present invention also relates to the nucleotide sequences encoding the chimeric polypeptides described above, as well as the eukaryotic or prokaryotic recombinant cells comprising such sequences.

The present invention also relates to the application, as medicinal products, of the polypeptides according to the present invention. More particularly, the subject of the invention is any pharmaceutical composition comprising one or more polypeptides or nucleotide sequences as described above. The nucleotide sequences can indeed be used in gene therapy.

The present invention will be more fully described with the aid of the following examples, which should be considered as illustrative and non-limiting.

BRIEF DESCRIPTION OF THE DRAWINGS

The representations of the plasmids indicated in the following figures are not plotted to scale and only the restriction sites important for the understanding of the clonings carried out have been indicated.

FIGS. 2(*a*) and 2(*b*), together, comprise an example of a nucleotide sequence (SEQ ID NO: 1) and an amino acid sequence (SEQ ID NO:2) of a HindIII restriction fragment encoding a chimeric protein of the prepro-HSA-PEPTIDE type. The black arrows indicate the end of the "pre" and "pro" regions of HSA. The MstII restriction site is underligned and the codon specifying the termination of translation is in bold characters.

FIGS. 4A, 4B, 4C, 4D, and 4E collectively show examples of nucleotide sequences of MstII-HindIII restriction fragments derived from the von Willebrand factor. FIG. 4A is a representation of the structure of the MstII-HindIII fragment of the plasmid pYG1248 (SEQ ID NOS:3 and 4). FIG. 4B is a representation of the structure of the MstII-HindIII fragment of the plasmid pYG1214 (SEQ ID NOS:5 and 6). FIG. 4C is a representation of the MstII-HindIII fragment of the plasmid pYG1206; in this particular chimera, the Leu694 residue of the vWF is also the last residue (Leu585) of the HSA. FIG. 4D is a representation of the MstII-HindIII fragment of the plasmid pYG1223 (SEQ ID NOS:9 and 10). The numbering of the amino acids corresponds to the numbering of the mature vWF according to Titani et al. [Biochemistry 25 (1986) 3171–3184]. The MstII and HindIII restriction sites are underlined and the translation termination codon is in bold characters. FIG. 4E is a nucleotide sequence (SEQ ID NO:3) of the MstII-HindIII restriction fragment of the plasmid pYG1248. The numbering of the amino acids (right-hand column) corresponds to the mature chimeric protein HSA-vWF470→713 (829 residues). The Thr470, Leu494, Asp498, Pro502, Tyr508, Leu694, Pro704 and Pro708 residues of the mature vWF are underlined.

FIG. 5A shows the results of coomassie blue staining of a molecular weight standard (lane 2); of a supernatant equivalent to 50 μl of the culture transformed with the plasmid pKan707 in YPL medium (lane 1); the plasmid pYG1248 in YPD medium (lane 3) and the plasmid pYG1248 in YPL medium (lane 4).

FIG. 5B shows the results of immunological characterization of the secreted material after using mouse antibodies directed against human vWF. The lanes are the same as described for FIG. 5A except that biotinilated molecular weight standards were used (lane 2).

FIG. 5C shows the results of immunological characterization of the secreted material after using rabbit antibodies directed against human albumin: supernatant equivalent to 50 μl of the culture transformed with the plasmid pKan707 in YPL medium (lane 1), the plasmid pYG1248 in YPD medium (lane 2) the plasmid pYG1248 in YPL medium (lane 3).

In FIG. 6A, coomassie blue staining was employed. Lane 1 is the molecular weight standard, lane 2 is the supernatant equivalent to 2.5 μl of a "Fed Batch" culture in YPD medium after 24 hours of growth; lane 3 is the supernatant of the same culture after 40 hours; and lane 4 is the supernatant of the same culture after 46 hours of growth.

FIG. 6B shows the results of immunological characterization of the secreted material after using mouse antibodies directed against the human vWF. The lanes are the same as in FIG. 6A except that biotinilated molecular weight standards were used.

FIG. 8: Nucleotide sequence (SEQ ID NO:11) and amino acid sequence (SEQ ID NO:12) of the MstII-HindIII restriction fragment of the plasmid pYG1341 (HSA-UK→135). The limit of the EGF-like domain (UK1→146) present in the MstII-HindIII restriction fragment of the plasmid pYG1340 is indicated. The numbering of the amino acids corresponds to the mature chimeric protein SAU-UK1→135 (720 residues).

FIG. 10: Nucleotide sequence (SEQ ID NO:13) and amino acid sequence (SEQ ID NO:14) of the MstII-HindIII restriction fragment of the plasmid pYG1259 (HSA-G.CSF). The limit of the G-CSF part (174 residues) is indicated. The ApaI and SstI (SstI) restriction sites are underlined. The numbering of the amino acids corresponds to the mature chimeric protein HSA-G.CSF (759 residues).

FIGS. 11(*a*) and 11(*b*) together comprise the nucleotide sequence (SEQ ID NO:15) and amino acid sequence (SEQ ID NO:16) of the HindIII restriction fragment of the plasmid pYG1301 (chimera G.CSF-Gly4-HSA). The black arrows indicate the end of the "pre" and "pro" regions of HSA. The ApaI, SstI (SacI) and MstII restriction sites are underlined. The G.CSF (174 residues) and HSA (585 residues) domains are separated by the synthetic linker GGGG. The numbering of the amino acids corresponds to the mature chimeric protein G.CSF-Gly4-SAH (763 residues). The nucleotide sequence between the translation termination codon and the HindIII site comes from the HSA complementary DNA (cDNA) as described in Patent Application EP 361 991.

FIG. 12A shows the results of coomassie blue staining of a molecular weight standard (lane 2); supernatant equivalent to 100 μl of culture transformed with the plasmid pKan707 in YPL medium (lane 1); the plasmid pYG1266 in YPD medium (lane 3) and the plasmid pYG1266 in YPL medium (lane 4).

FIG. 12B shows the results of immunological characterization of the material secreted after using primary antibodies directed against human G-CSF. The lanes are as described above for FIG. 12A.

FIG. 12C shows the results of immunological characterization of the material secreted after using primary antibodies directed against human albumin. The lanes are as described above for FIG. 12A.

FIG. 13A shows the results of coomassie blue staining of a supernatant equivalent to 100 μl of the culture transformed with the plasmid pYG1303 (lane 1), the plasmid pYG1267 (lane 2), and the plasmid pYG1352 (lane 3). Lane 4 is the molecular weight standard.

B, immunological characterization of the material secreted after using primary antibodies directed against the human G-CSF: same legend as in A.

FIG. 14: Nucleotide sequence (SEQ ID NO: 17) and amino acid sequence (SEQ ID NO: 18) of the MstII-HindIII restriction fragment of the plasmid pYG1382 (HSA-Fv'). The VH (124 residues) and VL (107 residues) domains of the Fv' fragment are separated by the synthetic linker (GGGGS)×3. The numbering of the amino acids corresponds to the mature chimeric protein HSA-Fv' (831 residues).

Figures 15A, 15B:
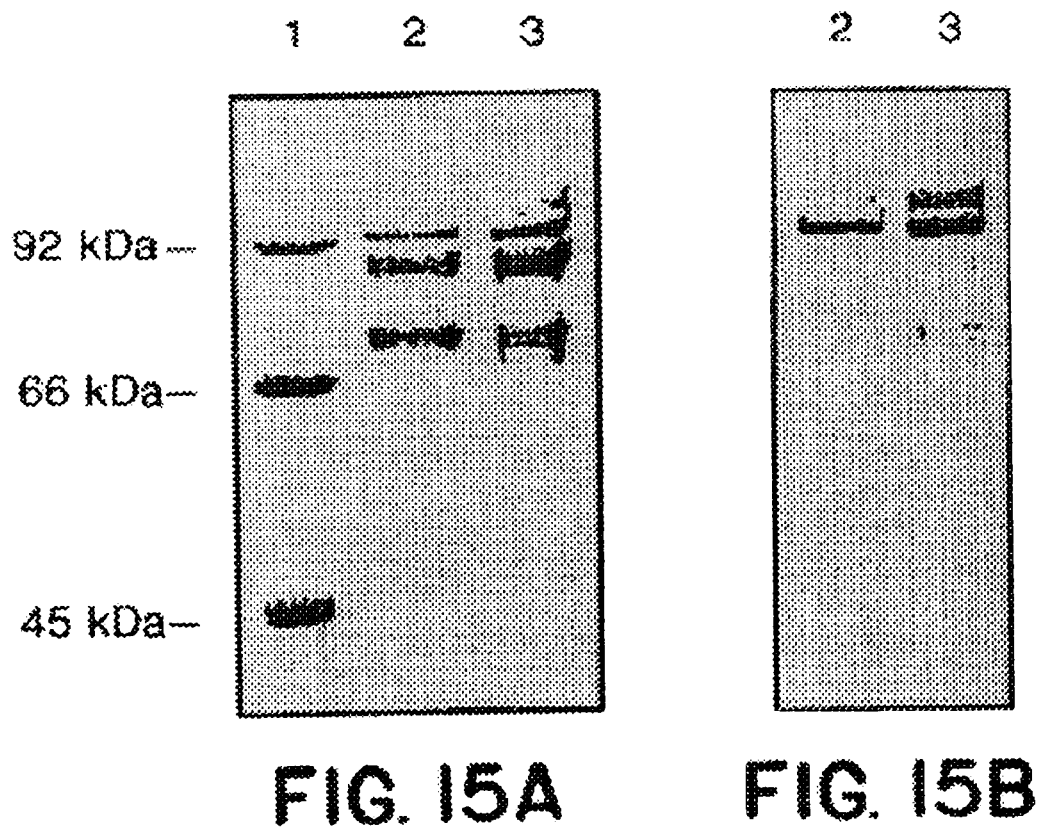

FIGS. 15A and 15B collectively show the characterization of the secretions of the chimera HSA-Fv' by the strain CBS 293.91 transformed with the plasmid pYG1383 (LAC4) after 4 days of growth in erlenmeyers at 28° C. in YPD medium (lane 2), and in YPL medium (lane 3). Lane 1 shows the molecular weight standard. The deposits, equivalent to 200 μl of culture (precipitation with ethanol), are run on a PAGE-SDS gel (8.5%).

FIG. 15A shows the results of coomassie blue staining of the gel.

FIG. 15B shows the results of immunological characterization of the material secreted after using primary antibodies directed against HSA.

Figures 16, 17:
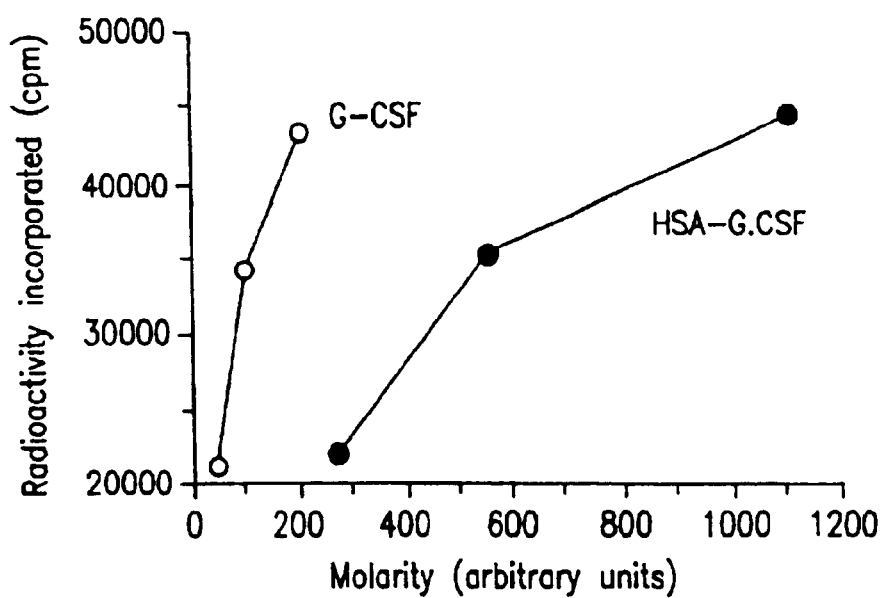

FIG. 16: Assay of the in vitro antagonistic activity of the agglutination of human platelets fixed with formaldehyde: IC50 of the hybrids HSA-vWF694-708, [HSA-vWF470-713 C471G, C474G] and [HSA-vWF470-704 C471G, C474G] compared with the standard RG12986. The determination of the dose-dependent inhibition of the platelet agglutination is carried out according to the method described by C. Prior et al. [Bio/Technology (1992) 10 66] using an aggregameter recording the variations in optical transmission, with stirring, at 37° C. in the presence of human vWF, botrocetin (8.2 mg/ml) of the test product at various dilutions. The concentration of the product which makes it possible to inhibit the control agglutination (in the absence of product) by half is then determined (IC50).

FIG. 17: Activity on the in vitro cellular proliferation of the murine line NFS60. The radioactivity (3 H-thymidine) incorporated into the cellular nuclei after 6 hours of incubation is represented on the y-axis (cpm); the quantity of product indicated on the x-axis is expressed in molarity (arbitrary units).

Figure 18:
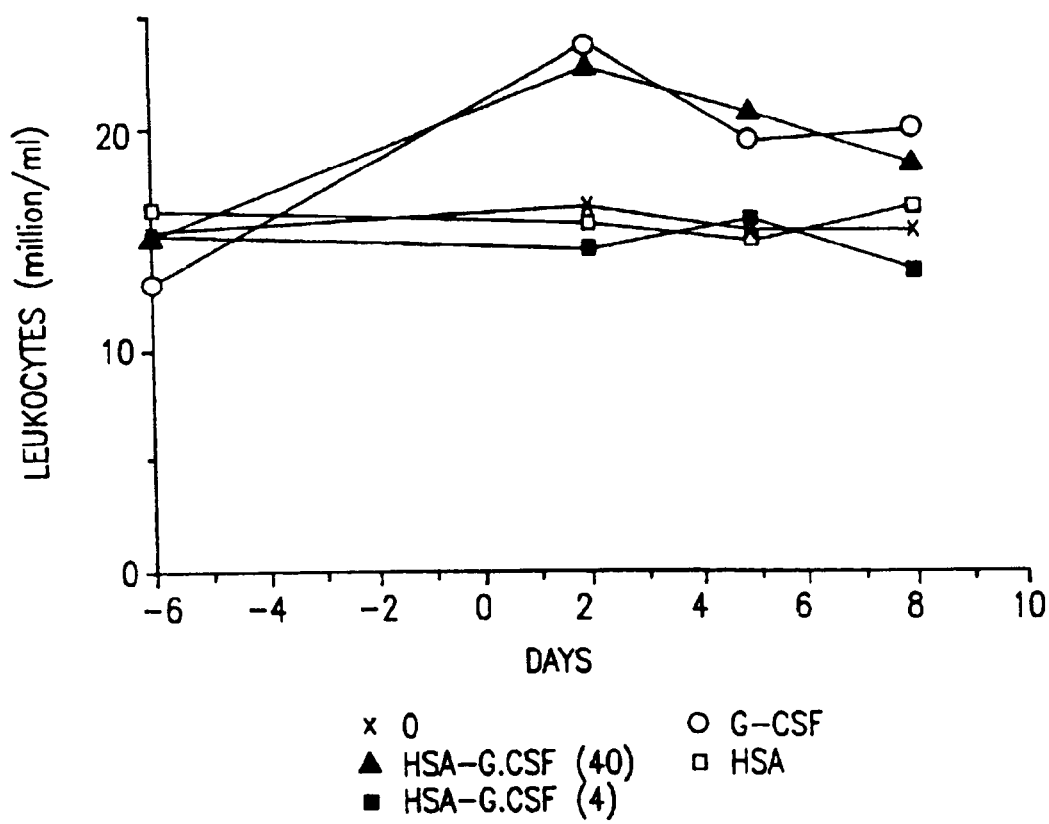

FIG. 18: Activity on granulopoiesis in vivo in rats. The number of neutrophils (average for 7 animals) is indicated on the y-axis as a function of time. The products tested are the chimera HSA-G.CSF (pYG1266), 4 or 40 mg/rat/day), the reference G-CSF (10 mg/rat/day), the recombinant HSA purified from *Kluyveromyces lactis* supernatant (HSA, 30 mg/rat/day, cf. EP 361 991), or physiological saline.

EXAMPLES

GENERAL CLONING TECHNIQUES

The methods conventionally used in molecular biology, such as the preparative extractions of plasmid DNA, the centrifugation of plasmid DNA in caesium chloride gradient, electrophoresis on agarose or acrylamide gels, purification of DNA fragments by electroelution, extractions of proteins with phenol or phenol-chloroform, DNA precipitation in saline medium with ethanol or isopropanol, transformation in *Escherichia coli*, and the like are well known to persons skilled in the art and are widely described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

The restriction enzymes were provided by New England Biolabs (Biolabs), Bethesda Research Laboratories (BRL) or Amersham and are used according to the recommendations of the suppliers.

The pBR322 and pUC type plasmids and the phages of the M13 series are of commercial origin (Bethesda Research Laboratories).

For the ligations, the DNA fragments are separated according to their size by electrophoresis on agarose or acrylamide gels, extracted with phenol or with a phenol/chloroform mixture, precipitated with ethanol and then incubated in the presence of phage T4 DNA ligase (Biolabs) according to the recommendations of the manufacturer.

The filling of the protruding 5' ends is carried out by the Klenow fragment of DNA polymerase I of *E. coli* (Biolabs) according to the specifications of the supplier. The destruction of the protruding 3' ends is carried out in the presence of phage T4 DNA polymerase (Biolabs) used according to the recommendations of the manufacturer. The destruction of the protruding 5' ends is carried out by a controlled treatment with S1 nuclease.

Site-directed mutagenesis in vitro with synthetic oligodeoxynucleotides is carried out according to the method developed by Taylor et al. [Nucleic Acids Res. 13 (1985) 8749–8764] using the kit distributed by Amersham.

The enzymatic amplification of DNA fragments by the so-called PCR technique [Polymerase-catalyzed Chain Reaction, Saiki R. K. et al., Science 230 (1985) 1350–1354; Mullis K. B. and Faloona F. A., Meth. Enzym. 155 (1987) 335–350] is carried out using a "DNA thermal cycler" (Perkin Elmer Cetus) according to the specifications of the manufacturer.

The verification of the nucleotide sequences is carried out by the method developed by Sanger et al. [Proc. Natl. Acad. Sci. U.S.A., 74 (1977) 5463–5467] using the kit distributed by Amersham.

The transformations of *K lactis* with DNA from the plasmids for expression of the proteins of the present invention are carried out by any technique known to persons skilled in the art, and of which an example is given in the text.

Except where otherwise stated, the bacterial strains used are *E. coli* MCI1060 (lacIPOZYA, X74, galU, galK, strAr), or *E. coli* TG1 (lac, proA,B, supE, thi, hsdD5/FtraD36, proA+B+, lacIq, lacZ, M15).

The yeast strains used belong to the budding yeasts and more particularly to yeasts of the genus Kluyveromyces. The *K. lactis* MW98-8C (a, uraA, arg, lys, K+, pKD1°) and *K lactis* CBS 293.91 strain were particularly used; a sample of the MW98-8C strain was deposited on Sep. 16, 1988 at Centraalbureau voor Schimmelkulturen (CBS) at Baarn (the Netherlands) where it was registered under the number CBS 579.88.

A bacterial strain (*E. coli*) transformed with the plasmid pET-8c52K was deposited on Apr. 17, 1990 with the American Type Culture Collection under the number ATCC 68306.

The yeast strains transformed with the expression plasmids encoding the proteins of the present invention are cultured in erlenmeyers or in 21 pilot fermenters (SETRIC, France) at 28° C. in rich medium (YPD: 1% yeast extract, 2% Bactopeptone, 2% glucose; or YPL: 1% yeast extract, 2% Bactopeptone, 2% lactose) with constant stirring.

EXAMPLE 1

COUPLING AT THE C-TERMINUS OF HSA

The plasmid pYG404 is described in Patent Application EP 361 991. This plasmid contains a HindIII restriction fragment encoding the prepro-HSA gene preceded by the 21 nucleotides naturally present immediately upstream of the initiator ATG for translation of the PGK gene of *S. cerevisiae*. The nucleotide sequence of this restriction fragment is included in that of FIG. 2. The MstII site localized in the coding sequence, three residues from the codon specifying the end of translation is particularly useful as site for cloning a biologically active peptide which it is desired to couple in translational phase at the C-terminus of HSA. In a specific embodiment, it is useful to use peptides whose sequence is encoded by an MstII-HindIII restriction fragment of the type: 5'-CCTTAGGCTTA [3×N]p TAAGCTT-3' (SEQ ID NO:20), the sequence encoding the biologically active peptide (p residues) is [3×N]p). The ligation of this fragment to the HindIII-MstII restriction fragment corresponding to the entire gene encoding HSA, with the exception of the three C-terminalmost amino acids (leucin-glycine-leucin residues) generates a HindIII restriction fragment containing a hybrid gene encoding a chimeric protein of the HSA-PEPTIDE type (FIG. 1, panel A), immediately preceded by the "prepro" export region of HSA. In another embodiment, the biologically active peptide may be present more than once in the chimera.

EXAMPLE 2

COUPLING AT THE N-TERMINUS OF HSA

Figure 1A:
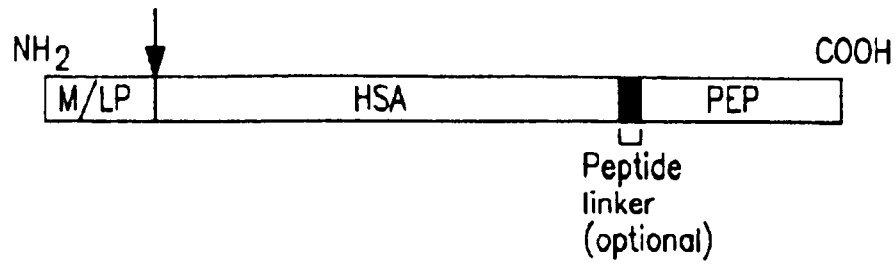
FIG. 1A is a schematic representation of the chimera of the HSA-PEPTIDE type.
Figure 1B:
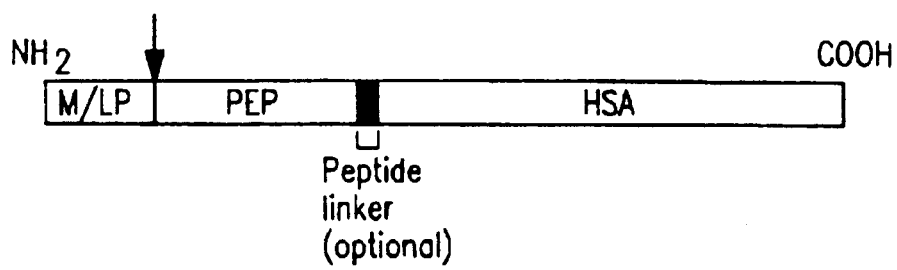
FIG. 1B is a schematic representation of a chimera of the PEPTIDE-HSA type.
Figure 1C:
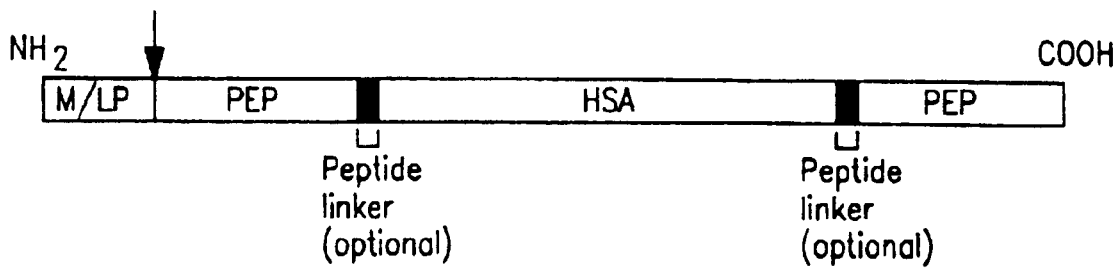
FIG. 1C is a schematic representation of a chimera of the PEPTIDE-HSA-PEPTIDE type. Abbreviations used: M/LP, translational initiator methionine residue, optionally followed by a signal sequence for secretion; HSA, mature albumin or one of its molecular variants; PEP, peptide of natural or artificial origin possessing a given therapeutic property. The PEP sequence may be present several times in the FIG. 1A, B or C molecules. The black arrow indicates the N-terminal end of the mature protein.

In a specific embodiment, the combined techniques of site-directed mutagenesis and PCR amplification make it possible to construct hybrid genes encoding a chimeric protein resulting from the translational coupling between a signal peptide (and for example the prepro region of HSA), a sequence including the biologically active peptide and the mature form of HSA or one of its molecular variants. These hybrid genes are preferably bordered in 5' of the translational initiator ATG and in 3' of the translational stop codon by HindIII restriction sites and encode chimeric proteins of the PEPTIDE-HSA type (FIG. 1, panel B). In a still more specific embodiment, the biologically active peptide may be present more than once in the chimera.

EXAMPLE 3

COUPLING AT THE N- AND C-TERMINUS OF HSA

The combined techniques of site-directed mutagenesis and PCR amplification described in Examples 1 and 2 make it possible to construct hybrid genes encoding a chimeric protein resulting from the translational coupling between the mature form of HSA, or one of its molecular variants, and a biologically active peptide coupled to the N- and C-terminal ends of HSA. These hybrid genes are preferably bordered in 5' of the translational initiator ATG and in 3' of the translational stop codon by HindIII restriction sites and encode chimeric proteins of the PEPTIDE-HSA-PEPTIDE type (FIG. 1, panel C), immediately preceded by the "prepro" export region of HSA. In a still more specific embodiment, the biologically active peptide may be present more than once in the chimera.

EXAMPLE 4

EXPRESSION PLASMIDS

Figure 3:
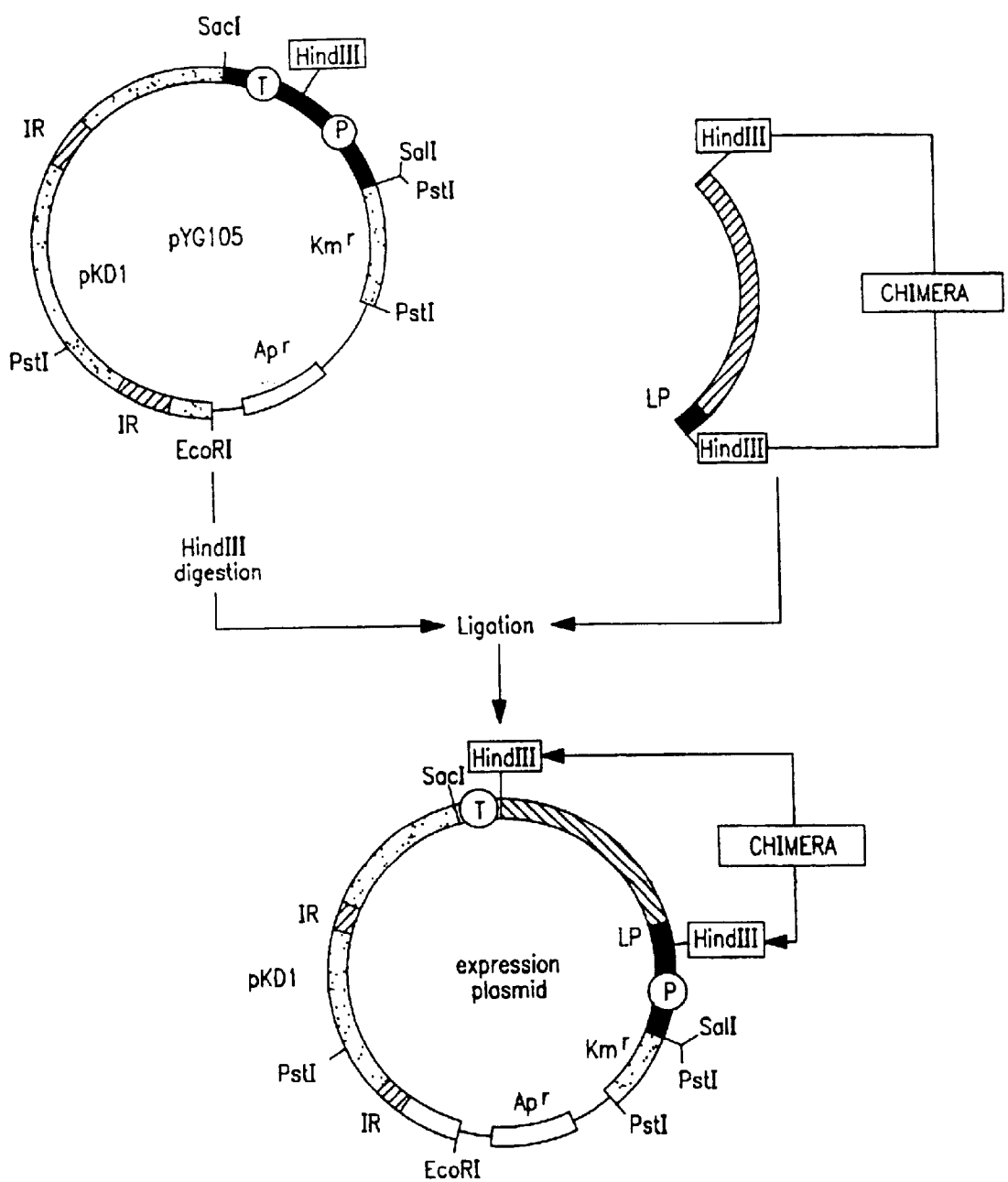
FIG. 3: Restriction map for the plasmid pYG105 and generic strategy for construction of the plasmids for expression of the chimeric proteins of the present invention. Abbreviations used: P, transcriptional promoter; T, transcriptional terminator; IR, inverted repeat sequences of the plasmid pKD 1; LP, signal sequence for secretion; Apr and Kmr designate the genes for resistance to ampicillin (*E. coli*) and to G418 (yeasts), respectively.

The chimeric proteins of the preceding examples can be expressed in yeasts using functional, regulatable or constitutive promoters such as, for example, those present in the plasmids pYG105 (LAC4 promoter of *Kluyveromyces lactis*), pYG106 (PGK promoter of *Saccharomyces cerevisiae*), pYG536 (PHO5 promoter of *S. cerevisiae*), or hybrid promoters such as those described in Patent Application EP 361 991. The plasmids pYG105 and pYG106 are particularly useful here because they permit the expression of the genes encoded by the HindIII restriction fragments as described in the preceding examples and cloned into the HindIII site and in the productive orientation (defined as the orientation which places the "prepro" region of albumin proximally relative to the promoter for transcription), using promoters which are functional in *K. lactis*, regulatable (pYG105) or constitutive (pYG106). The plasmid pYG105 corresponds to the plasmid pKan707 described in Patent Application EP 361 991 in which the HindIII restriction site which is unique and localized in the gene for resistance to geneticin (G418) has been destroyed by site-directed mutagenesis while preserving an unchanged protein (oligodeoxynucleotide 5'-GAAATGCATAAGCTCTTGCCATTCTCACCG-3') (SEQ ID NO:21). The SalI-SacI fragment encoding the URA3 gene of the mutated plasmid was then replaced with a SalI-SacI restriction fragment containing an expression cassette consisting of the LAC4 promoter of *K. lactis* (in the form of a SalI-HindIII fragment) and the terminator of the PGK gene of *S. cerevisiae* (in the form of a HindIII-SacI fragment). The plasmid pYG105 is mitotically very stable in the Kluyveromyces yeasts and a restriction map thereof is given in FIG. 3. The plasmids pYG105 and pYG106 differ from each other only in the nature of the promoter for transcription encoded by the SalI-HindIII fragment.

EXAMPLE 5

TRANSFORMATION OF THE YEASTS

The transformation of the yeasts belonging to the genus Kluyveromyces, and in particular the strains MW98-8C and CBS 293.91 of *K. lactis* is carried out for example by the technique for treating whole cells with lithium acetate [Ito H. et al., J. Bacteriol. 153 (1983) 163–168], adapted as follows. The growth of the cells is carried out at 28° C. in 50 ml of YPD medium, with stirring and up to an optical density of 600 nm (OD600) of between 0.6 and 0.8; the cells are harvested by centrifugation at low speed, washed in a sterile solution of TE (10 mM Tris HCl pH 7.4; 1 mM EDTA), resuspended in 3–4 ml of lithium acetate (0.1 M in TE) in order to obtain a cellular density of about $2 \times 10^8$ cells/ml, and then incubated at 30° C. for 1 hour with moderate stirring. Aliquots of 0.1 ml of the resulting suspension of competent cells are incubated at 30° C for 1 hour in the presence of DNA and at a final concentration of 35% polyethylene glycol (PEG4000, Sigma). After a heat shock of 5 minutes at 42° C., the cells are washed twice, resuspended in 0.2 ml of sterile water and incubated for 16 hours at 28° C. in 2 ml of YPD medium in order to permit the phenotypic expression of the gene for resistance to G418 expressed under the control of the Pk1 promoter (cf. EP 361 991); 200 μl of the cellular suspension are then plated on selective YPD dishes (G418, 200 μg/ml). The dishes are incubated at 28° C. and the transformants appear after 2 to 3 days of cell growth.

EXAMPLE 6

SECRETION OF THE CHIMERAS

After selection on rich medium supplemented with G418, the recombinant clones are tested for their capacity to secrete the mature form of the chimeric proteins. Few clones, corresponding to the strain CBS 293.91 or MW98-8C transformed by the plasmids for expression of the chimeras between HSA and the biologically active part, are incubated in YPD or YPL medium at 28° C. The cellular supernatants are recovered by centrifugation when the cells reach the stationary growth phase, optionally concentrated 10 times by precipitation for 30 minutes at −20° C. in a final concentration of 60% ethanol, and then tested after electrophoresis on an 8.5% SDS-PAGE gel, either directly by staining the gel with coomassie blue, or after immunoblotting using primary antibodies directed against the biologically active part or a rabbit polyclonal serum directed against HSA. During the experiments for immunological detection, the nitrocellulose filter is first incubated in the presence of specific primary antibodies, washed several times, incubated in the presence of goat antibodies directed against the primary antibodies, and then incubated in the presence of an avidin-peroxidase complex using the "ABC kit" distributed by Vectastain (Biosys S. A., Compiegne, France). The immunological reaction is then revealed by the addition of 3,3'-diamino benzidine tetrahydrochloride (Prolabo) in the presence of hydrogen peroxide, according to the recommendations of the manufacturer.

EXAMPLE 7

CHIMERAS DERIVED FROM THE VON WILLEBRAND FACTOR

E.7.1. Fragments Antagonizing the Binding of vWF to the Platelets

E.7.1.1. Thr470-Val713 Residues of vWF

The plasmid pET-8c52K contains a fragment of the vWF cDNA encoding residues 445 to 733 of human vWF and therefore includes several crucial determinants of the interaction between vWF and the platelets on the one hand, and certain elements of the basal membrane and the subendothelial tissue on the other, and especially the peptides G10 and D5 which antagonize the interaction between vWF and GP1b [Mori H. et al., J. Biol. Chem. 263 (1988) 17901–17904]. This peptide sequence is identical to the corresponding sequence described by Titani et al. [Biochemistry 25, (1986) 3171–3184]. The amplification of these genetic determinants can be carried out using the plasmid pET-8c52K, for example by the PCR amplification technique, using as primer oligodeoxynucleotides encoding contiguous residues localized on either side of the sequence to be amplified. The amplified fragments are then cloned into vectors of the M13 type for their verification by sequencing using either the universal primers situated on either side of the multiple cloning site, or oligodeoxynucleotides specific for the amplified region of the vWF gene of which the sequence of several isomorphs is known [Sadler J. E. et al., Proc. Natl. Acad. Sci. 82 (1985) 6394–6398; Verweij C. L. et al., EMBO J. 5 (1986) 1839–1847; Shelton-Inloes B. B. et al., Biochemistry 25 (1986) 3164–3171; Bonthron D. et al., Nucleic Acids Res. 17 (1986) 7125–7127]. Thus, the PCR amplification of the plasmid pET-8c52K with the oligodeoxynucleotides 5'-CCCGGGATCCCTTAGGCTTAACCTGTGAAGCCTGC-3' (SEQ ID NO:22) (Sq1969, the MstII site is underlined) and 5'-CCCGGGATCCAAGCTTAGACTTGTGCCATGTCG-3' (SEQ ID NO:23) (Sq2029, the HindIII site is underlined) generates an MstII-HindIII restriction fragment including the Thr470 to Val713 residues of vWF (FIG. 4, panel E). The ligation of this fragment to the HindIII-MstII restriction fragment corresponding to the entire gene encoding HSA, with the exception of the three C-terminalmost amino acids (cf. FIG. 2) generates a HindIII restriction fragment containing a hybrid gene encoding a chimeric protein of the HSA-PEPTIDE type (FIG. 1, panel A), immediately preceded by the "prepro" export region of HSA. This restriction fragment is cloned in the productive orientation and into the HindIII site of the plasmid pYG105, which generates the expression plasmid pYG1248 (HSA-vWF470-713).

E.7.1.2. Molecular Variants:

In another embodiment, the binding site of vWF is a peptide including the Thr470 to Asp498 residues of the mature vWF. This sequence including the peptide G10 (Cys474-Pro488) described by Mori et al. [J. Biol. Chem. 263 (1988) 17901–17904] and capable of antagonizing the interaction of human vWF with the GP1b of the human platelets. The sequence corresponding to the peptide G10 is first included in an MstII-HindIII restriction fragment (FIG. 4, panel B), for example by PCR amplification of the plasmid pET-8c52K with the oligodeoxynucleotides Sq1969 and 5'-CCCGGGATCCAAGCTTAGTCCTCCACATACAG-3' (SEQ ID NO:24) (Sq1970, the HindIII site is underlined), which generates an MstII-HindIII restriction fragment including the peptide G10, and whose sequence is: 5'-CCTTAGGCTTAACCTGTGAAGCCTGCCAGGAG CCGGGAGGCCTGGTGGTGCCTCCCA CAGATGCCCCGGTGAGCCCC-ACCACTCTGTATGTGGAGGACTAAGCTT-3' (SEQ ID NO:25) (the sequence encoding the peptide G10 is in bold characters). The ligation of this fragment to the HindIII-MstII restriction fragment corresponding to the entire gene encoding HSA, with the exception of the three C-terminalmost amino acids (cf. FIG. 2) generates a HindIII restriction fragment containing a hybrid gene encoding a chimeric protein of the HSA-PEPTIDE type (FIG. 1, panel A), immediately preceded by the "prepro" export region of HSA. This restriction fragment is cloned in the productive orientation into the HindIII site of the plasmid pYG105, which generates the expression plasmid pYG1214.

In another embodiment, the site for binding of vWF to GP1b is directly designed with the aid of synthetic oligodeoxynucleotides, and for example the oligodeoxynucleotides 5'-TTAGGCCTCTGTGACCTTGCCCCTGAAGCCCCT CCTCCTACTCTGCCCCCCTAAGCTT A-3' (SEQ ID NO:26) and 5'-GATCTAAGCTTAGGGGGGCAGAGTAGGAGGA GGGGCTTCAGGGGCAAGGTCACAG AGGCC-3' (SEQ ID NO:27). These oligodeoxynucleotides form, by pairing, a MstII-BglII restriction fragment including the MstII-HindIII fragment (FIG. 4, panel C) corresponding to the peptide D5 defined by the Leu694 to Pro708 residues of vWF. The ligation of the MstII-HindIII fragment to the HindIII-MstII restriction fragment corresponding to the entire gene encoding HSA with the exception of the three C-terminalmost amino acids (cf. FIG. 2) generates a HindIII restriction fragment containing a hybrid gene encoding a chimeric protein of the HSA-PEPTIDE type (FIG. 1, panel A), immediately preceded by the "prepro" export region of HSA. This restriction fragment is cloned in the productive orientation into the HindIII site of the plasmid pYG105, which generates the expression plasmid pYG1206.

Useful variants of the plasmid pET-8c52K are deleted by site-directed mutagenesis between the peptides G10 and G5, for example sites for binding to collagen, and/or to heparin, and/or to botrocetin, and/or to sulphatides and/or to ristocetin. One example is the plasmid pMMB9 deleted by site-directed mutagenesis between the residues Cys509 and Ile662. The PCR amplification of this plasmid with the oligodeoxynucleotides Sq1969 and Sq2029 generates an MstII-HindIII restriction fragment (FIG. 4, panel D) including the Thr470 to Tyr508 and Arg663 to Val713 residues and in particular the peptides G 10 and D5 of vWF and deleted in particular of its site for binding to collagen localized between the residues Glu542 and Met622 [Roth G. J. et al., Biochemistry 25 (1986) 8357–8361]. The ligation of this fragment to the HindIII-MstII restriction fragment corresponding to the entire gene encoding HSA, with the exception of the three C-terminalmost amino acids (cf. FIG. 2) generates a HindIII restriction fragment containing a hybrid gene encoding a chimeric protein of the HSA-PEPTIDE type (FIG. 1, panel A), immediately preceded by the "prepro" export region of HSA. This restriction fragment is cloned in the productive orientation into the HindIII site of the plasmid pYG105, which generates the expression plasmid pYG1223.

In other embodiments, the use of combined techniques of site-directed mutagenesis and PCR amplification makes it possible to generate at will variants of the MstII-HindIII restriction fragment of panel A of FIG. 4 but deleted of one or more sites for binding to sulphatides and/or to botrocetin and/or to heparin and/or to collagen, and/or substituted by any residue involved in the vWF-associated emergence of IIB type pathologies.

In other useful variants of the plasmid pET-8c52K, mutations are introduced, for example by site-directed mutagenesis, in order to replace or suppress all or part of the set of cysteines present at positions 471, 474, 509 and 695 of the human vWF. Specific examples are the plasmids p5E and p7E in which the cysteins present at positions 471 and 474, on the one hand, and at positions 471, 474, 509 and 695, on the other hand, have been respectively replaced by glycine residues. The PCR amplification of these plasmids with the oligodeoxynucleotides Sq2149 (5'-CCCGGGATCCCTTAGGCTTAACCGGTGAAGCCG GC-3' (SEQ ID NO:28), the MstII site is underlined) and Sq2029 makes it possible to generate MstII-HindIII restriction fragments including the Thr470 to Val713 residues of the natural vWF with the exception that at least the cystein residues at positions 471 and 474 were mutated to glycine residues. The ligation of these fragments to the HindIII-MstII restriction fragment corresponding to the entire gene encoding HSA with the exception of the three C-terminalmost amino acids (cf. FIG. 2) generates a HindIII restriction fragment containing a hybrid gene encoding a chimeric protein of the HSA-PEPTIDE type (FIG. 1, panel A), immediately preceded by the "prepro" export region of HSA. These restriction fragments are cloned in the productive orientation into the HindIII site of the plasmid pYG105, which generates the expression plasmids pYG1283 (chimera HSA-vWF470-713, C471G, C474G) and pYG1279 (chimera HSA-vWF470-713, C471G, C474G, C509G, C695G).

Other particularly useful mutations affect at least one residue involved in vWF-associated type IIB pathologies (increase in the intrinsic affinity of vWF for GP1b), such as the residues Arg543, Arg545, Trp550, Val551, Val553, Pro574 or Arg578 for example. The genetic recombination techniques in vitro also make it possible to introduce at will one or more additional residues into the sequence of vWF and for example a supernumerary methionine between positions Asp539 and Glu542.

E.7.2. Fragments Antagonizing the Binding of vWF to the Sub-Endothelium

In a specific embodiment, the sites for binding of vWF to the components of the sub-endothelial tissue, and for example collagen, are generated by PCR amplification of the plasmid pET-8c52K, for example with the oligodeoxynucleotides Sq2258 (5'-GGATCCTTAGGGCTGTGCAGCAGGCTACTGGAC CTGGTC-3' (SEQ ID NO:29), the MstII site is underlined) and Sq2259 (5'-GAATTCAAGCTTAACAGAGGTAGCTAA-CGATCTCGTCCC-3' (SEQ ID NO:30), the HindIII site is underlined), which generates an MstII-HindIII restriction fragment encoding the Cys509 to Cys695 residues of the natural vWF. Deletion molecular variants or modified variants are also generated which contain any desired combination between the sites for binding of vWF to the sulphatides and/or to botrocetin and/or to heparin and/or to collagen and/or any residue responsible for a modification of the affinity of vWF for GP1b (vWF-associated type II pathologies). In another embodiment, the domain capable of binding to collagen may also come from the vWF fragment which is between the residues 911 and 1114 and described by Pareti et al. [J. Biol. Chem. (1987)262: 13835–13841]. The ligation of these fragments to the HindIII-MstII restriction fragment corresponding to the entire gene encoding HSA with the exception of the three C-terminalmost amino acids (cf. FIG. 2) generates HindIII restriction fragments containing a hybrid gene encoding a chimeric protein of the HSA-PEPTIDE type (FIG. 1, panel A), immediately preceded by the "prepro" export region of HSA. These restriction fragments are cloned in the productive orientation into the HindIII site of the plasmid pYG105, which generates the corresponding expression plasmids, and for example the plasmid pYG1277 (HSA-vWF509-695).

Figure 5A:
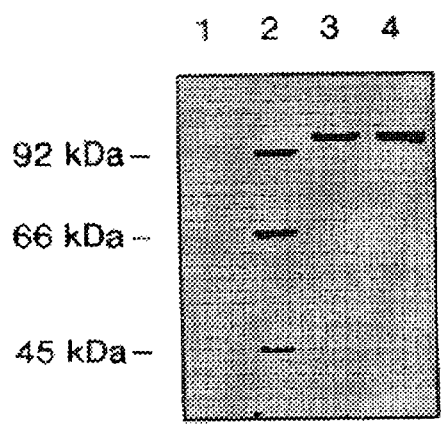
FIGS. 5A, 5B, and 5C collectively show the characterization of the material secreted after 4 days of culture (erlenmeyers) of the strain CBS 293.91 transformed with the plasmids pYG1248 (plasmid for expression of a chimera of the HSA-vWF Thr470→Val713) and pKan707 (control plasmid). In this experiment, the polypeptides for FIGS. 5A, 5B, and 5C were run on the same gel (8.5% SDS-PAGE) and then treated separately.
Figure 5B:
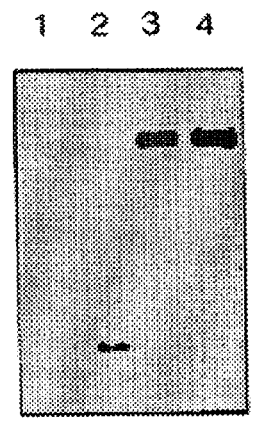
Figure 5C:
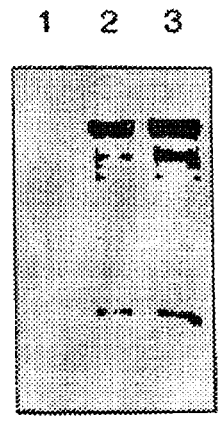

E.7.3. Purification and Molecular Characterization of the Chimeras Between HSA and vWF The chimeras present in the culture supernatants corresponding to the CBS 293.91 strain transformed, for example with the expression plasmids according to Examples E.7.1. and E.7.2., are characterized in a first instance by means of antibodies specific for the HSA part and for the vWF part. The results of FIGS. 5 to 7 demonstrate that the yeast *K. lactis* is capable of secreting chimeric proteins between HSA and a fragment of vWF, and that these chimeras are immunologically reactive. It may also be desirable to purify some of these chimeras. The culture is then centrifuged (10,000 g, 30 min), the supernatant is passed through a 0.22 mm filter (Millipore) and then concentrated by ultrafiltration (Amicon) using a membrane whose discrimination threshold is situated at 30 kDa. The concentrate obtained is then dialysed against a Tris-HCl solution (50 mM pH 8) and then purified on a column. For example, the concentrate corresponding to the culture supernatant of the CBS 293.91 strain transformed with the plasmid pYG1206 is purified by affinity chromatography on Blue-Trisacryl (IBF). A purification by ion-exchange chromatography can also be used. For example, in the case of the chimera HSA-vWF470-713, the concentrate obtained after ultrafiltration is dialysed against a Tris-HCl solution (50 mM pH 8), and then loaded in 20 ml fractions onto a cation-exchange column (5 ml) (S Fast Flow, Pharmacia) equilibrated in the same buffer. The column is then washed several times with the Tris-HCl solution (50 mM pH 8) and the chimeric protein is then eluted from the column by an NaCl gradient (0 to 1M). The fractions containing the chimeric protein are then pooled and dialysed against a 50 mM Tris-HCl solution (pH 8) and then reloaded onto the S Fast Flow column. After elution of the column, the fractions containing the protein are pooled, dialysed against water and freeze-dried before characterization: for example, sequencing (Applied Biosystem) of the protein [HSA-vWF470-704 C471G, C474G] secreted by the yeast CBS 293.91 gives the N-terminal sequence expected for HSA (Asp-Ala-His . . . ), demonstrating a correct maturation of the chimera immediately at the C-terminus of the doublet of residues Arg—Arg of the "pro" region of HSA (FIG. 2). The essentially monomeric character of the chimeric proteins between HSA and vWF is also confirmed by their elution profile on a TSK 3000 column [Toyo Soda Company, equilibrated with a cacodylate solution (pH 7) containing 0.2M Na2 S04 ]: for example the chimera [HSA-VWF 470-704 C471 G, C474G] behaves under the conditions like a protein with an apparent molecular weight of 95 kDa, demonstrating its monomeric character.

EXAMPLE 8

CHIMERAS DERIVED FROM UROKINASE

E.8.1. Constructs

A fragment corresponding to the amino-terminal fragment of urokinase (ATF: EGF-like domain+ringle domain) can be obtained from the corresponding messenger RNA of cells of certain human carcinoma, for example using the RT-PCR kit distributed by Pharmacia. An MstII-HindIII restriction fragment including the ATF of human urokinase is given in FIG. 8. The ligation of the HindIII-MstII fragment of the plasmid pYG404 to this MstII-HindIII fragment makes it possible to generate the HindIII fragment of the plasmid pYG1341 which encodes a chimeric protein in which the HSA molecule is genetically coupled to the ATF (HSA-UK1→135). Likewise, the plasmid pYG1340 contains a HindIII fragment encoding a chimera composed of HSA immediately followed by the first 46 residues of human urokinase (HSA-UK1→146, cf. FIG. 8). The cloning in the productive orientation, of the HindIII restriction fragment of the plasmid pYG1340 (HSA-UK1→46) into the HindIII site of the plasmids pYG105 (LAC4) and pYG106 (PGK) generates the expression plasmids pYG1343 and pYG1342 respectively. Likewise, the cloning, in the productive orientation, of the HindIII restriction fragment of the plasmid pYG1341 (HSA-UK1→135) into the HindIII site of the plasmids pYG105 (LAC4) and pYG106 (PGK) generates the expression plasmids pYG1345 and pYG 1344 respectively.

E.8.2. Secretion of the Hybrids

Figure 9:
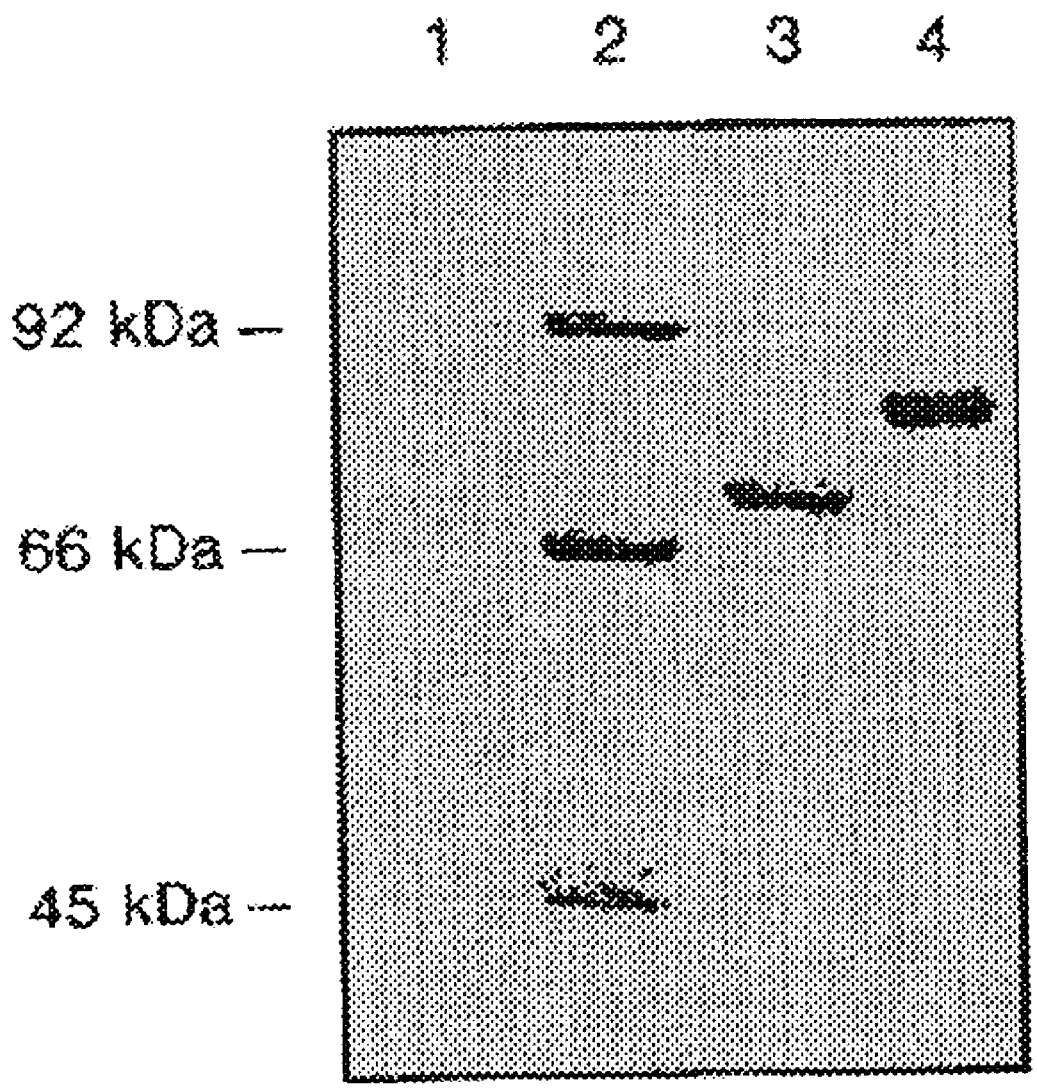
FIG. 9: Secretion of the HSA-UK1-46 and HSA-UK1-135 chimeras by the strain CBS 293.91 respectively transformed with the plasmids pYG1343 (HSA-UK1-46) and pYG1345 (HSA-UK1-135), after 4 days of growth (YPL+ G418 medium). The deposits (equivalent to 50 μl of culture) are run on an 8.5% PAGE-SDS gel and stained with coomassie blue: supernatant from a clone transformed with the plasmids pKan707 (lane 1), pYG1343 (lane 3) or pYG1345 (lane 4); molecular weight standard (lane 2).

After selection on rich medium supplemented with G418, the recombinant clones are tested for their capacity to secrete the mature form of the chimeric proteins HSA-UK. A few clones corresponding to the strain K. lactis CBS 293.91, which is transformed with the expression plasmids according to Example E.9.1., are incubated in selective complete liquid medium at 28° C. The cellular supernatants are then tested after electrophoresis on an 8.5% acrylamide gel, either directly by staining of the gel with coomassie blue, or after immunoblotting using as primary antibodies a rabbit polyclonal serum directed against human albumin or against human urokinase. The results of FIG. 9 demonstrate that the hybrid proteins HSA-UK1→46 and HSA-UK1→135 are particularly well secreted by the yeast Kluyveromyces.

E.8.3 Purification of the Chimeras Between HSA and Urokinase

After centrifugation of a culture of the CBS 293.91 strain transformed with the expression plasmids according to Example E.8.1., the culture supernatant is passed through a 0.22 mm filter (Millipore) and then concentrated by ultrafiltration (Amicon) using a membrane whose discrimination threshold is situated at 30 kDa. The concentrate obtained is then adjusted to 50 mM Tris-HCl starting with a stock solution of IM Tris-HCl (pH 7), and then loaded in 20 ml fractions onto an anion-exchange column (3 ml) (D-Zephyr, Sepracor) equilibrated in the same buffer. The chimeric protein (HSA-UK1→46 or HSA-UK1→135) is then eluted from the column by a gradient (0 to IM) of NaCl. The fractions containing the chimeric protein are then pooled and dialysed against a 50 mM Tris-HCl solution (pH 6) and reloaded onto a D-Zephyr column equilibrated in the same buffer. After elution of the column, the fractions containing the protein are pooled, dialysed against water and freeze-dried before characterization of their biological activity and especially with respect to their ability to displace urokinase from its cellular receptor.

EXAMPLE 9

CHIMERAS DERIVED FROM G-CSF

E.9.1. Constructs

E.9.1.1. Coupling at the C-terminus of HSA.

An MstII-HindIII restriction fragment including the mature form of human G-CSF is generated, for example according to the following strategy: a KpnI-HindIII restriction fragment is first obtained by the enzymatic PCR amplification technique using the oligodeoxynucleotides Sq2291 (5'-CAAGGATCC-AAGCTTCAGGGCTGCGCAAGGTGGCGTAG-3' (SEQ ID NO:31), the HindIII site is underlined) and Sq2292 (5'-CGGGGTACCTTAGGCTTAACCCCCCTG-GGCCCTGCCAGC-3' (SEQ ID NO:32), the KpnI site is underlined) as primer on the plasmid BBG13 serving as template. The plasmid BBG13 contains the gene encoding the B form (174 amino acids) of mature human G-CSF, which is obtained from British Bio-technology Limited, Oxford, England. The enzymatic amplification product of about 550 nucleotides is then digested with the restriction enzymes KpnI and HindIII and cloned into the vector pUC19 cut with the same enzymes, which generates the recombinant plasmid pYG1255. This plasmid is the source of an MstII-HindIII restriction fragment which makes it possible to fuse G-CSF immediately downstream of HSA (chimera HSA-G.CSF) and whose nucleotide sequence is given in FIG. 10.

It may also be desirable to insert a peptide linker between the HSA part and G-CSF, for example in order to permit a better functional presentation of the transducing part. An MstII-HindIII restriction fragment is for example generated by substitution of the MstII-ApaI fragment of the plasmid pYG1255 by the oligodeoxynucleotides Sq2742 (5'-TTAGGCTTAGGTGGTGGCGGT-ACCCCCCTGGGCC-3' (SEQ ID NO:33), the codons encoding the glycine residues of this particular linker are underlined) and Sq2741 (5'-CAGGGGGGTACCGCCACCACCTAAGCC-3') (SEQ ID NO:34) which form, by pairing, an MstII-ApaI fragment. The plasmid thus generated therefore contains an MstII-HindIII restriction fragment whose sequence is identical to that of FIG. 10 with the exception of the MstII-ApaI fragment.

The ligation of the HindIII-MstII fragment of the plasmid pYG404 to the MstII-HindIII fragment of the plasmid pYG1255 makes it possible to generate the HindIII fragment of the plasmid pYG1259 which encodes a chimeric protein in which the B form of the mature G-CSF is positioned by genetic coupling in translational phase at the C-terminus of the HSA molecule (HSA-G.CSF).

An identical HindIII restriction fragment, with the exception of the MstII-ApaI fragment, may also be easily generated and which encodes a chimeric protein in which the B form of the mature G-CSF is positioned by genetic coupling in translational phase at the C-terminus of the HSA molecule and a specific peptide linker. For example, this linker consists of 4 glycine residues in the HindIII fragment of the plasmid pYG1336 (chimera HSA-Gly4-G.CSF).

The HindIII restriction fragment of the plasmid pYG1259 is cloned in the productive orientation and into the HindIII restriction site of the expression plasmid pYG105, which generates the expression plasmid pYG1266 (HSA-G.CSF). In another exemplification, the cloning of the HindIII restriction fragment of the plasmid pYG1259 in the productive orientation and into the HindIII site of the plasmid pYG106 generates the plasmid pYG1267. The plasmids pYG1266 and pYG1267 are mutually isogenic with the exception of the SalI-HindIII restriction fragment encoding the LAC4 promoter of K lactis (plasmid pYG1266) or the PGK promoter of S. cerevisiae (plasmid pYG1267).

In another exemplification, the cloning in the productive orientation of the HindIII restriction fragment of the plasmid pYG1336 (chimera HSA-Gly4-G.CSF) into the HindIII site of the plasmids pYG105 (LAC4) and pYG106 (PGK) generates the expression plasmids pYG 1351 and pYG 1352 respectively.

E.9.1.2. Coupling at the N-terminus of HSA

In a specific embodiment, the combined techniques of site-directed mutagenesis and PCR amplification make it possible to construct hybrid genes encoding a chimeric protein resulting from the translational coupling between a signal peptide (and for example the prepro region of HSA), a sequence including a gene having a G-CSF activity, and the mature form of HSA or one of its molecular variants (cf. chimera of panel B, FIG. 1). These hybrid genes are preferably bordered in 5' of the translational initiator ATG and in 3' of the translational stop codon by HindIII restriction sites. For example the oligodeoxynucleotide Sq2369 (5'-GTTCTACGCCACCTTGCGCAGCCCGGTG-GAGGCGGTGATGCACACAAGAGTGAGGT TGCTCATCGG-3' (SEQ ID NO:35) the residues underlined (optional) correspond in this particular chimera to a peptide linker composed of 4 glycine residues) makes it possible, by site-directed mutagenesis, to put in translational phase the mature form of the human G-CSF of the plasmid BBG13 immediately upstream of the mature form of HSA, which generates the intermediate plasmid A. Likewise, the use of the oligodeoxynucleotide Sq2338[5'-CAGGGAGCTGGCAGGGCCCAGGGGGGT-TCGACGAAACACACCCCTGGAATAAGCC GAGCT-3' (SEQ ID NO:36) (non-coding strand), the nucleotides complementary to the nucleotides encoding the first N-terminal residues of the mature form of the human G-CSF are underlined] makes it possible, by site-directed mutagenesis, to couple in translational reading phase the prepro region of HSA immediately upstream of the mature form of the human G-CSF, which generates the intermediate plasmid B. A HindIII fragment encoding a chimeric protein of the PEPTIDE-HSA type (cf. FIG. 1, panel B) is then generated by combining the HindIII-SstI fragment of the plasmid B (joining prepro region of HSA+N-terminal fragment of the mature G-CSF) with the SstI-HindIII fragment of the plasmid A [joining mature G-CSF-(glycine)x4-mature HSA]. The plasmid pYG1301 contains this specific HindIII restriction fragment encoding the chimera G.CSF-Gly4-HSA fused immediately downstream of the prepro region of HSA (FIG. 11). The cloning of this HindIII restriction fragment in the productive orientation and into the HindIII site of the plasmids pYG105 (LAC4) and pYG106 (PGK) generates the expression plasmids pYG1302 and pYG1303 respectively.

E.9.2. Secretion of the Hybrids.

Figures 12A, 12B, 12C:
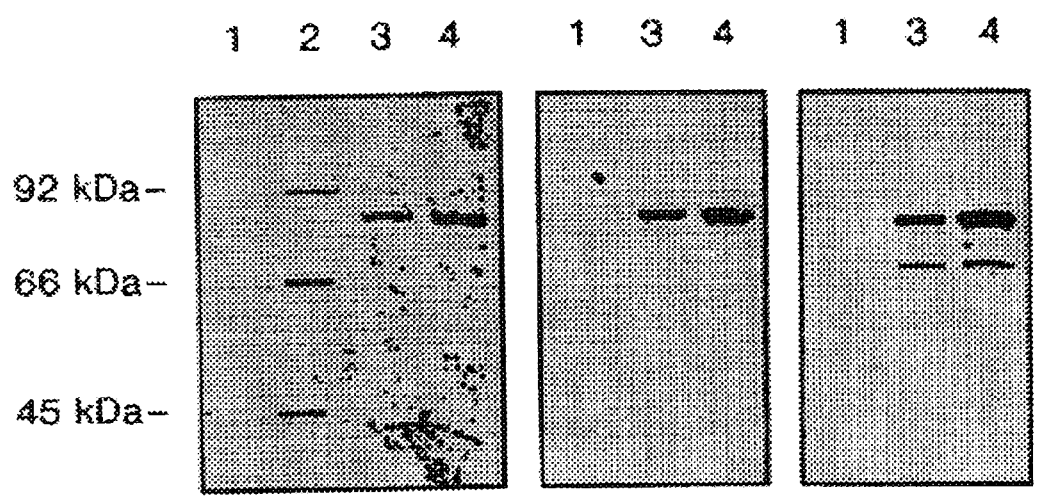
FIGS. 12A, 12B, and 12C collectively show the characterization of the material secreted after 4 days of culture (erlenmeyers) of the strain CBS 293.91 transformed with the plasmids pYG1266 (plasmid for expression of a chimera of the HSA-G.CSF type) and pKan707(control plasmid). In this experiment, the polypeptides for FIGS. 12A, 12B, 12C were run on the same gel (8.5% SDS-PAGE) and then treated separately.
Figure 13A:
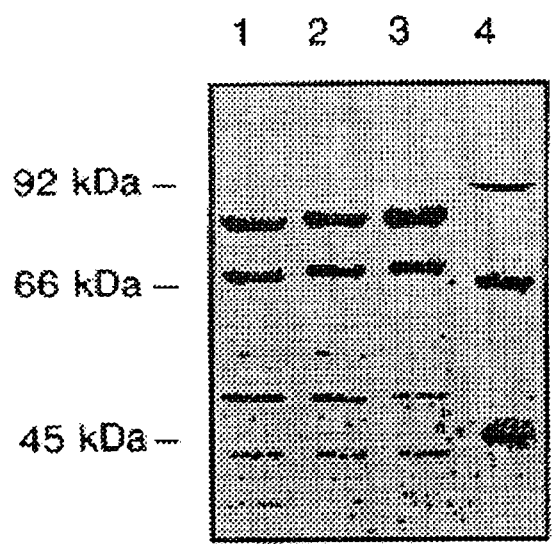
FIGS. 13A and B collectively show the characterization of the material secreted after 4 days of culture (erlenmeyers in YPD medium) of the strain CBS 293.91 transformed with the plasmids pYG1267 (chimera HSA-G.CSF), pYG1303 (chimera G.CSF-Gly4-HSA) and pYG1352 (chimera HSA-Gly4-G.CSF) after running on an 8.5% SDS-PAGE gel.
Figure 13B:
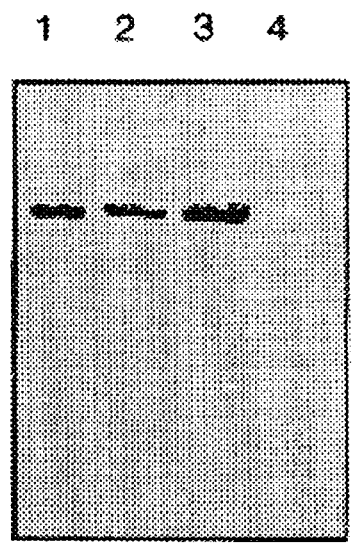

After selection on rich medium supplemented with G418, the recombinant clones are tested for their capacity to secrete the mature form of the chimeric proteins between HSA and G-CSF. A few clones corresponding to the strain K. lactis CBS 293.91 transformed with the plasmids pYG1266 or pYG1267 (HSA-G.CSF), pYG1302 or pYG1303 (G.CSF-Gly4-HSA) or alternatively pYG1351 or pYG1352 (HSA-Gly4-G.CSF) are incubated in selective complete liquid medium at 28° C. The cellular supernatants are then tested after electrophoresis on an 8.5% acrylamide gel, either directly by staining the gel with coomassie blue, or after immunoblotting using as primary antibodies rabbit polyclonal antibodies directed against the human G-CSF or a rabbit polyclonal serum directed against human albumin. The results of FIG. 12 demonstrate that the hybrid protein HSA-G.CSF is recognized both by antibodies directed against human albumin (panel C) and human G-CSF (panel B). The results of FIG. 13 indicate that the chimera HSA-Gly4-G.CSF (lane 3) is particularly well secreted by the yeast Kluyveromyces, possibly because of the fact that the presence of the peptide linker between the HSA part and the G-CSF part is more favourable to an independent folding of these 2 parts during the transit of the chimera in the secretory pathway. Furthermore, the N-terminal fusion (G.CSF-Gly4-HSA) is also secreted by the yeast Kluyveromyces (FIG. 13, lane 1).

E.9.3. Purification and Molecular Characterization of the Chimeras Between HSA and G-CSF.

After centrifugation of a culture of the CBS 293.91 strain transformed with the expression plasmids according to Example E.9.1., the culture supernatant is passed through a 0.22 mm filter (Millipore) and then concentrated by ultrafiltration (Amicon) using a membrane whose discrimination threshold is situated at 30 kDa. The concentrate obtained is then adjusted to 50 mM Tris-HCl from a IM stock solution of Tris-HCl (pH 6), and then loaded in 20 ml fractions onto an ion-exchange column (5 ml) (Q Fast Flow, Pharmacia) equilibrated in the same buffer. The chimeric protein is then eluted from the column by a gradient (0 to IM) of NaCl. The fractions containing the chimeric protein are then pooled and dialysed against a 50 mM Tris-HCl solution (pH 6) and reloaded onto a Q Fast Flow column (1 ml) equilibrated in the same buffer. After elution of the column, the fractions containing the protein are pooled, dialysed against water and freeze-dried before characterization: for example, the sequencing (Applied Biosystem) of the protein HSA-G.CSF secreted by the yeast CBS 293.91 gives the N-terminal sequence expected for HSA (Asp-Ala-His . . . ), demonstrating a correct maturation of the chimera immediately at the C-terminus of the doublet of residues Arg—Arg of the "pro" region of HSA (FIG. 2).

EXAMPLE 10

CHIMERAS DERIVED FROM AN IMMUNOGLOBULIN

E.10.1. Constructs

An Fv' fragment can be constructed by genetic engineering techniques, and which encodes the variable fragments of the heavy and light chains of an immunoglobulin (Ig), linked to each other by a linker peptide [Bird et al., Science (1988) 242: 423; Huston et al., (1988) Proc. Natl. Acad. Sci. 85: 5879]. Schematically, the variable regions (about 120 residues) of the heavy and light chains of a given Ig are cloned from the messenger RNA of the corresponding hybridoma, for example using the RT-PCR kit distributed by Pharmacia (Mouse ScFv module). In a second stage, the variable regions are genetically coupled by genetic engineering via a synthetic linkage peptide and for example the linker (GGGGS)×3. An MstII-HindIII restriction fragment including the Fv' fragment of an immunoglobulin secreted by a murine hybridoma is given in FIG. 14. The ligation of the HindIII-MstII fragment of the plasmid pYG404 to this MstII-HindIII fragment makes it possible to generate the HindIII fragment of the plasmid pYG1382 which encodes a chimeric protein in which the HSA molecule is genetically coupled to the Fv'fragment of FIG. 14 (chimera HSA-Fv'). The cloning in the productive orientation of the HindIII restriction fragment of the plasmid pYG1382 into the HindIII site of the plasmids pYG105 (LAC4) and pYG106 (PGK) generates the expression plasmids pYG1383 and pYG1384 respectively.

E.10.2. Secretion of the Hybrids

After selection on rich medium supplemented with G418, the recombinant clones are tested for their capacity to secrete the mature form of the chimeric protein HSA-Fv'. A few clones corresponding to the strain *K. lactis* CBS 293.91 transformed with the plasmids pYG1383 or pYG1384 (HSA-Fv') are incubated in selective complete liquid medium at 28° C. The cellular supernatants are then tested after electrophoresis on an 8.5% acrylamide gel, either directly by staining of the gel with coomassie blue, or after immunoblotting using as primary antibodies a rabbit polyclonal serum directed against human albumin, or directly incubated with biotinylated antibodies directed against the immunoglobulins of murine origin. The results of FIG. 15 demonstrate that the hybrid protein HSA-Fv' is recognized both by antibodies directed against human albumin (panel C) and reacts with biotinylated goat antibodies which are immunologically reactive towards mouse immunoglobulins (panel B).

EXAMPLE 11

BIOLOGICAL ACTIVITY OF THE CHIMERAS

E.11.1. Biological Activity In Vitro.

E.11.1.1. Chimeras Between HSA and vWF.

Figure 6A:
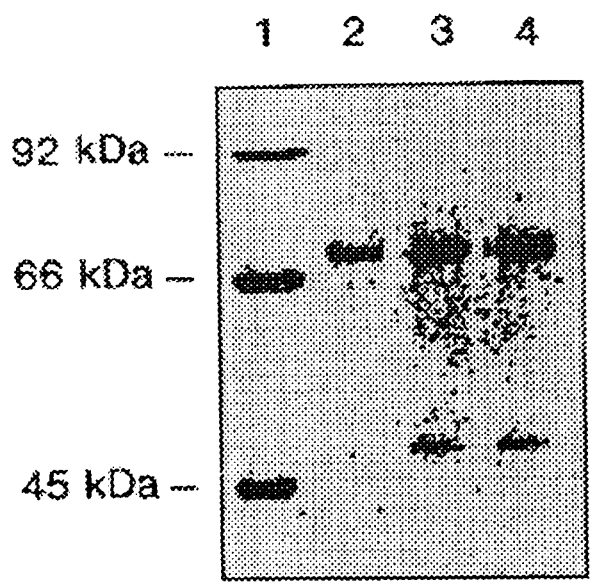
FIGS. 6A and 6B show the kinetic analysis of secretion of a chimera of the invention by the strain CBS 293.91 transformed with the plasmid pYG1206 (HSA-vWF Leu694-Pro708).
Figure 6B:
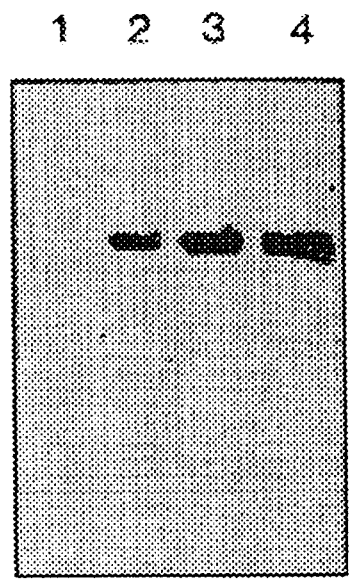
Figure 7:
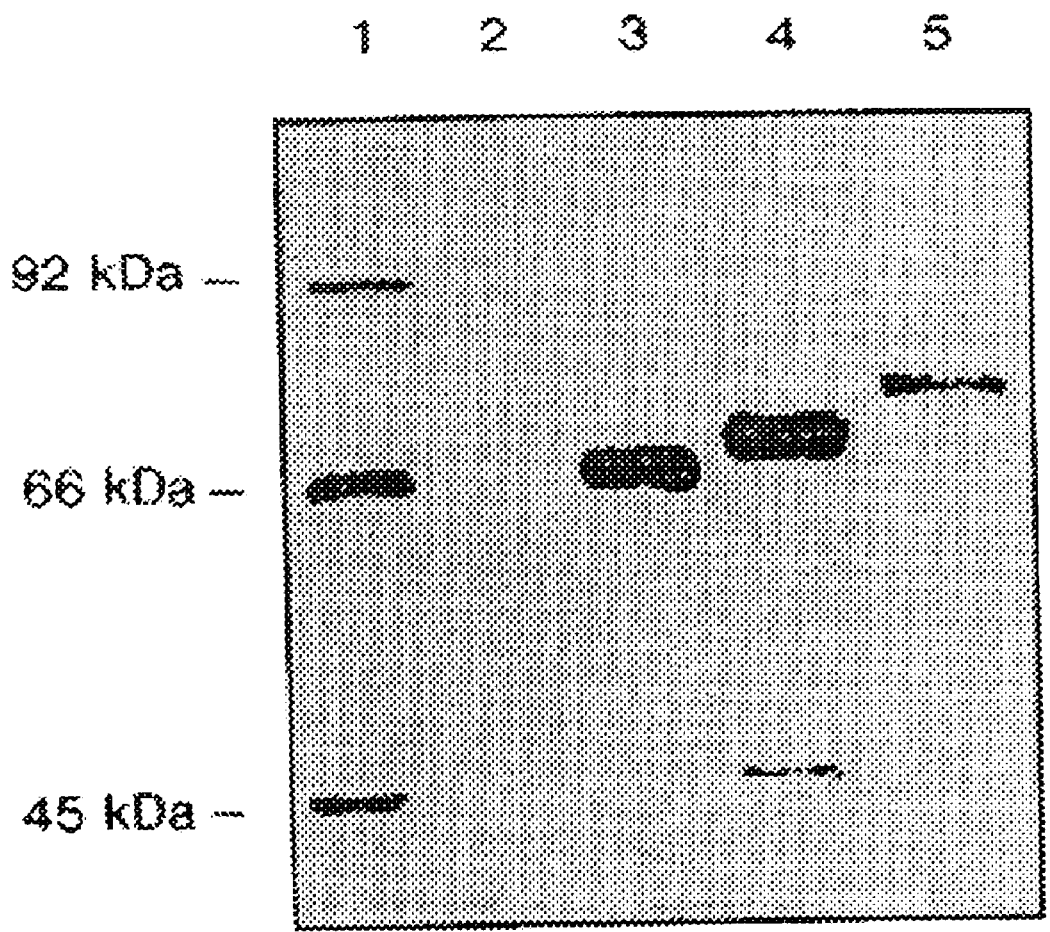
FIG. 7: Characterization of the material secreted by *K lactis* transformed with the plasmids pKan707(control plasmid, lane 2), pYG1206 (lane 3), pYG1214 (lane 4) and pYG1223 (lane 5); molecular weight standard (lane 1). The deposits correspond to 50 μl of supernatant from a stationary culture after growing in YPD medium, running on an 8.5% acrylamide gel and staining with coomassie blue.

The antagonistic activity of the products is determined by measuring the dose-dependent inhibition of the agglutination of human platelets fixed with paraformaldehyde according to the method described by Prior et al. [Bio/Technology (1992) 10: 66]. The measurements are carried out in an aggregameter (PAP-4, Bio Data, Horsham, Pa., U.S.A.) which records the variations over time of the optical transmission, with stirring, at 37° C. in the presence of vWF, of botrocetin (8.2 mg/ml) and of the test product at various dilutions (concentrations). For each measurement, 400 ml (8 x $10^7$ platelets) of a suspension of human platelets stabilized with paraformaldehyde (0.5%, and then resuspended in [NaCl (137 mM); MgCl2 (1 mM); NaH2 P04 (0.36 mM); NaHCO3 (10 mM); KCl (2.7 mM); glucose (5.6 mM); HSA (3.5 mg/ml); HEPES buffer (10 mM, pH 7.35)] are preincubated at 37° C. in the cylindrical tank (8.75×50 mm, Wellcome Distriwell, 159 rue Nationale, Paris) of the aggregameter for 4 min and are then supplemented with 30 ml of the solution of the test product at various dilutions in apyrogenic formulation vehicle [mannitol (50 g/l); citric acid (192 mg/l); L-lysine monohydrochloride (182.6 mg/l); NaCl (88 mg/i); pH adjusted to 3.5 by addition of NaOH (IM)], or formulation vehicle alone (control assay). The resulting suspension is then incubated for 1 min at 37° C. and 12.5 ml of human vWF [American Bioproducts, Parsippany, N.J., U.S.A.; 11% von Willebrand activity measured according to the recommendations for the use of PAP-4 (Platelet Aggregation Profiler®) with the aid of platelets fixed with formaldehyde (2 x $10^5$ platelets/ml), human plasma containing 0 to 100% vWF and ristocetin (10 mg/ml, cf. p. 36–45: vW Program ] are added and incubated at 37° C. for 1 min before adding 12.5 ml of botrocetin solution [purified from freeze-dried venom of Bothrops jararaca (Sigma) according to the procedure described by Sugimoto et al., Biochemistry (1991) 266: 18172]. The recording of the reading of the transmission as a function of time is then carried out for 2 min with stirring by means of a magnetic bar (Wellcome Distriwell) placed in the tank and with a magnetic stirring of 1,100 rpm provided by the aggregameter. The mean variation of the optical transmission (n3 5 for each dilution) over time is therefore a measurement of the platelet agglutination due to the presence of vWF and botrocetin, in the absence or in the presence of variable concentrations of the test product. From such recordings, the % inhibition of the platelet agglutination due to each concentration of product is then determined and the straight line giving the % inhibition as a function of the reciprocal of the product dilution in log—log scale is plotted. The IC50 (or concentration of product causing 50% inhibition of the agglutination) is then determined on this straight line. The table of FIG. 6 compares the IC50 values of some of the HSA-vWF chimeras of the present invention and demonstrates that some of them are better antagonists of platelet agglutination than the product RG12986 described by Prior et al. [Bio/Technology (1992) 10: 66] and included in the assays as standard value. Identical tests for the inhibition of the agglutination of human platelets in the presence of vWF of pig plasma (Sigma) makes it possible, furthermore, to demonstrate that some of the hybrids of the present invention, and especially some type IIB variants, are very good antagonists of platelet agglutination in the absence of botrocetin-type cofactors. The botrocetin-independent antagonism of these specific chimeras can also be demonstrated according to the procedure initially described by Ware et al. [Proc. Natl. Acad. Sci. (1991) 88: 2946] by displacing the monoclonal antibody 125 I-LJ-IB1 (10 mg/ml), a competitive inhibitor of the binding of vWF to the platelet GP1b [Handa M. et al., (1986) J. Biol. Chem. 261: 12579] after 30 mm of incubation at 22° C. in the presence of fresh platelets (108 platelets/ml).

E.11.1.2. Chimeras between HSA and G-CSF

The purified chimeras are tested for their capacity to permit the in vitro proliferation of the IL3-dependant murine line NFS60, by measuring the incorporation of tritiated thymidine essentially according to the procedure described by Tsuchiya et al. [Proc. Natl. Acad. Sci. (1986) 83 7633]. For each chimera, the measurements are carried out between 3 and 6 times in a three-point test (three dilutions of the product) in a zone or the relation between the quantity of active product and incorporation of labelled thymidine (Amersham) is linear. In each microtitre plate, the activity of a reference product consisting of recombinant human G-CSF expressed in mammalian cells is also systematically incorporated. The results of FIG. 17 demonstrate that the chimera HSA-G.CSF (pYG1266) secreted by the yeast Kluyveromyces and purified according to Example E.9.3. is capable in vitro of transducing a signal for cellular proliferation for the line NFS60. In this particular case, the specific activity (cpm/molarity) of the chimera is about 7 times lower than that of the reference G-CSF (non-coupled).

E.11.2. Biological Activity In Vivo

The activity of stimulation of the HSA-G-CSF chimeras on granulopoiesis in vivo is tested after subcutaneous injection in rats (Sprague-Dawley/CD, 250–300 g, 8–9 weeks) and compared to that of the reference G-CSF expressed using mammalian cells. Each product, tested at the rate of 7 animals, is injected subcutaneously into the dorso-scapular region at the rate of 100 ml for 7 consecutive days, (D1–D7). 500 ml of blood are collected on days D-6, D2 (before the 2nd injection). D5 (before the 5th injection) and D8, and a blood count is performed. In this test, the specific activity (neutropoiesis units/mole injected) of the chimera HSA-G.CSF (pYG1266) is identical to that of the reference G-CSF (FIG. 18). Since this specific chimera has in vitro a specific activity 7 times lower than that of the reference G-CSF (FIG. 17), it is therefore demonstrated that the genetic coupling of G-CSF onto HSA favourably modifies the pharmacokinetic properties thereof.

What is claimed is:

1. A fusion protein comprising erythropoietin and albumin or an albumin variant, wherein said fusion protein has a higher plasma stability than unfused erythropoietin, and wherein said albumin or albumin variant is located either at the N-terminus or C-terminus of said fusion protein.

2. The fusion protein of claim 1, comprising albumin.

3. The fusion protein of claim 1, comprising an albumin variant.

4. The fusion protein of claim 3, wherein said albumin variant is a fragment of albumin.

5. The fusion protein of claim 3, wherein said albumin variant is a mature form of albumin.

6. The fusion protein of claim 3, wherein said albumin variant has a mutation of one or more residues.

7. The fusion protein of claim 3, wherein said albumin variant has a deletion of one or more residues.

8. The fusion protein of claim 3, wherein said albumin variant has a mutation and deletion of one or more residues.

9. The fusion protein of claim 3, wherein said albumin variant has an addition of one or more residues.

10. The fusion protein of claim 1, wherein said fusion protein comprises an N-terminal Methionine.

11. The fusion protein of claim 1, wherein said fusion protein comprises a peptide linker.

12. The fusion protein of claim 1, wherein said fusion protein comprises a secretion signal sequence.

13. The fusion protein of claim 12, wherein said secretion signal sequence is the natural leader sequence of erythropoietin.

14. The fusion protein of claim 1, wherein said erythropoietin is fused to the N-terminal end of said albumin or albumin variant.

15. The fusion protein of claim 1, wherein said erythropoietin is fused to the C-terminal end of said albumin or albumin variant.

16. The fusion protein of claim 1, wherein said fusion protein is expressed by a prokaryotic cell.

17. The fusion protein of claim 16, wherein said fusion protein is expressed by a bacteria.

18. The fusion protein of claim 1, wherein said fusion protein is expressed by a eukaryotic cell.

19. The fusion protein of claim 18, wherein said fusion protein is expressed by an animal cell.

20. The fusion protein of claim 19, wherein said animal cell is a CHO cell.

21. The fusion protein of claim 19, wherein said animal cell is a COS cell.

22. The fusion protein of claim 1, wherein said fusion protein is expressed by a yeast.

23. The fusion protein of claim 22, wherein said yeast is Saccharomyces.

24. The fusion protein of claim 18, wherein said fusion protein is expressed by a fungi.

25. A composition comprising one or more fusion proteins of claim 1.

* * * * *

UNITED STATES PATENT AND TRADEMARK OFFICE
CERTIFICATE OF CORRECTION

PATENT NO. : 6,686,179 B2  
DATED : February 3, 2004  
INVENTOR(S) : Reinhard Fleer et al.

It is certified that error appears in the above-identified patent and that said Letters Patent is hereby corrected as shown below:

<u>Title page,</u>  
Item [56], References Cited, OTHER PUBLICATIONS, insert the following references:
-- Gijsens, A. et al., "Epidermal Growth Factor-mediated targeting of Chlorin $e_6$ selectively potentiates its photodynamic activity," *Cancer Research* 60:2197-2202 (2000).
Parhami-Seren, B. et al., "Monoclonal antibodies that distinguish between two related digitalis glycodises, Ouabain and Digoxin," *Jour. of Immunology* 163:4360-4366 (1999).
Phipps, R.P. et al., "Antibody isotypes mediating antigen retention in passively immunized mice," *Immunology* 40:459-466 (1980). --
"Braun, A., et al." last reference, "Interfero" should read -- Interferon --.
"Budkowska, A., et al." reference, "Charchterization" should read -- Characterization --.
"Chen, Y-M., et al." reference, "Gene" should read -- Case --.
"Fleer, R., et al." last reference, "Interstand" should read -- Interstrand --.
"Gijsens, M., et al." reference, "Gijsens" should read -- Girard --.
"Hattori, Y., et al." reference, "Activatio" should read -- Activation --.
"Hellstrom, U.B., et al." reference, "Responses" should read --Response --.
"Hiramatsu, R., et al." reference, "Mucro" should read -- Mucor --.
"Hiramatsu, R., et al." reference, "Mucro" should read -- Mucor --.
"Ikegaya, K., et al." reference, "Pibia" should read -- Pichia --.
"Kalman, M., et al." reference, "an" should read -- and --.
"Larsson, M., et al." reference, "Anexins" should read -- Annexins --.
"Latta, M., et al." reference, "E. Col" should read -- "E. coli --.
"Lewis, C., et al." reference, "Understudies" should read -- Understudied --.
"Mimran, A., et al." reference, "Tranlationally" should read -- Translationally --.
"Moore, K. L., et al." reference, "Immunization Growth" should read -- Immunization Against Growth --.
"Obayashi, H., et al." reference, "Superoxidee" should read -- Superoxide --.
"Ohtani, W., et al." reference, "Human Biochemistry" should read -- Analytical Biochemistry --.
"Okabayashi, K., et al." reference, "Secretory of" should read -- Secretory Expression of --.

UNITED STATES PATENT AND TRADEMARK OFFICE
CERTIFICATE OF CORRECTION

PATENT NO. : 6,686,179 B2
DATED : February 3, 2004
INVENTOR(S) : Reinhard Fleer et al.

It is certified that error appears in the above-identified patent and that said Letters Patent is hereby corrected as shown below:

OTHER PUBLICATIONS, cont'd,
"Parhami-Seren, D. S., et al.," reference "Parhami-Seren" should read -- Park --.
"Phipps, R. P., et al." reference, "Phipps, R.P." should read -- Pieper, F.R.--.
"Randem, I., et al." reference, "Randem" should read -- Randen --.
"Reed, R. G., et al." reference, "Half-Line" should read --Half-Life --.
"Rogovin, D., et al." reference, "Conjugatin" should read -- Conjugation --.
"Rostenberg, I." reference, "Gm an Inv" should read -- Gm and Inv --.
"Ruzgas, T. A., et al." reference, "th" should read -- the --.
"Ryff, J-C." reference, "αa" should read -- α2a --.
"Smedsrud, T., et al." "Salmon" should read -- Salmo --.
"Subbery, P.E., et al." reference, "Subbery" should read -- Sudbery --.
"Yeh, P., et al." reference, "IysA" should read -- lysA --.
"Yeh, P-H., et al." reference, "Iliosoas" should read -- Iliopsoas --.
"Zeng, F-Y., et al." reference, "Indistingusishable" should read -- Indistinguishable --.

Column 3,
Line 21, "0-glycosylation " should read -- O-glycosylation --.
Line 30, "Joining" should read -- joining --.

Column 7,
Line 51, "(HSA-UK→135)" should read -- (HSA-UK1→135) --.

Column 10,
Line 33, "MCI 1060" should read -- MC 1060 --.

Column 16,
Line 12, insert space between "(1987)" and -- 262 --.

Column 17,
Line 2, "VWF" should read -- vWF --.
Line 3, delete space before -- G, --.
Line 59, "IM" should read -- 1M --.

UNITED STATES PATENT AND TRADEMARK OFFICE
CERTIFICATE OF CORRECTION

PATENT NO. : 6,686,179 B2
DATED : February 3, 2004
INVENTOR(S) : Reinhard Fleer et al.

It is certified that error appears in the above-identified patent and that said Letters Patent is hereby corrected as shown below:

<u>Column 19,</u>
Line 12, delete space between "pYG" and -- 1351 --.
Line 12, delete space between "pYG" and -- 1352 --.
Line 37, delete space in this sequence line.

<u>Column 20,</u>
Line 27, "IM stock" should read -- 1M stock --.

<u>Column 21,</u>
Line 50, "88 mg/i" should read -- 88 mg/1 --.
Line 58, insert "$^{TM}$" after -- vWProgram --.

<u>Column 22,</u>
Line 28, "GPlb" should read -- GPIb --.

Signed and Sealed this

Eleventh Day of May, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,686,179 B2
DATED : February 3, 2004
INVENTOR(S) : Reinhard Fleer et al.

It is certified that error appears in the above-identified patent and that said Letters Patent is hereby corrected as shown below:

Column 6,
Line 28, "FIGS. 2(a) and 2(b)" should read -- FIGS. 2(a)-(c) --.
Line 44, "FIGS. 4A, 4B, 4C, 4D, and 4E" should read -- FIGS. 4A, 4B, 4C, 4D, 4E, and 4F --.
Lines 60-61, "FIG. 4E is" should read -- FIGS. 4E and 4F show --.

Column 8,
Line 6, "FIGS. 11(a) and 11(b)" should read -- FIGS. 11(a)-(d) --.

Signed and Sealed this

Twenty-seventh Day of December, 2005

JON W. DUDAS
*Director of the United States Patent and Trademark Office*

SEQUENCE LISTING (1) GENERAL INFORMATION:

(iii) NUMBER OF SEQUENCES: 36

(2) INFORMATION FOR SEQ ID NO: 1:

(i) SEQUENCE CHARACTERISTICS:
      (A) LENGTH: 1862 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: misc_feature
      (B) LOCATION: 1853..1855
      (D) OTHER INFORMATION: /note= "NNN is repeated p times"

(ix) FEATURE:
      (A) NAME/KEY: CDS
      (B) LOCATION: 26..1858

(xi) SEQUENCE DESCRIPTION: SEQ ID NO: 1:

```
AAGCTTTACA ACAAATATAA AAACA ATG AAG TGG GTA ACC TTT ATT TCC CTT      52
                            Met Lys Trp Val Thr Phe Ile Ser Leu
                             1               5

CTT TTT CTC TTT AGC TCG GCT TAT TCC AGG GGT GTG TTT CGT CGA GAT     100
Leu Phe Leu Phe Ser Ser Ala Tyr Ser Arg Gly Val Phe Arg Arg Asp
 10              15                  20                  25

GCA CAC AAG AGT GAG GTT GCT CAT CGG TTT AAA GAT TTG GGA GAA GAA     148
Ala His Lys Ser Glu Val Ala His Arg Phe Lys Asp Leu Gly Glu Glu
             30                  35                  40

AAT TTC AAA GCC TTG GTG TTG ATT GCC TTT GCT CAG TAT CTT CAG CAG     196
Asn Phe Lys Ala Leu Val Leu Ile Ala Phe Ala Gln Tyr Leu Gln Gln
             45                  50                  55

TGT CCA TTT GAA GAT CAT GTA AAA TTA GTG AAT GAA GTA ACT GAA TTT     244
Cys Pro Phe Glu Asp His Val Lys Leu Val Asn Glu Val Thr Glu Phe
         60                  65                  70

GCA AAA ACA TGT GTT GCT GAT GAG TCA GCT GAA AAT TGT GAC AAA TCA     292
Ala Lys Thr Cys Val Ala Asp Glu Ser Ala Glu Asn Cys Asp Lys Ser
         75                  80                  85

CTT CAT ACC CTT TTT GGA GAC AAA TTA TGC ACA GTT GCA ACT CTT CGT     340
Leu His Thr Leu Phe Gly Asp Lys Leu Cys Thr Val Ala Thr Leu Arg
 90                  95                 100                 105

GAA ACC TAT GGT GAA ATG GCT GAC TGC TGT GCA AAA CAA GAA CCT GAG     388
Glu Thr Tyr Gly Glu Met Ala Asp Cys Cys Ala Lys Gln Glu Pro Glu
                    110                 115                 120

AGA AAT GAA TGC TTC TTG CAA CAC AAA GAT GAC AAC CCA AAC CTC CCC     436
Arg Asn Glu Cys Phe Leu Gln His Lys Asp Asp Asn Pro Asn Leu Pro
                125                 130                 135

CGA TTG GTG AGA CCA GAG GTT GAT GTG ATG TGC ACT GCT TTT CAT GAC     484
Arg Leu Val Arg Pro Glu Val Asp Val Met Cys Thr Ala Phe His Asp
            140                 145                 150

AAT GAA GAG ACA TTT TTG AAA AAA TAC TTA TAT GAA ATT GCC AGA AGA     532
Asn Glu Glu Thr Phe Leu Lys Lys Tyr Leu Tyr Glu Ile Ala Arg Arg
            155                 160                 165

CAT CCT TAC TTT TAT GCC CCG GAA CTC CTT TTC TTT GCT AAA AGG TAT     580
His Pro Tyr Phe Tyr Ala Pro Glu Leu Leu Phe Phe Ala Lys Arg Tyr
170                 175                 180                 185

AAA GCT GCT TTT ACA GAA TGT TGC CAA GCT GCT GAT AAA GCT GCC TGC     628
Lys Ala Ala Phe Thr Glu Cys Cys Gln Ala Ala Asp Lys Ala Ala Cys
```

-continued

| | | |
|---|---|---|
| CTG TTG CCA AAG CTC GAT GAA CTT CGG GAT GAA GGG AAG GCT TCG TCT<br>Leu Leu Pro Lys Leu Asp Glu Leu Arg Asp Glu Gly Lys Ala Ser Ser<br>              205                      210                      215 | 676 |
| GCC AAA CAG AGA CTC AAG TGT GCC AGT CTC CAA AAA TTT GGA GAA AGA<br>Ala Lys Gln Arg Leu Lys Cys Ala Ser Leu Gln Lys Phe Gly Glu Arg<br>        220                      225                      230 | 724 |
| GCT TTC AAA GCA TGG GCA GTA GCT CGC CTG AGC CAG AGA TTT CCC AAA<br>Ala Phe Lys Ala Trp Ala Val Ala Arg Leu Ser Gln Arg Phe Pro Lys<br>235                      240                      245 | 772 |
| GCT GAG TTT GCA GAA GTT TCC AAG TTA GTG ACA GAT CTT ACC AAA GTC<br>Ala Glu Phe Ala Glu Val Ser Lys Leu Val Thr Asp Leu Thr Lys Val<br>250                  255                      260                      265 | 820 |
| CAC ACG GAA TGC TGC CAT GGA GAT CTG CTT GAA TGT GCT GAT GAC AGG<br>His Thr Glu Cys Cys His Gly Asp Leu Leu Glu Cys Ala Asp Asp Arg<br>                      270                      275                      280 | 868 |
| GCG GAC CTT GCC AAG TAT ATC TGT GAA AAT CAA GAT TCG ATC TCC AGT<br>Ala Asp Leu Ala Lys Tyr Ile Cys Glu Asn Gln Asp Ser Ile Ser Ser<br>        285                      290                      295 | 916 |
| AAA CTG AAG GAA TGC TGT GAA AAA CCT CTG TTG GAA AAA TCC CAC TGC<br>Lys Leu Lys Glu Cys Cys Glu Lys Pro Leu Leu Glu Lys Ser His Cys<br>300                      305                      310 | 964 |
| ATT GCC GAA GTG GAA AAT GAT GAG ATG CCT GCT GAC TTG CCT TCA TTA<br>Ile Ala Glu Val Glu Asn Asp Glu Met Pro Ala Asp Leu Pro Ser Leu<br>        315                      320                      325 | 1012 |
| GCT GCT GAT TTT GTT GAA AGT AAG GAT GTT TGC AAA AAC TAT GCT GAG<br>Ala Ala Asp Phe Val Glu Ser Lys Asp Val Cys Lys Asn Tyr Ala Glu<br>330                      335                      340                      345 | 1060 |
| GCA AAG GAT GTC TTC CTG GGC ATG TTT TTG TAT GAA TAT GCA AGA AGG<br>Ala Lys Asp Val Phe Leu Gly Met Phe Leu Tyr Glu Tyr Ala Arg Arg<br>                      350                      355                      360 | 1108 |
| CAT CCT GAT TAC TCT GTC GTA CTG CTG CTG AGA CTT GCC AAG ACA TAT<br>His Pro Asp Tyr Ser Val Val Leu Leu Leu Arg Leu Ala Lys Thr Tyr<br>                365                      370                      375 | 1156 |
| GAA ACC ACT CTA GAG AAG TGC TGT GCC GCT GCA GAT CCT CAT GAA TGC<br>Glu Thr Thr Leu Glu Lys Cys Cys Ala Ala Ala Asp Pro His Glu Cys<br>                380                      385                      390 | 1204 |
| TAT GCC AAA GTG TTC GAT GAA TTT AAA CCT CTT GTG GAA GAG CCT CAG<br>Tyr Ala Lys Val Phe Asp Glu Phe Lys Pro Leu Val Glu Glu Pro Gln<br>395                      400                      405 | 1252 |
| AAT TTA ATC AAA CAA AAT TGT GAG CTT TTT GAG CAG CTT GGA GAG TAC<br>Asn Leu Ile Lys Gln Asn Cys Glu Leu Phe Glu Gln Leu Gly Glu Tyr<br>410                      415                      420                      425 | 1300 |
| AAA TTC CAG AAT GCG CTA TTA GTT CGT TAC ACC AAG AAA GTA CCC CAA<br>Lys Phe Gln Asn Ala Leu Leu Val Arg Tyr Thr Lys Lys Val Pro Gln<br>                430                      435                      440 | 1348 |
| GTG TCA ACT CCA ACT CTT GTA GAG GTC TCA AGA AAC CTA GGA AAA GTG<br>Val Ser Thr Pro Thr Leu Val Glu Val Ser Arg Asn Leu Gly Lys Val<br>                445                      450                      455 | 1396 |
| GGC AGC AAA TGT TGT AAA CAT CCT GAA GCA AAA AGA ATG CCC TGT GCA<br>Gly Ser Lys Cys Cys Lys His Pro Glu Ala Lys Arg Met Pro Cys Ala<br>                      460                      465                      470 | 1444 |
| GAA GAC TAT CTA TCC GTG GTC CTG AAC CAG TTA TGT GTG TTG CAT GAG<br>Glu Asp Tyr Leu Ser Val Val Leu Asn Gln Leu Cys Val Leu His Glu<br>475                      480                      485 | 1492 |
| AAA ACG CCA GTA AGT GAC AGA GTC ACC AAA TGC TGC ACA GAA TCC TTG<br>Lys Thr Pro Val Ser Asp Arg Val Thr Lys Cys Cys Thr Glu Ser Leu<br>490                      495                      500                      505 | 1540 |
| GTG AAC AGG CGA CCA TGC TTT TCA GCT CTG GAA GTC GAT GAA ACA TAC | 1588 |

```
Val Asn Arg Arg Pro Cys Phe Ser Ala Leu Glu Val Asp Glu Thr Tyr
            510                 515                 520

GTT CCC AAA GAG TTT AAT GCT GAA ACA TTC ACC TTC CAT GCA GAT ATA      1636
Val Pro Lys Glu Phe Asn Ala Glu Thr Phe Thr Phe His Ala Asp Ile
            525                 530                 535

TGC ACA CTT TCT GAG AAG GAG AGA CAA ATC AAG AAA CAA ACT GCA CTT      1684
Cys Thr Leu Ser Glu Lys Glu Arg Gln Ile Lys Lys Gln Thr Ala Leu
            540                 545                 550

GTT GAG CTT GTG AAA CAC AAG CCC AAG GCA ACA AAA GAG CAA CTG AAA      1732
Val Glu Leu Val Lys His Lys Pro Lys Ala Thr Lys Glu Gln Leu Lys
            555                 560                 565

GCT GTT ATG GAT GAT TTC GCA GCT TTT GTA GAG AAG TGC TGC AAG GCT      1780
Ala Val Met Asp Asp Phe Ala Ala Phe Val Glu Lys Cys Cys Lys Ala
570                 575                 580                 585

GAC GAT AAG GAG ACC TGC TTT GCC GAG GAG GGT AAA AAA CTT GTT GCT      1828
Asp Asp Lys Glu Thr Cys Phe Ala Glu Glu Gly Lys Lys Leu Val Ala
            590                 595                 600

GCA AGT CAA GCT GCC TTA GGC TTA NNN TAAGCTT                          1862
Ala Ser Gln Ala Ala Leu Gly Leu Xaa
            605                 610

(2) INFORMATION FOR SEQ ID NO: 2:

(i) SEQUENCE CHARACTERISTICS:
        (A) LENGTH: 610 amino acids
        (B) TYPE: amino acid
        (D) TOPOLOGY: linear (ii) MOLECULE TYPE: protein (xi) SEQUENCE DESCRIPTION: SEQ ID NO: 2:

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
            85                  90                  95

Lys Leu Cys Thr Val Ala Thr Leu Arg Glu Thr Tyr Gly Glu Met Ala
        100                 105                 110

Asp Cys Cys Ala Lys Gln Glu Pro Glu Arg Asn Glu Cys Phe Leu Gln
    115                 120                 125

His Lys Asp Asp Asn Pro Asn Leu Pro Arg Leu Val Arg Pro Glu Val
130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
            165                 170                 175

Glu Leu Leu Phe Phe Ala Lys Arg Tyr Lys Ala Ala Phe Thr Glu Cys
        180                 185                 190

Cys Gln Ala Ala Asp Lys Ala Ala Cys Leu Leu Pro Lys Leu Asp Glu
    195                 200                 205

Leu Arg Asp Glu Gly Lys Ala Ser Ser Ala Lys Gln Arg Leu Lys Cys
```

-continued

```
            210                 215                 220
Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
                260                 265                 270

Asp Leu Leu Glu Cys Ala Asp Asp Arg Ala Asp Leu Ala Lys Tyr Ile
                275                 280                 285

Cys Glu Asn Gln Asp Ser Ile Ser Ser Lys Leu Lys Glu Cys Cys Glu
                290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
                340                 345                 350

Met Phe Leu Tyr Glu Tyr Ala Arg Arg His Pro Asp Tyr Ser Val Val
                355                 360                 365

Leu Leu Leu Arg Leu Ala Lys Thr Tyr Glu Thr Thr Leu Glu Lys Cys
370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
                420                 425                 430

Val Arg Tyr Thr Lys Lys Val Pro Gln Val Ser Thr Pro Thr Leu Val
                435                 440                 445

Glu Val Ser Arg Asn Leu Gly Lys Val Gly Ser Lys Cys Cys Lys His
                450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
                500                 505                 510

Ser Ala Leu Glu Val Asp Glu Thr Tyr Val Pro Lys Glu Phe Asn Ala
                515                 520                 525

Glu Thr Phe Thr Phe His Ala Asp Ile Cys Thr Leu Ser Glu Lys Glu
                530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
                580                 585                 590

Ala Glu Glu Gly Lys Lys Leu Val Ala Ala Ser Gln Ala Ala Leu Gly
                595                 600                 605

Leu Xaa
    610
```

(2) INFORMATION FOR SEQ ID NO: 3:

(i) SEQUENCE CHARACTERISTICS:
    (A) LENGTH: 750 base pairs
    (B) TYPE: nucleic acid
    (C) STRANDEDNESS: double
    (D) TOPOLOGY: linear (ii) MOLECULE TYPE: cDNA (ix) FEATURE:
    (A) NAME/KEY: CDS
    (B) LOCATION: 3..746

(xi) SEQUENCE DESCRIPTION: SEQ ID NO: 3:

```
CC TTA GGC TTA ACC TGT GAA GCC TGC CAG GAG CCG GGA GGC CTG GTG         47
   Leu Gly Leu Thr Cys Glu Ala Cys Gln Glu Pro Gly Gly Leu Val
    1               5                  10                  15

GTG CCT CCC ACA GAT GCC CCG GTG AGC CCC ACC ACT CTG TAT GTG GAG         95
Val Pro Pro Thr Asp Ala Pro Val Ser Pro Thr Thr Leu Tyr Val Glu
                 20                  25                  30

GAC ATC TCG GAA CCG CCG TTG CAC GAT TTC TAC TGC AGC AGG CTA CTG        143
Asp Ile Ser Glu Pro Pro Leu His Asp Phe Tyr Cys Ser Arg Leu Leu
             35                  40                  45

GAC CTG GTC TTC CTG CTG GAT GGC TCC TCC AGG CTG TCC GAG GCT GAG        191
Asp Leu Val Phe Leu Leu Asp Gly Ser Ser Arg Leu Ser Glu Ala Glu
         50                  55                  60

TTT GAA GTG CTG AAG GCC TTT GTG GTG GAC ATG ATG GAG CGG CTG CGC        239
Phe Glu Val Leu Lys Ala Phe Val Val Asp Met Met Glu Arg Leu Arg
     65                  70                  75

ATC TCC CAG AAG TGG GTC CGC GTG GCC GTG GTG GAG TAC CAC GAC GGC        287
Ile Ser Gln Lys Trp Val Arg Val Ala Val Val Glu Tyr His Asp Gly
 80                  85                  90                  95

TCC CAC GCC TAC ATC GGG CTC AAG GAC CGG AAG CGA CCG TCA GAG CTG        335
Ser His Ala Tyr Ile Gly Leu Lys Asp Arg Lys Arg Pro Ser Glu Leu
                100                 105                 110

CGG CGC ATT GCC AGC CAG GTG AAG TAT GCG GGC AGC CAG GTG GCC TCC        383
Arg Arg Ile Ala Ser Gln Val Lys Tyr Ala Gly Ser Gln Val Ala Ser
            115                 120                 125

ACC AGC GAG GTC TTG AAA TAC ACA CTG TTC CAA ATC TTC AGC AAG ATC        431
Thr Ser Glu Val Leu Lys Tyr Thr Leu Phe Gln Ile Phe Ser Lys Ile
        130                 135                 140

GAC CGC CCT GAA GCC TCC CGC ATC GCC CTG CTC CTG ATG GCC AGC CAG        479
Asp Arg Pro Glu Ala Ser Arg Ile Ala Leu Leu Leu Met Ala Ser Gln
    145                 150                 155

GAG CCC CAA CGG ATG TCC CGG AAC TTT GTC CGC TAC GTC CAG GGC CTG        527
Glu Pro Gln Arg Met Ser Arg Asn Phe Val Arg Tyr Val Gln Gly Leu
160                 165                 170                 175

AAG AAG AAG AAG GTC ATT GTG ATC CCG GTG GGC ATT GGG CCC CAT GCC        575
Lys Lys Lys Lys Val Ile Val Ile Pro Val Gly Ile Gly Pro His Ala
                180                 185                 190

AAC CTC AAG CAG ATC CGC CTC ATC GAG AAG CAG GCC CCT GAG AAC AAG        623
Asn Leu Lys Gln Ile Arg Leu Ile Glu Lys Gln Ala Pro Glu Asn Lys
            195                 200                 205

GCC TTC GTG CTG AGC AGT GTG GAT GAG CTG GAG CAG CAA AGG GAC GAG        671
Ala Phe Val Leu Ser Ser Val Asp Glu Leu Glu Gln Gln Arg Asp Glu
        210                 215                 220

ATC GTT AGC TAC CTC TGT GAC CTT GCC CCT GAA GCC CCT CCT CCT ACT        719
Ile Val Ser Tyr Leu Cys Asp Leu Ala Pro Glu Ala Pro Pro Pro Thr
    225                 230                 235

CTG CCC CCC GAC ATG GCA CAA GTC TAAGCTT                                750
Leu Pro Pro Asp Met Ala Gln Val
240                 245
```

(2) INFORMATION FOR SEQ ID NO: 4:

(i) SEQUENCE CHARACTERISTICS:
        (A) LENGTH: 247 amino acids
        (B) TYPE: amino acid
        (D) TOPOLOGY: linear (ii) MOLECULE TYPE: protein (xi) SEQUENCE DESCRIPTION: SEQ ID NO: 4:

```
Leu Gly Leu Thr Cys Glu Ala Cys Gln Glu Pro Gly Gly Leu Val Val
  1               5                  10                  15

Pro Pro Thr Asp Ala Pro Val Ser Pro Thr Thr Leu Tyr Val Glu Asp
             20                  25                  30

Ile Ser Glu Pro Pro Leu His Asp Phe Tyr Cys Ser Arg Leu Leu Asp
         35                  40                  45

Leu Val Phe Leu Leu Asp Gly Ser Ser Arg Leu Ser Glu Ala Glu Phe
     50                  55                  60

Glu Val Leu Lys Ala Phe Val Val Asp Met Met Glu Arg Leu Arg Ile
 65                  70                  75                  80

Ser Gln Lys Trp Val Arg Val Ala Val Val Glu Tyr His Asp Gly Ser
                 85                  90                  95

His Ala Tyr Ile Gly Leu Lys Asp Arg Lys Arg Pro Ser Glu Leu Arg
                100                 105                 110

Arg Ile Ala Ser Gln Val Lys Tyr Ala Gly Ser Gln Val Ala Ser Thr
            115                 120                 125

Ser Glu Val Leu Lys Tyr Thr Leu Phe Gln Ile Phe Ser Lys Ile Asp
        130                 135                 140

Arg Pro Glu Ala Ser Arg Ile Ala Leu Leu Leu Met Ala Ser Gln Glu
145                 150                 155                 160

Pro Gln Arg Met Ser Arg Asn Phe Val Arg Tyr Val Gln Gly Leu Lys
                165                 170                 175

Lys Lys Lys Val Ile Val Ile Pro Val Gly Ile Gly Pro His Ala Asn
            180                 185                 190

Leu Lys Gln Ile Arg Leu Ile Glu Lys Gln Ala Pro Glu Asn Lys Ala
        195                 200                 205

Phe Val Leu Ser Ser Val Asp Glu Leu Glu Gln Gln Arg Asp Glu Ile
    210                 215                 220

Val Ser Tyr Leu Cys Asp Leu Ala Pro Glu Ala Pro Pro Thr Leu
225                 230                 235                 240

Pro Pro Asp Met Ala Gln Val
                245
```

(2) INFORMATION FOR SEQ ID NO: 5:

(i) SEQUENCE CHARACTERISTICS:
        (A) LENGTH: 105 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 3..101

(xi) SEQUENCE DESCRIPTION: SEQ ID NO: 5:

```
CC TTA GGC TTA ACC TGT GAA GCC TGC CAG GAG CCG GGA GGC CTG GTG         47
   Leu Gly Leu Thr Cys Glu Ala Cys Gln Glu Pro Gly Gly Leu Val
```

```
               1               5                  10                 15
GTG CCT CCC ACA GAT GCC CCG GTG AGC CCC ACC ACT CTG TAT GTG GAG        95
Val Pro Pro Thr Asp Ala Pro Val Ser Pro Thr Thr Leu Tyr Val Glu
                        20                  25                  30

GAC TAAGCTT                                                           105
Asp (2) INFORMATION FOR SEQ ID NO: 6:

(i) SEQUENCE CHARACTERISTICS:
        (A) LENGTH: 32 amino acids
        (B) TYPE: amino acid
        (D) TOPOLOGY: linear (ii) MOLECULE TYPE: protein (xi) SEQUENCE DESCRIPTION: SEQ ID NO: 6:

Leu Gly Leu Thr Cys Glu Ala Cys Gln Glu Pro Gly Gly Leu Val Val
 1               5                  10                  15

Pro Pro Thr Asp Ala Pro Val Ser Pro Thr Thr Leu Tyr Val Glu Asp
                20                  25                  30

(2) INFORMATION FOR SEQ ID NO: 7:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 3..56

(xi) SEQUENCE DESCRIPTION: SEQ ID NO: 7:

CC TTA GGC CTC TGT GAC CTT GCC CCT GAA GCC CCT CCT CCT ACT CTG        47
   Leu Gly Leu Cys Asp Leu Ala Pro Glu Ala Pro Pro Pro Thr Leu
    1               5                  10                  15

CCC CCC TAAGCTT                                                        60
Pro Pro (2) INFORMATION FOR SEQ ID NO: 8:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO: 8:

Leu Gly Leu Cys Asp Leu Ala Pro Glu Ala Pro Pro Pro Thr Leu Pro
 1               5                  10                  15

Pro (2) INFORMATION FOR SEQ ID NO: 9:

(i) SEQUENCE CHARACTERISTICS:
        (A) LENGTH: 288 base pairs
        (B) TYPE: nucleic acid
        (C) STRANDEDNESS: double
        (D) TOPOLOGY: linear (ii) MOLECULE TYPE: cDNA
```

```
    (ix) FEATURE:
         (A) NAME/KEY: CDS
         (B) LOCATION: 3..284

(xi) SEQUENCE DESCRIPTION: SEQ ID NO: 9:

CC TTA GGC TTA ACC TGT GAA GCC TGC CAG GAG CCG GGA GGC CTG GTG        47
   Leu Gly Leu Thr Cys Glu Ala Cys Gln Glu Pro Gly Gly Leu Val
    1               5                  10                  15

GTG CCT CCC ACA GAT GCC CCG GTG AGC CCC ACC ACT CTG TAT GTG GAG       95
Val Pro Pro Thr Asp Ala Pro Val Ser Pro Thr Thr Leu Tyr Val Glu
                 20                  25                  30

GAC ATC TCG GAA CCG CCG TTG CAC GAT TTC TAC CGC CTC ATC GAG AAG      143
Asp Ile Ser Glu Pro Pro Leu His Asp Phe Tyr Arg Leu Ile Glu Lys
             35                  40                  45

CAG GCC CCT GAG AAC AAG GCC TTC GTG CTG AGC AGT GTG GAT GAG CTG      191
Gln Ala Pro Glu Asn Lys Ala Phe Val Leu Ser Ser Val Asp Glu Leu
         50                  55                  60

GAG CAG CAA AGG GAC GAG ATC GTT AGC TAC CTC TGT GAC CTT GCC CCT      239
Glu Gln Gln Arg Asp Glu Ile Val Ser Tyr Leu Cys Asp Leu Ala Pro
 65                  70                  75

GAA GCC CCT CCT CCT ACT CTG CCC CCC GAC ATG GCA CAA GTC TAAGCTT      288
Glu Ala Pro Pro Pro Thr Leu Pro Pro Asp Met Ala Gln Val
 80                  85                  90

(2) INFORMATION FOR SEQ ID NO: 10:

(i) SEQUENCE CHARACTERISTICS:
        (A) LENGTH: 93 amino acids
        (B) TYPE: amino acid
        (D) TOPOLOGY: linear (ii) MOLECULE TYPE: protein (xi) SEQUENCE DESCRIPTION: SEQ ID NO: 10:

Leu Gly Leu Thr Cys Glu Ala Cys Gln Glu Pro Gly Gly Leu Val Val
 1               5                  10                  15

Pro Pro Thr Asp Ala Pro Val Ser Pro Thr Thr Leu Tyr Val Glu Asp
                 20                  25                  30

Ile Ser Glu Pro Pro Leu His Asp Phe Tyr Arg Leu Ile Glu Lys Gln
             35                  40                  45

Ala Pro Glu Asn Lys Ala Phe Val Leu Ser Ser Val Asp Glu Leu Glu
         50                  55                  60

Gln Gln Arg Asp Glu Ile Val Ser Tyr Leu Cys Asp Leu Ala Pro Glu
 65                  70                  75                  80

Ala Pro Pro Pro Thr Leu Pro Pro Asp Met Ala Gln Val
                 85                  90

(2) INFORMATION FOR SEQ ID NO: 11:

(i) SEQUENCE CHARACTERISTICS:
        (A) LENGTH: 423 base pairs
        (B) TYPE: nucleic acid
        (C) STRANDEDNESS: double
        (D) TOPOLOGY: linear (ii) MOLECULE TYPE: cDNA (ix) FEATURE:
         (A) NAME/KEY: CDS
         (B) LOCATION: 3..419

(xi) SEQUENCE DESCRIPTION: SEQ ID NO: 11:

CC TTA GGC TTA AGC AAT GAA CTT CAT CAA GTT CCA TCG AAC TGT GAC        47
```

```
        Leu Gly Leu Ser Asn Glu Leu His Gln Val Pro Ser Asn Cys Asp
        1               5                  10                  15

TGT CTA AAT GGA GGA ACA TGT GTG TCC AAC AAG TAC TTC TCC AAC ATT          95
Cys Leu Asn Gly Gly Thr Cys Val Ser Asn Lys Tyr Phe Ser Asn Ile
                 20                  25                  30

CAC TGG TGC AAC TGC CCA AAG AAA TTC GGA GGG CAG CAC TGT GAA ATA         143
His Trp Cys Asn Cys Pro Lys Lys Phe Gly Gly Gln His Cys Glu Ile
             35                  40                  45

GAT AAG TCA AAA ACC TGC TAT GAG GGG AAT GGT CAC TTT TAC CGA GGA         191
Asp Lys Ser Lys Thr Cys Tyr Glu Gly Asn Gly His Phe Tyr Arg Gly
         50                  55                  60

AAG GCC AGC ACT GAC ACC ATG GGC CGG CCC TGC CTG CCC TGG AAC TCT         239
Lys Ala Ser Thr Asp Thr Met Gly Arg Pro Cys Leu Pro Trp Asn Ser
     65                  70                  75

GCC ACT GTC CTT CAG CAA ACG TAC CAT GCC CAC AGA TCT GAT GCT CTT         287
Ala Thr Val Leu Gln Gln Thr Tyr His Ala His Arg Ser Asp Ala Leu
 80                  85                  90                  95

CAG CTG GGC CTG GGG AAA CAT AAT TAC TGC AGG AAC CCA GAC AAC CGG         335
Gln Leu Gly Leu Gly Lys His Asn Tyr Cys Arg Asn Pro Asp Asn Arg
                 100                 105                 110

AGG CGA CCC TGG TGC TAT GTG CAG GTG GGC CTA AAG CCG CTT GTC CAA         383
Arg Arg Pro Trp Cys Tyr Val Gln Val Gly Leu Lys Pro Leu Val Gln
             115                 120                 125

GAG TGC ATG GTG CAT GAC TGC GCA GAT GGA AAA TAAGCTT                     423
Glu Cys Met Val His Asp Cys Ala Asp Gly Lys
         130                 135

(2) INFORMATION FOR SEQ ID NO: 12:

(i) SEQUENCE CHARACTERISTICS:
        (A) LENGTH: 138 amino acids
        (B) TYPE: amino acid
        (D) TOPOLOGY: linear (ii) MOLECULE TYPE: protein (xi) SEQUENCE DESCRIPTION: SEQ ID NO: 12:

Leu Gly Leu Ser Asn Glu Leu His Gln Val Pro Ser Asn Cys Asp Cys
1               5                  10                  15

Leu Asn Gly Gly Thr Cys Val Ser Asn Lys Tyr Phe Ser Asn Ile His
            20                  25                  30

Trp Cys Asn Cys Pro Lys Lys Phe Gly Gly Gln His Cys Glu Ile Asp
        35                  40                  45

Lys Ser Lys Thr Cys Tyr Glu Gly Asn Gly His Phe Tyr Arg Gly Lys
    50                  55                  60

Ala Ser Thr Asp Thr Met Gly Arg Pro Cys Leu Pro Trp Asn Ser Ala
65                  70                  75                  80

Thr Val Leu Gln Gln Thr Tyr His Ala His Arg Ser Asp Ala Leu Gln
            85                  90                  95

Leu Gly Leu Gly Lys His Asn Tyr Cys Arg Asn Pro Asp Asn Arg Arg
        100                 105                 110

Arg Pro Trp Cys Tyr Val Gln Val Gly Leu Lys Pro Leu Val Gln Glu
    115                 120                 125

Cys Met Val His Asp Cys Ala Asp Gly Lys
        130                 135

(2) INFORMATION FOR SEQ ID NO: 13:

(i) SEQUENCE CHARACTERISTICS:
        (A) LENGTH: 541 base pairs
```

(B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 3..536

(xi) SEQUENCE DESCRIPTION: SEQ ID NO: 13:

```
CC TTA GGC TTA ACC CCC CTG GGC CCT GCC AGC TCC CTG CCC CAG AGC         47
   Leu Gly Leu Thr Pro Leu Gly Pro Ala Ser Ser Leu Pro Gln Ser
    1               5                  10                  15

TTC CTG CTC AAG TGC TTA GAG CAA GTG AGG AAG ATC CAG GGC GAT GGC        95
Phe Leu Leu Lys Cys Leu Glu Gln Val Arg Lys Ile Gln Gly Asp Gly
                20                  25                  30

GCA GCG CTC CAG GAG AAG CTG TGT GCC ACC TAC AAG CTG TGC CAC CCC       143
Ala Ala Leu Gln Glu Lys Leu Cys Ala Thr Tyr Lys Leu Cys His Pro
         35                  40                  45

GAG GAG CTG GTG CTG CTC GGA CAC TCT CTG GGC ATC CCC TGG GCT CCC       191
Glu Glu Leu Val Leu Leu Gly His Ser Leu Gly Ile Pro Trp Ala Pro
     50                  55                  60

CTG AGC TCC TGC CCC AGC CAG GCC CTG CAG CTG GCA GGC TGC TTG AGC       239
Leu Ser Ser Cys Pro Ser Gln Ala Leu Gln Leu Ala Gly Cys Leu Ser
 65                  70                  75

CAA CTC CAT AGC GGC CTT TTC CTC TAC CAG GGG CTC CTG CAG GCC CTG       287
Gln Leu His Ser Gly Leu Phe Leu Tyr Gln Gly Leu Leu Gln Ala Leu
 80                  85                  90                  95

GAA GGG ATA TCC CCC GAG TTG GGT CCC ACC TTG GAC ACA CTG CAG CTG       335
Glu Gly Ile Ser Pro Glu Leu Gly Pro Thr Leu Asp Thr Leu Gln Leu
                100                 105                 110

GAC GTC GCC GAC TTT GCC ACC ACC ATC TGG CAG CAG ATG GAA GAA CTG       383
Asp Val Ala Asp Phe Ala Thr Thr Ile Trp Gln Gln Met Glu Glu Leu
            115                 120                 125

GGA ATG GCC CCT GCC CTG CAG CCC ACC CAG GGT GCC ATG CCG GCC TTC       431
Gly Met Ala Pro Ala Leu Gln Pro Thr Gln Gly Ala Met Pro Ala Phe
        130                 135                 140

GCC TCT GCT TTC CAG CGC CGG GCA GGA GGG GTC CTG GTT GCT AGC CAT       479
Ala Ser Ala Phe Gln Arg Arg Ala Gly Gly Val Leu Val Ala Ser His
    145                 150                 155

CTG CAG AGC TTC CTG GAG GTG TCG TAC CGC GTT CTA CGC CAC CTT GCG       527
Leu Gln Ser Phe Leu Glu Val Ser Tyr Arg Val Leu Arg His Leu Ala
160                 165                 170                 175

CAG CCC TGAAGCTT                                                      541
Gln Pro
```

(2) INFORMATION FOR SEQ ID NO: 14:

(i) SEQUENCE CHARACTERISTICS:
        (A) LENGTH: 177 amino acids
        (B) TYPE: amino acid
        (D) TOPOLOGY: linear (ii) MOLECULE TYPE: protein (xi) SEQUENCE DESCRIPTION: SEQ ID NO: 14:

```
Leu Gly Leu Thr Pro Leu Gly Pro Ala Ser Ser Leu Pro Gln Ser Phe
 1               5                  10                  15

Leu Leu Lys Cys Leu Glu Gln Val Arg Lys Ile Gln Gly Asp Gly Ala
            20                  25                  30

Ala Leu Gln Glu Lys Leu Cys Ala Thr Tyr Lys Leu Cys His Pro Glu
        35                  40                  45
```

```
Glu Leu Val Leu Leu Gly His Ser Leu Gly Ile Pro Trp Ala Pro Leu
 50                  55                  60

Ser Ser Cys Pro Ser Gln Ala Leu Gln Leu Ala Gly Cys Leu Ser Gln
 65                  70                  75                  80

Leu His Ser Gly Leu Phe Leu Tyr Gln Gly Leu Leu Gln Ala Leu Glu
                 85                  90                  95

Gly Ile Ser Pro Glu Leu Gly Pro Thr Leu Asp Thr Leu Gln Leu Asp
                100                 105                 110

Val Ala Asp Phe Ala Thr Thr Ile Trp Gln Gln Met Glu Glu Leu Gly
            115                 120                 125

Met Ala Pro Ala Leu Gln Pro Thr Gln Gly Ala Met Pro Ala Phe Ala
130                 135                 140

Ser Ala Phe Gln Arg Arg Ala Gly Gly Val Leu Val Ala Ser His Leu
145                 150                 155                 160

Gln Ser Phe Leu Glu Val Ser Tyr Arg Val Leu Arg His Leu Ala Gln
                165                 170                 175

Pro
```

(2) INFORMATION FOR SEQ ID NO: 15:

(i) SEQUENCE CHARACTERISTICS:
        (A) LENGTH: 2455 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 26..2389

(xi) SEQUENCE DESCRIPTION: SEQ ID NO: 15:

```
AAGCTTTACA ACAAATATAA AAACA ATG AAG TGG GTA ACC TTT ATT TCC CTT      52
                            Met Lys Trp Val Thr Phe Ile Ser Leu
                             1               5

CTT TTT CTC TTT AGC TCG GCT TAT TCC AGG GGT GTG TTT CGT CGA ACC     100
Leu Phe Leu Phe Ser Ser Ala Tyr Ser Arg Gly Val Phe Arg Arg Thr
 10              15                  20                  25

CCC CTG GGC CCT GCC AGC TCC CTG CCC CAG AGC TTC CTG CTC AAG TGC     148
Pro Leu Gly Pro Ala Ser Ser Leu Pro Gln Ser Phe Leu Leu Lys Cys
                 30                  35                  40

TTA GAG CAA GTG AGG AAG ATC CAG GGC GAT GGC GCA GCG CTC CAG GAG     196
Leu Glu Gln Val Arg Lys Ile Gln Gly Asp Gly Ala Ala Leu Gln Glu
             45                  50                  55

AAG CTG TGT GCC ACC TAC AAG CTG TGC CAC CCC GAG GAG CTG GTG CTG     244
Lys Leu Cys Ala Thr Tyr Lys Leu Cys His Pro Glu Glu Leu Val Leu
         60                  65                  70

CTC GGA CAC TCT CTG GGC ATC CCC TGG GCT CCC CTG AGC TCC TGC CCC     292
Leu Gly His Ser Leu Gly Ile Pro Trp Ala Pro Leu Ser Ser Cys Pro
 75                  80                  85

AGC CAG GCC CTG CAG CTG GCA GGC TGC TTG AGC CAA CTC CAT AGC GGC     340
Ser Gln Ala Leu Gln Leu Ala Gly Cys Leu Ser Gln Leu His Ser Gly
 90                  95                 100                 105

CTT TTC CTC TAC CAG GGG CTC CTG CAG GCC CTG GAA GGG ATA TCC CCC     388
Leu Phe Leu Tyr Gln Gly Leu Leu Gln Ala Leu Glu Gly Ile Ser Pro
                110                 115                 120

GAG TTG GGT CCC ACC TTG GAC ACA CTG CAG CTG GAC GTC GCC GAC TTT     436
Glu Leu Gly Pro Thr Leu Asp Thr Leu Gln Leu Asp Val Ala Asp Phe
            125                 130                 135
```

-continued

```
GCC ACC ACC ATC TGG CAG CAG ATG GAA GAA CTG GGA ATG GCC CCT GCC      484
Ala Thr Thr Ile Trp Gln Gln Met Glu Glu Leu Gly Met Ala Pro Ala
        140                 145                 150

CTG CAG CCC ACC CAG GGT GCC ATG CCG GCC TTC GCC TCT GCT TTC CAG      532
Leu Gln Pro Thr Gln Gly Ala Met Pro Ala Phe Ala Ser Ala Phe Gln
    155                 160                 165

CGC CGG GCA GGA GGG GTC CTG GTT GCT AGC CAT CTG CAG AGC TTC CTG      580
Arg Arg Ala Gly Gly Val Leu Val Ala Ser His Leu Gln Ser Phe Leu
170                 175                 180                 185

GAG GTG TCG TAC CGC GTT CTA CGC CAC CTT GCG CAG CCC GGT GGA GGC      628
Glu Val Ser Tyr Arg Val Leu Arg His Leu Ala Gln Pro Gly Gly Gly
                190                 195                 200

GGT GAT GCA CAC AAG AGT GAG GTT GCT CAT CGG TTT AAA GAT TTG GGA      676
Gly Asp Ala His Lys Ser Glu Val Ala His Arg Phe Lys Asp Leu Gly
            205                 210                 215

GAA GAA AAT TTC AAA GCC TTG GTG TTG ATT GCC TTT GCT CAG TAT CTT      724
Glu Glu Asn Phe Lys Ala Leu Val Leu Ile Ala Phe Ala Gln Tyr Leu
        220                 225                 230

CAG CAG TGT CCA TTT GAA GAT CAT GTA AAA TTA GTG AAT GAA GTA ACT      772
Gln Gln Cys Pro Phe Glu Asp His Val Lys Leu Val Asn Glu Val Thr
    235                 240                 245

GAA TTT GCA AAA ACA TGT GTT GCT GAT GAG TCA GCT GAA AAT TGT GAC      820
Glu Phe Ala Lys Thr Cys Val Ala Asp Glu Ser Ala Glu Asn Cys Asp
250                 255                 260                 265

AAA TCA CTT CAT ACC CTT TTT GGA GAC AAA TTA TGC ACA GTT GCA ACT      868
Lys Ser Leu His Thr Leu Phe Gly Asp Lys Leu Cys Thr Val Ala Thr
                270                 275                 280

CTT CGT GAA ACC TAT GGT GAA ATG GCT GAC TGC TGT GCA AAA CAA GAA      916
Leu Arg Glu Thr Tyr Gly Glu Met Ala Asp Cys Cys Ala Lys Gln Glu
            285                 290                 295

CCT GAG AGA AAT GAA TGC TTC TTG CAA CAC AAA GAT GAC AAC CCA AAC      964
Pro Glu Arg Asn Glu Cys Phe Leu Gln His Lys Asp Asp Asn Pro Asn
        300                 305                 310

CTC CCC CGA TTG GTG AGA CCA GAG GTT GAT GTG ATG TGC ACT GCT TTT     1012
Leu Pro Arg Leu Val Arg Pro Glu Val Asp Val Met Cys Thr Ala Phe
    315                 320                 325

CAT GAC AAT GAA GAG ACA TTT TTG AAA AAA TAC TTA TAT GAA ATT GCC     1060
His Asp Asn Glu Glu Thr Phe Leu Lys Lys Tyr Leu Tyr Glu Ile Ala
330                 335                 340                 345

AGA AGA CAT CCT TAC TTT TAT GCC CCG GAA CTC CTT TTC TTT GCT AAA     1108
Arg Arg His Pro Tyr Phe Tyr Ala Pro Glu Leu Leu Phe Phe Ala Lys
                350                 355                 360

AGG TAT AAA GCT GCT TTT ACA GAA TGT TGC CAA GCT GCT GAT AAA GCT     1156
Arg Tyr Lys Ala Ala Phe Thr Glu Cys Cys Gln Ala Ala Asp Lys Ala
            365                 370                 375

GCC TGC CTG TTG CCA AAG CTC GAT GAA CTT CGG GAT GAA GGG AAG GCT     1204
Ala Cys Leu Leu Pro Lys Leu Asp Glu Leu Arg Asp Glu Gly Lys Ala
        380                 385                 390

TCG TCT GCC AAA CAG AGA CTC AAG TGT GCC AGT CTC CAA AAA TTT GGA     1252
Ser Ser Ala Lys Gln Arg Leu Lys Cys Ala Ser Leu Gln Lys Phe Gly
    395                 400                 405

GAA AGA GCT TTC AAA GCA TGG GCA GTA GCT CGC CTG AGC CAG AGA TTT     1300
Glu Arg Ala Phe Lys Ala Trp Ala Val Ala Arg Leu Ser Gln Arg Phe
410                 415                 420                 425

CCC AAA GCT GAG TTT GCA GAA GTT TCC AAG TTA GTG ACA GAT CTT ACC     1348
Pro Lys Ala Glu Phe Ala Glu Val Ser Lys Leu Val Thr Asp Leu Thr
                430                 435                 440

AAA GTC CAC ACG GAA TGC TGC CAT GGA GAT CTG CTT GAA TGT GCT GAT     1396
Lys Val His Thr Glu Cys Cys His Gly Asp Leu Leu Glu Cys Ala Asp
```

-continued

```
                445                     450                     455
GAC AGG GCG GAC CTT GCC AAG TAT ATC TGT GAA AAT CAA GAT TCG ATC    1444
Asp Arg Ala Asp Leu Ala Lys Tyr Ile Cys Glu Asn Gln Asp Ser Ile
        460                     465                     470

TCC AGT AAA CTG AAG GAA TGT TGT GAA AAA CCT CTG TTG GAA AAA TCC    1492
Ser Ser Lys Leu Lys Glu Cys Cys Glu Lys Pro Leu Leu Glu Lys Ser
    475                     480                     485

CAC TGC ATT GCC GAA GTG GAA AAT GAT GAG ATG CCT GCT GAC TTG CCT    1540
His Cys Ile Ala Glu Val Glu Asn Asp Glu Met Pro Ala Asp Leu Pro
490                     495                     500                 505

TCA TTA GCT GCT GAT TTT GTT GAA AGT AAG GAT GTT TGC AAA AAC TAT    1588
Ser Leu Ala Ala Asp Phe Val Glu Ser Lys Asp Val Cys Lys Asn Tyr
            510                     515                     520

GCT GAG GCA AAG GAT GTC TTC CTG GGC ATG TTT TTG TAT GAA TAT GCA    1636
Ala Glu Ala Lys Asp Val Phe Leu Gly Met Phe Leu Tyr Glu Tyr Ala
        525                     530                     535

AGA AGG CAT CCT GAT TAC TCT GTC GTA CTG CTG CTG AGA CTT GCC AAG    1684
Arg Arg His Pro Asp Tyr Ser Val Val Leu Leu Leu Arg Leu Ala Lys
    540                     545                     550

ACA TAT GAA ACC ACT CTA GAG AAG TGC TGT GCC GCT GCA GAT CCT CAT    1732
Thr Tyr Glu Thr Thr Leu Glu Lys Cys Cys Ala Ala Ala Asp Pro His
555                     560                     565

GAA TGC TAT GCC AAA GTG TTC GAT GAA TTT AAA CCT CTT GTG GAA GAG    1780
Glu Cys Tyr Ala Lys Val Phe Asp Glu Phe Lys Pro Leu Val Glu Glu
570                     575                     580                 585

CCT CAG AAT TTA ATC AAA CAA AAT TGT GAG CTT TTT GAG CAG CTT GGA    1828
Pro Gln Asn Leu Ile Lys Gln Asn Cys Glu Leu Phe Glu Gln Leu Gly
            590                     595                     600

GAG TAC AAA TTC CAG AAT GCG CTA TTA GTT CGT TAC ACC AAG AAA GTA    1876
Glu Tyr Lys Phe Gln Asn Ala Leu Leu Val Arg Tyr Thr Lys Lys Val
        605                     610                     615

CCC CAA GTG TCA ACT CCA ACT CTT GTA GAG GTC TCA AGA AAC CTA GGA    1924
Pro Gln Val Ser Thr Pro Thr Leu Val Glu Val Ser Arg Asn Leu Gly
    620                     625                     630

AAA GTG GGC AGC AAA TGT TGT AAA CAT CCT GAA GCA AAA AGA ATG CCC    1972
Lys Val Gly Ser Lys Cys Cys Lys His Pro Glu Ala Lys Arg Met Pro
635                     640                     645

TGT GCA GAA GAC TAT CTA TCC GTG GTC CTG AAC CAG TTA TGT GTG TTG    2020
Cys Ala Glu Asp Tyr Leu Ser Val Val Leu Asn Gln Leu Cys Val Leu
650                     655                     660                 665

CAT GAG AAA ACG CCA GTA AGT GAC AGA GTC ACC AAA TGC TGC ACA GAA    2068
His Glu Lys Thr Pro Val Ser Asp Arg Val Thr Lys Cys Cys Thr Glu
            670                     675                     680

TCC TTG GTG AAC AGG CGA CCA TGC TTT TCA GCT CTG GAA GTC GAT GAA    2116
Ser Leu Val Asn Arg Arg Pro Cys Phe Ser Ala Leu Glu Val Asp Glu
        685                     690                     695

ACA TAC GTT CCC AAA GAG TTT AAT GCT GAA ACA TTC ACC TTC CAT GCA    2164
Thr Tyr Val Pro Lys Glu Phe Asn Ala Glu Thr Phe Thr Phe His Ala
    700                     705                     710

GAT ATA TGC ACA CTT TCT GAG AAG GAG AGA CAA ATC AAG AAA CAA ACT    2212
Asp Ile Cys Thr Leu Ser Glu Lys Glu Arg Gln Ile Lys Lys Gln Thr
715                     720                     725

GCA CTT GTT GAG CTT GTG AAA CAC AAG CCC AAG GCA ACA AAA GAG CAA    2260
Ala Leu Val Glu Leu Val Lys His Lys Pro Lys Ala Thr Lys Glu Gln
730                     735                     740                 745

CTG AAA GCT GTT ATG GAT GAT TTC GCA GCT TTT GTA GAG AAG TGC TGC    2308
Leu Lys Ala Val Met Asp Asp Phe Ala Ala Phe Val Glu Lys Cys Cys
            750                     755                     760

AAG GCT GAC GAT AAG GAG ACC TGC TTT GCC GAG GAG GGT AAA AAA CTT    2356
```

```
Lys Ala Asp Asp Lys Glu Thr Cys Phe Ala Glu Glu Gly Lys Lys Leu
            765                 770                 775

GTT GCT GCA AGT CAA GCT GCC TTA GGC TTA TAACATCACA TTTAAAAGCA        2406
Val Ala Ala Ser Gln Ala Ala Leu Gly Leu
            780                 785

TCTCAGCCTA CCATGAGAAT AAGAGAAAGA AAATGAAGAT CAAAAGCTT                2455
```

(2) INFORMATION FOR SEQ ID NO: 16:

(i) SEQUENCE CHARACTERISTICS:
       (A) LENGTH: 787 amino acids
       (B) TYPE: amino acid
       (D) TOPOLOGY: linear (ii) MOLECULE TYPE: protein (xi) SEQUENCE DESCRIPTION: SEQ ID NO: 16:

```
Met Lys Trp Val Thr Phe Ile Ser Leu Leu Phe Leu Phe Ser Ser Ala
 1               5                  10                  15

Tyr Ser Arg Gly Val Phe Arg Arg Thr Pro Leu Gly Pro Ala Ser Ser
             20                  25                  30

Leu Pro Gln Ser Phe Leu Leu Lys Cys Leu Glu Gln Val Arg Lys Ile
         35                  40                  45

Gln Gly Asp Gly Ala Ala Leu Gln Glu Lys Leu Cys Ala Thr Tyr Lys
     50                  55                  60

Leu Cys His Pro Glu Glu Leu Val Leu Leu Gly His Ser Leu Gly Ile
 65                  70                  75                  80

Pro Trp Ala Pro Leu Ser Ser Cys Pro Ser Gln Ala Leu Gln Leu Ala
                 85                  90                  95

Gly Cys Leu Ser Gln Leu His Ser Gly Leu Phe Leu Tyr Gln Gly Leu
            100                 105                 110

Leu Gln Ala Leu Glu Gly Ile Ser Pro Glu Leu Gly Pro Thr Leu Asp
        115                 120                 125

Thr Leu Gln Leu Asp Val Ala Asp Phe Ala Thr Thr Ile Trp Gln Gln
    130                 135                 140

Met Glu Glu Leu Gly Met Ala Pro Ala Leu Gln Pro Thr Gln Gly Ala
145                 150                 155                 160

Met Pro Ala Phe Ala Ser Ala Phe Gln Arg Arg Ala Gly Gly Val Leu
                165                 170                 175

Val Ala Ser His Leu Gln Ser Phe Leu Glu Val Ser Tyr Arg Val Leu
            180                 185                 190

Arg His Leu Ala Gln Pro Gly Gly Gly Asp Ala His Lys Ser Glu
        195                 200                 205

Val Ala His Arg Phe Lys Asp Leu Gly Glu Glu Asn Phe Lys Ala Leu
    210                 215                 220

Val Leu Ile Ala Phe Ala Gln Tyr Leu Gln Gln Cys Pro Phe Glu Asp
225                 230                 235                 240

His Val Lys Leu Val Asn Glu Val Thr Glu Phe Ala Lys Thr Cys Val
                245                 250                 255

Ala Asp Glu Ser Ala Glu Asn Cys Asp Lys Ser Leu His Thr Leu Phe
            260                 265                 270

Gly Asp Lys Leu Cys Thr Val Ala Thr Leu Arg Glu Thr Tyr Gly Glu
        275                 280                 285

Met Ala Asp Cys Cys Ala Lys Gln Glu Pro Glu Arg Asn Glu Cys Phe
    290                 295                 300

Leu Gln His Lys Asp Asp Asn Pro Asn Leu Pro Arg Leu Val Arg Pro
```

```
                305                     310                     315                     320
Glu Val Asp Val Met Cys Thr Ala Phe His Asp Asn Glu Glu Thr Phe
                325                     330                     335

Leu Lys Lys Tyr Leu Tyr Glu Ile Ala Arg Arg His Pro Tyr Phe Tyr
                340                     345                     350

Ala Pro Glu Leu Leu Phe Phe Ala Lys Arg Tyr Lys Ala Ala Phe Thr
                355                     360                     365

Glu Cys Cys Gln Ala Ala Asp Lys Ala Ala Cys Leu Leu Pro Lys Leu
                370                     375                     380

Asp Glu Leu Arg Asp Glu Gly Lys Ala Ser Ser Ala Lys Gln Arg Leu
385                     390                     395                     400

Lys Cys Ala Ser Leu Gln Lys Phe Gly Glu Arg Ala Phe Lys Ala Trp
                405                     410                     415

Ala Val Ala Arg Leu Ser Gln Arg Phe Pro Lys Ala Glu Phe Ala Glu
                420                     425                     430

Val Ser Lys Leu Val Thr Asp Leu Thr Lys Val His Thr Glu Cys Cys
                435                     440                     445

His Gly Asp Leu Leu Glu Cys Ala Asp Asp Arg Ala Asp Leu Ala Lys
                450                     455                     460

Tyr Ile Cys Glu Asn Gln Asp Ser Ile Ser Ser Lys Leu Lys Glu Cys
465                     470                     475                     480

Cys Glu Lys Pro Leu Leu Glu Lys Ser His Cys Ile Ala Glu Val Glu
                485                     490                     495

Asn Asp Glu Met Pro Ala Asp Leu Pro Ser Leu Ala Ala Asp Phe Val
                500                     505                     510

Glu Ser Lys Asp Val Cys Lys Asn Tyr Ala Glu Ala Lys Asp Val Phe
                515                     520                     525

Leu Gly Met Phe Leu Tyr Glu Tyr Ala Arg Arg His Pro Asp Tyr Ser
                530                     535                     540

Val Val Leu Leu Leu Arg Leu Ala Lys Thr Tyr Glu Thr Thr Leu Glu
545                     550                     555                     560

Lys Cys Cys Ala Ala Ala Asp Pro His Glu Cys Tyr Ala Lys Val Phe
                565                     570                     575

Asp Glu Phe Lys Pro Leu Val Glu Glu Pro Gln Asn Leu Ile Lys Gln
                580                     585                     590

Asn Cys Glu Leu Phe Glu Gln Leu Gly Glu Tyr Lys Phe Gln Asn Ala
                595                     600                     605

Leu Leu Val Arg Tyr Thr Lys Lys Val Pro Gln Val Ser Thr Pro Thr
                610                     615                     620

Leu Val Glu Val Ser Arg Asn Leu Gly Lys Val Gly Ser Lys Cys Cys
625                     630                     635                     640

Lys His Pro Glu Ala Lys Arg Met Pro Cys Ala Glu Asp Tyr Leu Ser
                645                     650                     655

Val Val Leu Asn Gln Leu Cys Val Leu His Glu Lys Thr Pro Val Ser
                660                     665                     670

Asp Arg Val Thr Lys Cys Cys Thr Glu Ser Leu Val Asn Arg Arg Pro
                675                     680                     685

Cys Phe Ser Ala Leu Glu Val Asp Glu Thr Tyr Val Pro Lys Glu Phe
                690                     695                     700

Asn Ala Glu Thr Phe Thr Phe His Ala Asp Ile Cys Thr Leu Ser Glu
705                     710                     715                     720

Lys Glu Arg Gln Ile Lys Lys Gln Thr Ala Leu Val Glu Leu Val Lys
                725                     730                     735
```

His Lys Pro Lys Ala Thr Lys Glu Gln Leu Lys Ala Val Met Asp Asp
                740                 745                 750

Phe Ala Ala Phe Val Glu Lys Cys Cys Lys Ala Asp Asp Lys Glu Thr
            755                 760                 765

Cys Phe Ala Glu Glu Gly Lys Lys Leu Val Ala Ala Ser Gln Ala Ala
        770                 775                 780

Leu Gly Leu
785

(2) INFORMATION FOR SEQ ID NO: 17:

(i) SEQUENCE CHARACTERISTICS:
        (A) LENGTH: 756 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 3..752

(xi) SEQUENCE DESCRIPTION: SEQ ID NO: 17:

```
CC TTA GGC TTA CAG GTG CAG CTC GAG CAG TCT GGA CCT GAG CTG GTG          47
   Leu Gly Leu Gln Val Gln Leu Glu Gln Ser Gly Pro Glu Leu Val
    1               5                  10                  15

AAG CCT GGG GCC TCA GTG AAG ATT TCC TGC AAA GCT TCT GGC TAC GCA         95
Lys Pro Gly Ala Ser Val Lys Ile Ser Cys Lys Ala Ser Gly Tyr Ala
                 20                  25                  30

TTC AGT AGG TCT TGG ATG AAC TGG GTG AAG CAG AGG CCT GGA CAG GGT        143
Phe Ser Arg Ser Trp Met Asn Trp Val Lys Gln Arg Pro Gly Gln Gly
             35                  40                  45

CTT GAG TGG ATT GGA CGG ATT TAT CCT GGA GAT GGA GAT ACC AAA TAC        191
Leu Glu Trp Ile Gly Arg Ile Tyr Pro Gly Asp Gly Asp Thr Lys Tyr
         50                  55                  60

AAT GGG AAG TTC AAG GGC AAG GCC ACA CTG ACT GCG GAC AGA TCA TCC        239
Asn Gly Lys Phe Lys Gly Lys Ala Thr Leu Thr Ala Asp Arg Ser Ser
 65                  70                  75

AGC ACA GCC TAC ATG CAG CTC AGC AGC CTG ACC TCT GTG GGC TCT GCG        287
Ser Thr Ala Tyr Met Gln Leu Ser Ser Leu Thr Ser Val Gly Ser Ala
 80                  85                  90                  95

GTC TAT TTC TGT GCA AAA GAG AAC AAT AGG TTC GAC GAG AGG GGT TAC        335
Val Tyr Phe Cys Ala Lys Glu Asn Asn Arg Phe Asp Glu Arg Gly Tyr
                100                 105                 110

TAT GCT ATG GAC TAC TGG GGC CAA GGG ACC ACG GTC ACC GTC TCC TCA        383
Tyr Ala Met Asp Tyr Trp Gly Gln Gly Thr Thr Val Thr Val Ser Ser
            115                 120                 125

GGT GGC GGT GGC TCG GGC GGT GGT GGG TCG GGT GGC GGC GGA TCT AAC        431
Gly Gly Gly Gly Ser Gly Gly Gly Gly Ser Gly Gly Gly Gly Ser Asn
        130                 135                 140

ATT CAG TTG ACC CAG TCT CCA AAT TCC ATG TCC ACA TCA GTA GGA GAC        479
Ile Gln Leu Thr Gln Ser Pro Asn Ser Met Ser Thr Ser Val Gly Asp
    145                 150                 155

AGG GTC AGC ATC ACC TGC AAG GCC AGT CAG GAT GTG GAT ACT TCT GTA        527
Arg Val Ser Ile Thr Cys Lys Ala Ser Gln Asp Val Asp Thr Ser Val
160                 165                 170                 175

GCC TGG TAT CAA CAG AAA CCA GGG CAA TCT CCT AAA CTA CTG ATT TAC        575
Ala Trp Tyr Gln Gln Lys Pro Gly Gln Ser Pro Lys Leu Leu Ile Tyr
                180                 185                 190

TGG GCA TCC ACC CGG CAC ACT GGA GTC CCT GAT CGC TTC ACA GGC AGT        623
```

-continued

```
            Trp Ala Ser Thr Arg His Thr Gly Val Pro Asp Arg Phe Thr Gly Ser
                        195                 200                 205

GGA TCT GGG ACA GAT TTC ACT CTC ACC ATT AGC AAT GTG CAG TCT GAA              671
Gly Ser Gly Thr Asp Phe Thr Leu Thr Ile Ser Asn Val Gln Ser Glu
            210                 215                 220

GAC TCG GCA GAT TAT TTC TGT CAG CAA TAT AGC AGC TAT CCG TGG ACG              719
Asp Ser Ala Asp Tyr Phe Cys Gln Gln Tyr Ser Ser Tyr Pro Trp Thr
    225                 230                 235

TTC GGT GGA GGG ACC AAG CTG GAG ATC AAA TAAGCTT                              756
Phe Gly Gly Gly Thr Lys Leu Glu Ile Lys
240                 245                 250
```

(2) INFORMATION FOR SEQ ID NO: 18:

(i) SEQUENCE CHARACTERISTICS:
        (A) LENGTH: 249 amino acids
        (B) TYPE: amino acid
        (D) TOPOLOGY: linear (ii) MOLECULE TYPE: protein (xi) SEQUENCE DESCRIPTION: SEQ ID NO: 18:

```
Leu Gly Leu Gln Val Gln Leu Glu Gln Ser Gly Pro Glu Leu Val Lys
  1               5                  10                  15

Pro Gly Ala Ser Val Lys Ile Ser Cys Lys Ala Ser Gly Tyr Ala Phe
             20                  25                  30

Ser Arg Ser Trp Met Asn Trp Val Lys Gln Arg Pro Gly Gln Gly Leu
         35                  40                  45

Glu Trp Ile Gly Arg Ile Tyr Pro Gly Asp Gly Asp Thr Lys Tyr Asn
     50                  55                  60

Gly Lys Phe Lys Gly Lys Ala Thr Leu Thr Ala Asp Arg Ser Ser Ser
 65                  70                  75                  80

Thr Ala Tyr Met Gln Leu Ser Ser Leu Thr Ser Val Gly Ser Ala Val
                 85                  90                  95

Tyr Phe Cys Ala Lys Glu Asn Asn Arg Phe Asp Glu Arg Gly Tyr Tyr
            100                 105                 110

Ala Met Asp Tyr Trp Gly Gln Gly Thr Thr Val Thr Val Ser Ser Gly
        115                 120                 125

Gly Gly Gly Ser Gly Gly Gly Ser Gly Gly Gly Ser Asn Ile
    130                 135                 140

Gln Leu Thr Gln Ser Pro Asn Ser Met Ser Thr Ser Val Gly Asp Arg
145                 150                 155                 160

Val Ser Ile Thr Cys Lys Ala Ser Gln Asp Val Asp Thr Ser Val Ala
                165                 170                 175

Trp Tyr Gln Gln Lys Pro Gly Gln Ser Pro Lys Leu Leu Ile Tyr Trp
            180                 185                 190

Ala Ser Thr Arg His Thr Gly Val Pro Asp Arg Phe Thr Gly Ser Gly
        195                 200                 205

Ser Gly Thr Asp Phe Thr Leu Thr Ile Ser Asn Val Gln Ser Glu Asp
    210                 215                 220

Ser Ala Asp Tyr Phe Cys Gln Gln Tyr Ser Ser Tyr Pro Trp Thr Phe
225                 230                 235                 240

Gly Gly Gly Thr Lys Leu Glu Ile Lys
                245
```

(2) INFORMATION FOR SEQ ID NO: 19:

(i) SEQUENCE CHARACTERISTICS:

(A) LENGTH: 13 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO: 19:

GGCCNNNNNG GCC                                                          13

(2) INFORMATION FOR SEQ ID NO: 20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (ix) FEATURE:
        (A) NAME/KEY: misc_feature
        (B) LOCATION: 12..14
        (D) OTHER INFORMATION: /note= "NNN is repeated p times"

(xi) SEQUENCE DESCRIPTION: SEQ ID NO: 20:

CCTTAGGCTT ANNNTAAGCT T                                                 21

(2) INFORMATION FOR SEQ ID NO: 21:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO: 21:

GAAATGCATA AGCTCTTGCC ATTCTCACCG                                        30

(2) INFORMATION FOR SEQ ID NO: 22:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO: 22:

CCCGGGATCC CTTAGGCTTA ACCTGTGAAG CCTGC                                  35

(2) INFORMATION FOR SEQ ID NO: 23:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO: 23:

CCCGGGATCC AAGCTTAGAC TTGTGCCATG TCG                                    33

(2) INFORMATION FOR SEQ ID NO: 24:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO: 24:

CCCGGGATCC AAGCTTAGTC CTCCACATAC AG                                32

(2) INFORMATION FOR SEQ ID NO: 25:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO: 25:

CCTTAGGCTT AACCTGTGAA GCCTGCCAGG AGCCGGAGG CCTGGTGGTG CCTCCCACAG    60

ATGCCCCGGT GAGCCCCACC ACTCTGTATG TGGAGGACTA AGCTT                  105

(2) INFORMATION FOR SEQ ID NO: 26:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO: 26:

TTAGGCCTCT GTGACCTTGC CCCTGAAGCC CCTCCTCCTA CTCTGCCCCC CTAAGCTTA    59

(2) INFORMATION FOR SEQ ID NO: 27:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO: 27:

GATCTAAGCT TAGGGGGGCA GAGTAGGAGG AGGGGCTTCA GGGGCAAGGT CACAGAGGCC   60

(2) INFORMATION FOR SEQ ID NO: 28:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO: 28:

CCCGGGATCC CTTAGGCTTA ACCGGTGAAG CCGGC                             35

(2) INFORMATION FOR SEQ ID NO: 29:

(i) SEQUENCE CHARACTERISTICS:
        (A) LENGTH: 39 base pairs (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO: 29:

GGATCCTTAG GGCTGTGCAG CAGGCTACTG GACCTGGTC                39

(2) INFORMATION FOR SEQ ID NO: 30:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO: 30:

GAATTCAAGC TTAACAGAGG TAGCTAACGA TCTCGTCCC                39

(2) INFORMATION FOR SEQ ID NO: 31:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO: 31:

CAAGGATCCA AGCTTCAGGG CTGCGCAAGG TGGCGTAG                 38

(2) INFORMATION FOR SEQ ID NO: 32:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO: 32:

CGGGGTACCT TAGGCTTAAC CCCCCTGGGC CCTGCCAGC                39

(2) INFORMATION FOR SEQ ID NO: 33:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO: 33:

TTAGGCTTAG GTGGTGGCGG TACCCCCTG GGCC                      34

(2) INFORMATION FOR SEQ ID NO: 34:

(i) SEQUENCE CHARACTERISTICS:
        (A) LENGTH: 27 base pairs
        (B) TYPE: nucleic acid
        (C) STRANDEDNESS: single
        (D) TOPOLOGY: linear

```
        (ii) MOLECULE TYPE: Other nucleic acid (xi) SEQUENCE DESCRIPTION: SEQ ID NO: 34:

CAGGGGGGTA CCGCCACCAC CTAAGCC                                             27

(2) INFORMATION FOR SEQ ID NO: 35:

(i) SEQUENCE CHARACTERISTICS:
            (A) LENGTH: 66 base pairs
            (B) TYPE: nucleic acid
            (C) STRANDEDNESS: single
            (D) TOPOLOGY: linear (ii) MOLECULE TYPE: Other nucleic acid (xi) SEQUENCE DESCRIPTION: SEQ ID NO: 35:

GTTCTACGCC ACCTTGCGCA GCCCGGTGGA GGCGGTGATG CACACAAGAG TGAGGTTGCT         60

CATCGG                                                                    66

(2) INFORMATION FOR SEQ ID NO: 36:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: Other nucleic acid (xi) SEQUENCE DESCRIPTION: SEQ ID NO: 36:

CAGGGAGCTG GCAGGGCCCA GGGGGGTTCG ACGAAACACA CCCCTGGAAT AAGCCGAGCT         60
```